US012686675B2

(12) United States Patent
Heasley et al.

(10) Patent No.: US 12,686,675 B2
(45) **Date of Patent: *Jul. 21, 2026**

(54) COMPOUNDS AND METHODS OF PREPARING COMPOUNDS S1P1 MODULATORS

(71) Applicant: Trevena, Inc., Chesterbrook, PA (US)

(72) Inventors: Brian H. Heasley, Wake Forest, NC (US); Jennifer Wilent, Raleigh, NC (US); Patrick J. Koestler, Doylestown, PA (US)

(73) Assignee: Trevena, Inc., Chesterbrook, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/495,083

(22) Filed: Oct. 26, 2023

(65) Prior Publication Data

US 2024/0317728 A1 Sep. 26, 2024

Related U.S. Application Data

(63) Continuation of application No. 17/099,895, filed on Nov. 17, 2020, now Pat. No. 11,884,655.

(60) Provisional application No. 62/937,485, filed on Nov. 19, 2019.

(51) Int. Cl.
*C07D 413/14* (2006.01)

(52) U.S. Cl.
CPC ........ *C07D 413/14* (2013.01); *C07B 2200/13* (2013.01)

(58) Field of Classification Search
CPC .................................................... C07D 413/14
USPC .......................................................... 514/364
See application file for complete search history.

(56) References Cited

U.S. PATENT DOCUMENTS

| | | | |
|---|---|---|---|
| 11,884,655 B2 * | 1/2024 | Heasley | C07D 413/14 |
| 11,912,693 B2 | 2/2024 | Pitis et al. | |
| 2006/0035944 A1 | 2/2006 | Muto et al. | |
| 2011/0118231 A1 | 5/2011 | Akritopoulou-Zanze et al. | |
| 2011/0212940 A1 | 9/2011 | Burli et al. | |
| 2012/0115849 A1 | 5/2012 | Demopulos et al. | |
| 2012/0129828 A1 | 5/2012 | Cee et al. | |
| 2013/0237566 A1 | 9/2013 | Cherney et al. | |
| 2014/0066427 A1 | 3/2014 | Gill et al. | |
| 2015/0359755 A1 | 12/2015 | Guy et al. | |
| 2016/0235718 A1 | 8/2016 | Baraban | |
| 2021/0147402 A1 | 5/2021 | Heasley et al. | |
| 2021/0188826 A1 | 6/2021 | Pitis et al. | |
| 2023/0114241 A1 | 4/2023 | Demitrack et al. | |
| 2023/0234946 A1 | 7/2023 | Pitis et al. | |

FOREIGN PATENT DOCUMENTS

| | | | |
|---|---|---|---|
| EA | 011707 | B1 | 4/2009 |
| EP | 1247810 | A1 | 10/2002 |
| EP | 2003132 | A1 | 12/2008 |
| EP | 2210890 | A1 | 7/2010 |
| EP | 2671881 | A1 | 12/2013 |
| EP | 2853532 | A1 | 4/2015 |
| JP | 2008515985 | A | 5/2008 |
| JP | 2009520751 | A | 5/2009 |
| JP | 2011522818 | A | 8/2011 |
| JP | 2011530485 | A | 12/2011 |
| JP | 2019507185 | A | 3/2019 |
| TW | 201004944 | A | 2/2010 |
| WO | 20000003681 | A2 | 1/2000 |
| WO | 2003103657 | A1 | 12/2003 |
| WO | 2004018462 | A1 | 3/2004 |
| WO | 2004022554 | A1 | 3/2004 |
| WO | 2004026863 | A1 | 4/2004 |
| WO | 2006044456 | A1 | 4/2006 |
| WO | 2007071598 | A1 | 6/2007 |
| WO | 2007116866 | A1 | 10/2007 |
| WO | 2008049864 | A1 | 5/2008 |
| WO | 2009133970 | A1 | 11/2009 |
| WO | 2009146343 | A1 | 12/2009 |
| WO | 2009148452 | A1 | 12/2009 |
| WO | 2010043000 | A1 | 4/2010 |
| WO | 2011059619 | A1 | 5/2011 |
| WO | 2011073299 | A1 | 6/2011 |
| WO | 2011126960 | A1 | 10/2011 |
| WO | 2012154760 | A1 | 11/2012 |
| WO | 2013053051 | A1 | 4/2013 |
| WO | 2013181931 | A1 | 12/2013 |
| WO | 2014029684 | A1 | 2/2014 |
| WO | 2014063199 | A1 | 5/2014 |
| WO | 2016028959 | A1 | 2/2016 |
| WO | 2016128959 | A1 | 8/2016 |
| WO | 2016209809 | A1 | 12/2016 |
| WO | 2017136309 | A1 | 8/2017 |
| WO | 2018140504 | A1 | 8/2018 |
| WO | 2018231745 | A1 | 12/2018 |
| WO | 2021046183 | A1 | 3/2021 |

(Continued)

OTHER PUBLICATIONS

Advisory Action from U.S. Appl. No. 16/613,152 dated Nov. 2, 2022.
Ashok et al., "Synthesis of Novel 2,4,6-Trisubstituted Pyrimidine Derivatives and Their In Vitro Antimicrobial Activity," Russian Journal of General Chemistry, 2016, vol. 86, No. 6, pp. 1396-1404.
Birch et al., "Novel 7-methoxy-6-oxazol-5-yl-2,3-dihydro-1H-quinazolin-4-ones as IMPDH Inhibitors," Bioorganic & Medicinal Chemistry Letters, 2005, vol. 15, pp. 5335-5339.
Doria Filippo et al: "Oxadiazole/Pyridine-Based Ligands: a Structural Tuning for Enhancing G-Quadruplex Binding", Molecules, vol. 23, No. 9, Aug. 28, 2018 (Aug. 28, 2018), p. 2162, XP093094606, DOI:10.3390/molecules23092162.

(Continued)

*Primary Examiner* — Kahsay Habte
(74) *Attorney, Agent, or Firm* — Goodwin Procter LLP

(57) ABSTRACT

The present embodiments are directed, in part, to processes and compositions that can, for example, be used in the preparation compounds of Formula (I), or a pharmaceutically acceptable salts thereof.

4 Claims, 6 Drawing Sheets

(56) References Cited

FOREIGN PATENT DOCUMENTS

WO 2021101854 A1 5/2021

OTHER PUBLICATIONS

Ex Parte Quayle, dated May 10, 2023, in U.S. Appl. No. 17/099,895.
Fantini Met al: "2,4(5)-Diarylimidazoles as inhibitors of hNa"VI.2 sodium channels: Pharmacological evaluation and structure-property relationships", Bioorganic & Medicinal Chemistry, Elsevier, Amsterdam, NL, vol. 17, No. 10, May 15, 2009 (May 15, 2009), pp. 3642-3648, XP026090835, ISSN: 0968-0896, DOI: 10.1016/J.BMC.2009.03.067, [retrieved on Apr. 10, 2009], * introduction; compounds 3-24 *.
Final Office Action for U.S. Appl. No. 16/613,152 dated Jul. 20, 2022.
Hemalatha et al., "Binding Mode of Dihydroquinazolinones with Lysozyme and its Antifungal Activity Against *Apergillus* Species," Journal of Photochemistry & Photobiology, B: Biology, 2016, vol. 161, pp. 71-79.
International Preliminary Report on Patentability for International PCT Application No. PCT/US2018/036989 dated Dec. 17, 2019.
International Preliminary Report on Patentability for International PCT Application No. PCT/US2020/049147 dated Mar. 17, 2022.
International Preliminary Report on Patentability for International PCT Application No. PCT/US2020/060822 dated May 17, 2022.
International Search Report and Written Opinion dated Feb. 2, 2021 for PCT Application No. PCT/US2020/049147.
International Search Report and Written Opinion dated Mar. 17, 2021 for PCT Application No. PCT/US2020/60822.
International Search Report and Written Opinion for International PCT Application No. PCT/US2018/036989 dated Oct. 25, 2018.
Maha, Tetrahedron, 2016, 72, 2874-2879, 2016.
Mirko Rivara et al: "In vivo screening of diarylimidazoles as anticonvulsant agents", Medicinal Chemistry Research, Birkhauser-Verlag, Boston, vol. 21, No. 11, Nov. 19, 2011 (Nov. 19, 2011), pp. 3428-3434, XP035119527, ISSN: 1554-8120, DOI: 10.1007/S00044-011-9869-9* introduction; compounds 1-9 *.
Non-Final Office Action, dated Nov. 25, 2022, issued in U.S. Appl. No. 17/099,895.
Non-Final Office Action, dated Oct. 15, 2021, issued in U.S. Appl. No. 16/613,152.
Notice of Allowance for U.S. Appl. No. 16/613,152 dated Jan. 4, 2023.
Notice of Allowance, dated Jul. 27, 2023, issued in U.S. Appl. No. 17/099,895.
Notice of Allowance-Corrected, dated Dec. 18, 2023, issued in U.S. Appl. No. 17/099,895.
PubChem CID 117960303 Create Date: Feb. 23, 2016 Date Accessed; Apr. 22, 2023 p. 2 formula.
PubChem CID 43591546 Create Date: Jul. 21, 2009 Date Accessed; Oct. 2, 2018 p. 3.
Ramon Subiros-Funosas et al: "Oxyma: an Efficient Additive for Peptide Synthesis to Replace the Benzotriazole-Based HOBt and HOAt with a Lower Risk of Explosion", Chemistry—a European Journal, vol. 15, No. 37, Jul. 2, 2009 (Jul. 2, 2009), pp. 9394-9403, XP071829479.
Xu et al., "Discovery and Modification of In Vivo Active Nrf2 Activators with 1,2,4-Oxadiazole Core: Hits Identification and Structure-Activity Relationship Study," Journal of Medicinal Chemistry, 2015, vol. 58, pp. 5419-5436.
Zuliani Vet al: "Anticonvulsant activity of 2,4(1H)-diarylimidazoles in mice and rats acute seizure models", Bioorganic & Medicinal Chemistry, Elsevier, Amsterdam, NL, vol. 18, No. 22, Nov. 15, 2010 (Nov. 15, 2010), pp. 7957-7965, XP027452458, ISSN: 0968-0896, DOI: 10.1016/J.BMC.2010.09.029, [retrieved on Sep. 22, 2010]* introduction; compounds 3-29 *.

* cited by examiner

| | Name | Retention Time | Area | % Area | Height |
|---|---|---|---|---|---|
| 1 | | 1.686 | 156978.93 | 1.16 | 19141 |
| 2 | STG1 Product | 1.902 | 13368671.61 | 98.72 | 1737977 |
| 3 | | 2.961 | 16501.73 | 0.12 | 1402 |

| | Name | Retention Time | Area | % Area | Height |
|---|---|---|---|---|---|
| 1 | | 8.581 | 23936.85 | 0.27 | 5264 |
| 2 | | 9.888 | 7162.29 | 0.08 | 1371 |
| 3 | | 9.993 | 6793.95 | 0.08 | 1240 |
| 4 | | 10.608 | 63220.98 | 0.72 | 19524 |
| 5 | | 11.370 | 26218.24 | 0.30 | 6296 |
| 6 | STG 2 Product | 14.355 | 8405259.35 | 96.29 | 1811598 |
| 7 | | 15.289 | 50433.21 | 0.58 | 14357 |
| 8 | | 15.726 | 34080.71 | 0.39 | 5829 |
| 9 | | 15.875 | 44680.74 | 0.51 | 11362 |
| 10 | | 16.750 | 35354.65 | 0.41 | 9902 |
| 11 | | 17.255 | 25406.86 | 0.29 | 6353 |
| 12 | | 17.444 | 6660.65 | 0.08 | 1979 |

| | Name | Retention Time | Area | % Area | Height |
|---|---|---|---|---|---|
| 1 | | 8.581 | 23936.85 | 0.27 | 5264 |
| 2 | | 9.888 | 7162.29 | 0.08 | 1371 |
| 3 | | 9.993 | 6793.95 | 0.08 | 1240 |
| 4 | | 10.698 | 63220.98 | 0.72 | 19524 |
| 5 | | 11.370 | 26218.24 | 0.30 | 6296 |
| 6 | STG 2 Product | 14.355 | 8405259.35 | 96.29 | 1811508 |
| 7 | | 15.289 | 50433.21 | 0.58 | 14357 |
| 8 | | 15.726 | 34080.71 | 0.39 | 5829 |
| 9 | | 15.875 | 44680.74 | 0.51 | 11382 |
| 10 | | 16.750 | 35354.65 | 0.41 | 9902 |
| 11 | | 17.255 | 25406.86 | 0.29 | 6353 |
| 12 | | 17.444 | 6660.65 | 0.08 | 1979 |

Temperature (°C)

COMPOUNDS AND METHODS OF PREPARING COMPOUNDS S1P1 MODULATORS

CROSS-REFERENCE TO RELATED APPLICATIONS

The present application is a continuation of U.S. application Ser. No. 17/099,895, filed on Nov. 17, 2020, which claims priority to U.S. Provisional Application No. 62/937,485, filed Nov. 19, 2019, which are hereby incorporated by reference in their entirety.

FIELD

Embodiments disclosed herein are directed to compounds and methods of preparing compounds, or pharmaceutically acceptable salts thereof, that can, for example, be used for modulating S1P1 receptor activity.

BACKGROUND

Compounds of

Formula (I)

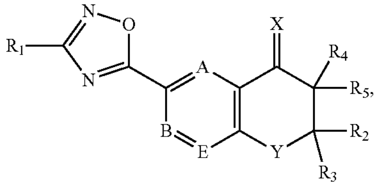

are reported in International Application Publication No. WO 2018/231745, which is hereby incorporated by reference in its entirety. In addition to the methods of making such compounds, or pharmaceutically acceptable salts thereof, others methods of synthesis may still be needed. The present disclosure fulfills these needs and others.

SUMMARY OF EMBODIMENTS

In some embodiments, methods of preparing compounds of Formula (I), or a pharmaceutically acceptable salt thereof are provided. In some embodiments, the methods comprise contacting Formula (II)

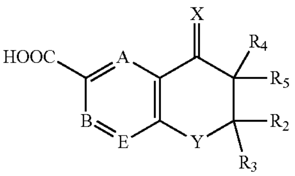

with

Formula (III)

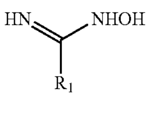

under suitable conditions to produce the compound having the structure of

Formula (I)

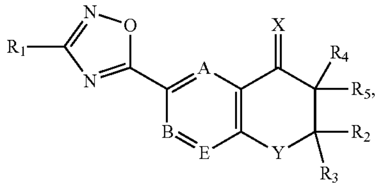

wherein A, B, E, X, Y, $R_1$, $R_2$, $R_3$, $R_4$, and $R_5$ are as provided for herein and, for example, can be selected from the respective groups of chemical moieties described herein.

In some embodies, the methods comprise:

(a) adding a coupling reagent and optionally an additive to a solution of a compound of Formula (II)

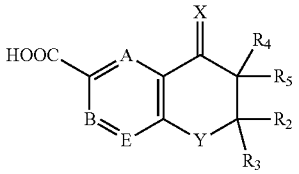

in a first organic solvent to form a mixture and stirring the mixture for at least about 5 minutes;

(b) stirring the mixture of step (a) with a compound of

Formula (III)

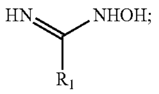

(c) heating the mixture of step (b) to a temperature of at least about 40° C. and stirring the mixture under the temperature;

(d) cooling the mixture of step (c) and adding water to the mixture to form a slurry;

(e) stirring the slurry of step (d);

(f) filtering the slurry of step (e) to obtain a solid;

(g) washing the solid of the step (f) with water and/or a second organic solvent; and (h) drying the solid of the step (g) at a temperature of at least about 30° C. under vacuum to form the compound of Formula (I)

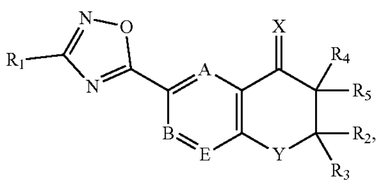

wherein the variables are provided herein.

In some embodiments, also provided are processes of preparing compounds of Formula (I), or a pharmaceutically acceptable salt thereof comprising the steps of:

(a) adding EDC hydrochloride and ethyl cyanohydroxyiminoacetate to a solution of a compound of Formula (II)

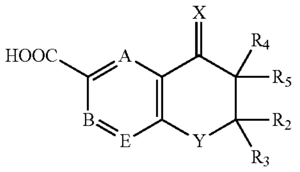

in dimethylformamide to form a mixture and stirring the mixture for at least about 1 hour;

(b) stirring the mixture of the step (a) with a compound of

Formula (III)

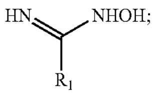

(c) heating the mixture of the step (b) to a temperature at about 95° C. and stirring the mixture under the temperature for at least about 5 hour;

(d) cooling the mixture of the step (c) to about 15-20° C. and adding water to form a slurry;

(e) stirring the slurry of the step (d) at about 15-20° C. for about 1 h;

(f) filtering the slurry of the step (e) to from a solid;

(g) washing the solid of the step (f) with water and methyl-tert-butyl ether; and (h) drying the solid of the step (g) at about 55° C. under vacuum to form the compound of Formula (I)

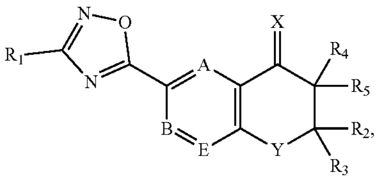

wherein the variables are as defined herein.

In some embodiments, also provided are processes of preparing the compound having the structure of

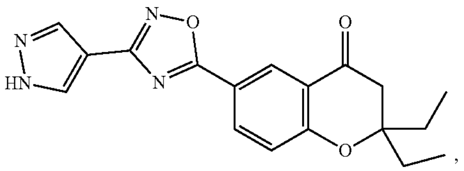 [SMILES: CCC1(CC)CC(=O)c2cc(-c3nc(-c4cn[nH]c4)no3)ccc2O1]

or a pharmaceutically acceptable salt thereof comprising the steps of:

(a) adding EDC hydrochloride and ethyl cyanohydroxyiminoacetate to a solution of

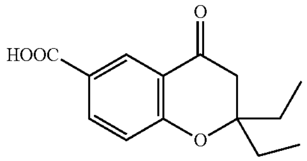

in dimethylformamide to form a mixture and stirring the mixture for at least about 1 hour;

(b) stirring the mixture of the step (a) with

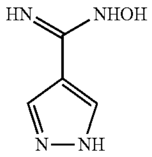

for about 1 hour;

(c) heating the mixture of the step (b) to a temperature at about 95° C. and stirring the mixture under the temperature for at least about 5 hour;

(d) cooling the mixture of the step (c) to about 15-20° C. and adding water to the mixture form a slurry;

(e) stirring the slurry of the step (d) at about 15-20° C. for about 1 h;

(f) filtering the slurry of the step (e) to from a solid;

(g) washing the solid of the step (f) with water and methyl-tert-butyl ether; and (h) drying the solid of the step (g) at least about 55° C. under vacuum to form

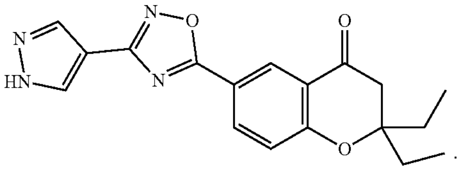 [SMILES: CCC1(CC)CC(=O)c2cc(-c3nc(-c4cn[nH]c4)no3)ccc2O1]

In some embodiments, provided are processes of preparing compounds of Formula (I), or a pharmaceutically acceptable salt thereof further comprising a method of preparing a compound of Formula (II)

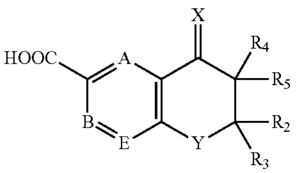

comprising contacting

Formula (V)

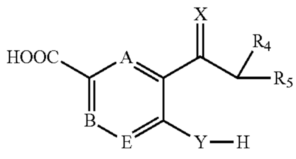

with $R_2R_3C{=}O$ under suitable conditions, wherein the variables are as defined herein.

In some embodiments, also provided are methods of preparing compounds of

Formula (II)

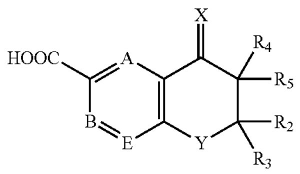

comprising the steps of:

(a) adding pyrrolidine to a solution of a compound of

Formula (V)

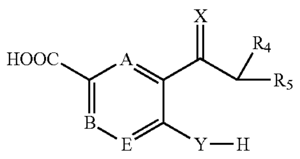

in a compound of $R_2R_3C{=}O$ to form a mixture;

(b) heating the mixture of step (a) to reflux, stirring the mixture for about 19.5 hours under the temperature, cooling the mixture to about 15-20° C., and adding water to the mixture;

(c) adjusting the pH of the mixture of step (b) to about 2 with HCl;

(d) stirring the mixture of step (c) with n-heptane to form a slurry and stirring the slurry at about 15-20° C. for about 1 hour, and filtering the slurry to form a solid; and (e) washing the solid of step (d) with water and n-heptane; and (f) drying the solid of step (e) at about 50° C. under vacuum to form the compound of Formula (II)

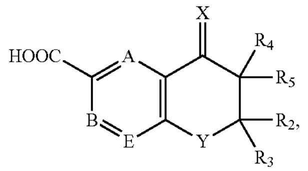

wherein:

A, B, and E are each independently N or $CR_6$;

X and Y are each independently O, S, or $NR_7$, $R_2$, $R_3$, $R_4$, $R_5$, $R_6$, and $R_7$, are each independently H, optionally substituted $C_1$-$C_6$ alkyl, optionally substituted $C_1$-$C_6$ hydroxyalkyl, optionally substituted C1-C6 alkoxy, optionally substituted cycloalkyl, or optionally substituted cycloheteroalkyl; $R_2$ and $R_3$ are together optionally substituted cycloalkyl, or optionally substituted cycloheteroalkyl; or $R_4$ and $R_5$ are together optionally substituted cycloalkyl, or optionally substituted cycloheteroalkyl.

In some embodiments, provided are processes of preparing compounds of Formula (I), or a pharmaceutically acceptable salt thereof further comprising methods of preparing a compound of Formula (III)

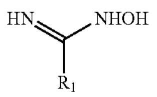

comprising contacting a compound of a formula of $R_1CN$ with ammonium hydroxide and wherein $R_1$ is H, OH, $NH_2$, $NO_2$, optionally substituted carbocycle, optionally substituted aryl group, optionally substituted heteroaryl group, branched or unbranched alkyl alcohol, halo, branched or unbranched alkyl, amide, cyano, alkoxy, haloalkyl, aklylsulfonyl, nitrite, or alkylsulfanyl.

In some embodiments, also provided are methods of preparing a compound of

Formula (III)

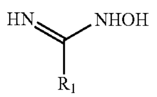

comprising the steps of:

(a) adding hydroxylamine to a solution of a compound of $R_1CN$ in an alcohol form a mixture;

(b) heating the mixture of the step (a) to a temperature of about 75° C. and stirring the mixture for about 4 hours under the temperature to form a slurry (c) cooling the slurry of the step (b) to ambient temperature and stirring for about 16 hours under the ambient temperature;

(d) filtering the slurry of the step (c) to form a solid; and (e) washing the solid of the step (d) with the alcohol and drying the washed solid at about 50° C. under vacuum to form the compound of Formula (III)

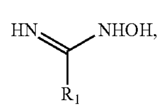

$R_1$ is as defined herein.

In some embodiments, provided are methods of preparing compounds of Formula (I), or a pharmaceutically acceptable salt thereof, wherein the compound of Formula (II)

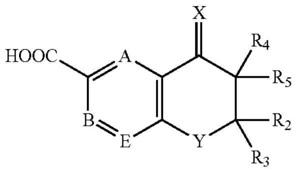

is contacted with the coupling reagent, with or without the addictive, to form an intermediate having the structure of Formula (XIII)

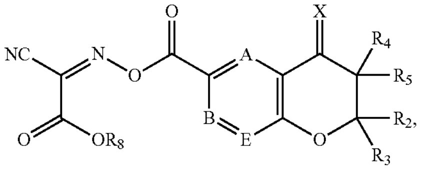

wherein $R_8$ is optionally substituted C1-C6 alkyl and $R_2$, $R_3$, $R_4$, $R_5$, $R_6$, and $R_8$, are as defined herein. In some embodiments, the intermediate of Formula (XIII) is a compound having the structure of

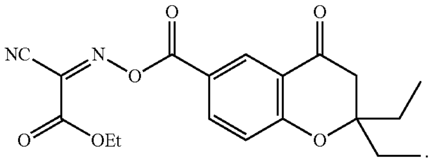 [SMILES: CCOC(=O)/C(C#N)=N\OC(=O)c1ccc2c(c1)C(=O)CC(CC)(CC)O2]

In some embodiments, provided are processes of preparing compounds of Formula (I), or a pharmaceutically acceptable salt thereof, wherein the intermediate having the structure of Formula (XIII)

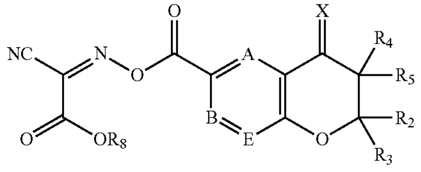

further contacts the compound of

Formula (III)

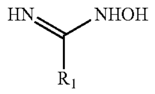

to form an intermediate having a structure of

Formula (XVI)

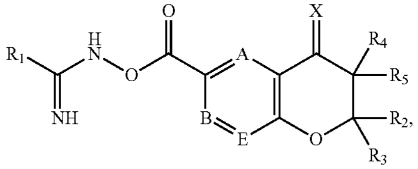

wherein the variables are as defined herein. In some embodiments, the intermediate of Formula (XVI) is a compound having the structure of

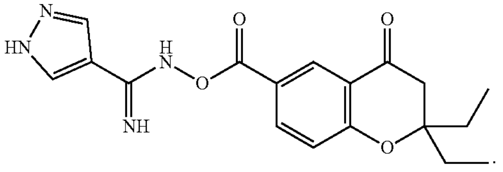 [SMILES: CCC1(CC)CC(=O)c2cc(C(=O)ONC(=N)c3cn[nH]c3)ccc2O1]

In some embodiments, a compound of

Formula (XIII)

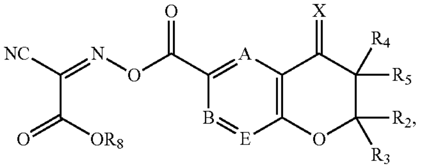

or a pharmaceutically acceptable salt thereof, wherein $R_8$ is optionally substituted C1-C6 alkyl and $R_2$, $R_3$, $R_4$, $R_5$, $R_6$, and $R_7$, are as defined herein, is provided. In some embodiments, a compound having the structure of Formula (XIII)

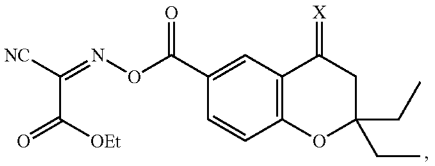

or a pharmaceutically acceptable salt thereof is provided.

In some embodiments, a compound having the structure of

Formula (XVI)

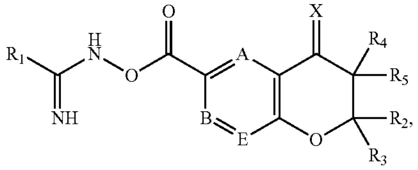

or a pharmaceutically acceptable salt thereof is provided, wherein the variables are as defined herein. In some embodiments, a compound having the structure of

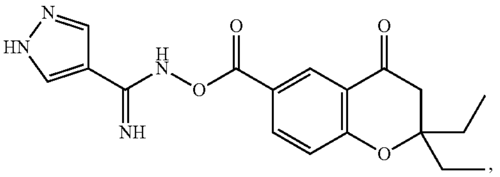 [SMILES: CCC1(CC)CC(=O)c2cc(C(=O)ONC(=N)c3cn[nH]c3)ccc2O1]

or a pharmaceutically acceptable salt thereof, is provided.

In some embodiments, a method of forming a compound of Formula I, the method comprising reacting the compound having the formula of Formula (XVI)

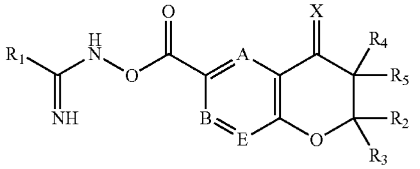

under thermal cyclodehydration conditions to form a compound of

Formula I

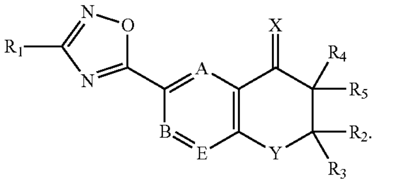

In some embodiments, a crystalline form of the compound having the formula

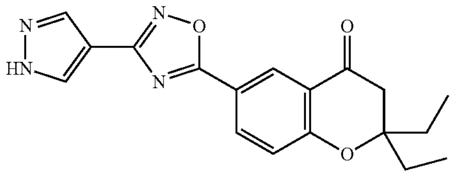 [SMILES: CCC1(CC)CC(=O)c2cc(-c3nc(-c4cn[nH]c4)no3)ccc2O1]

is provided. In some embodiments, the crystalline form is Form I.

DETAILED DESCRIPTION

Figure 1:
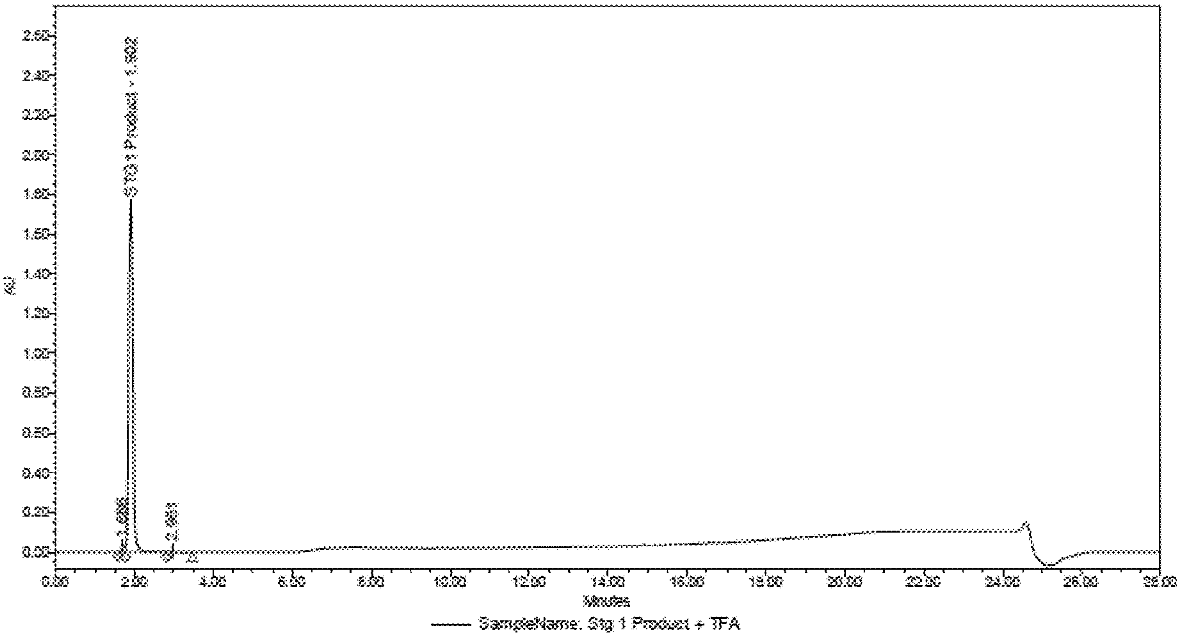
FIG. 1: High performance liquid chromatography (HPLC) chromatogram of N-hydroxy-1H-pyrazole-4-carboximidamide (Compound 2-2).
Figure 2:
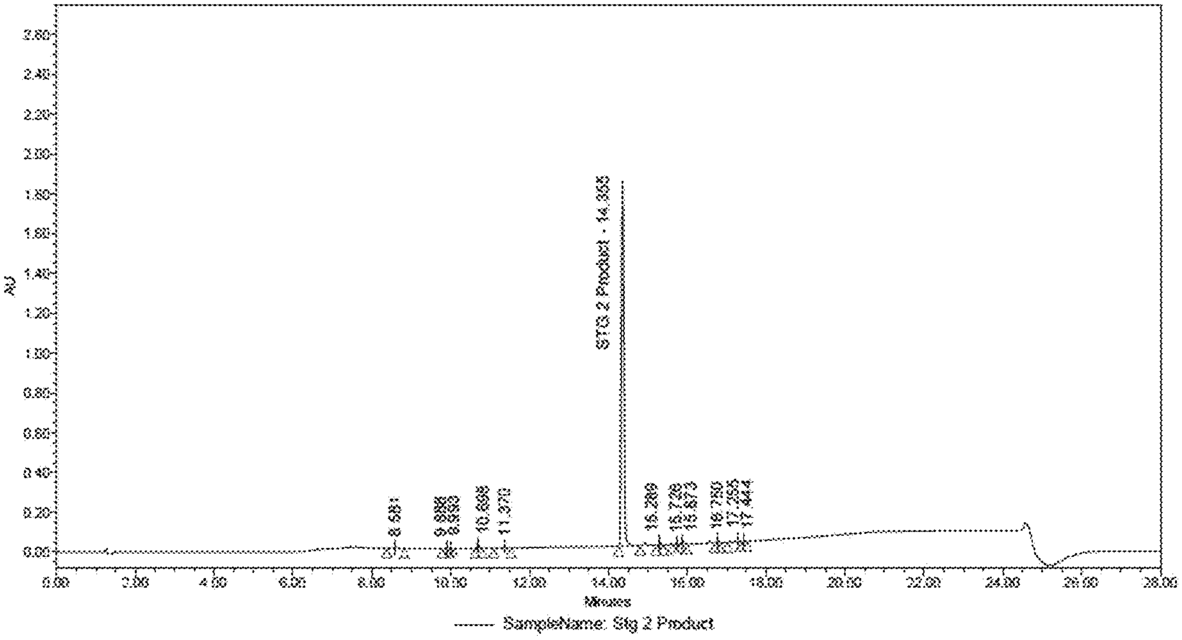
FIG. 2: High performance liquid chromatography (HPLC) chromatogram of 2,2-diethyl-4-oxo-3,4-dihydro-2H-1-benzopyran-6-carboxylic acid (Compound 4-2).
Figure 3:
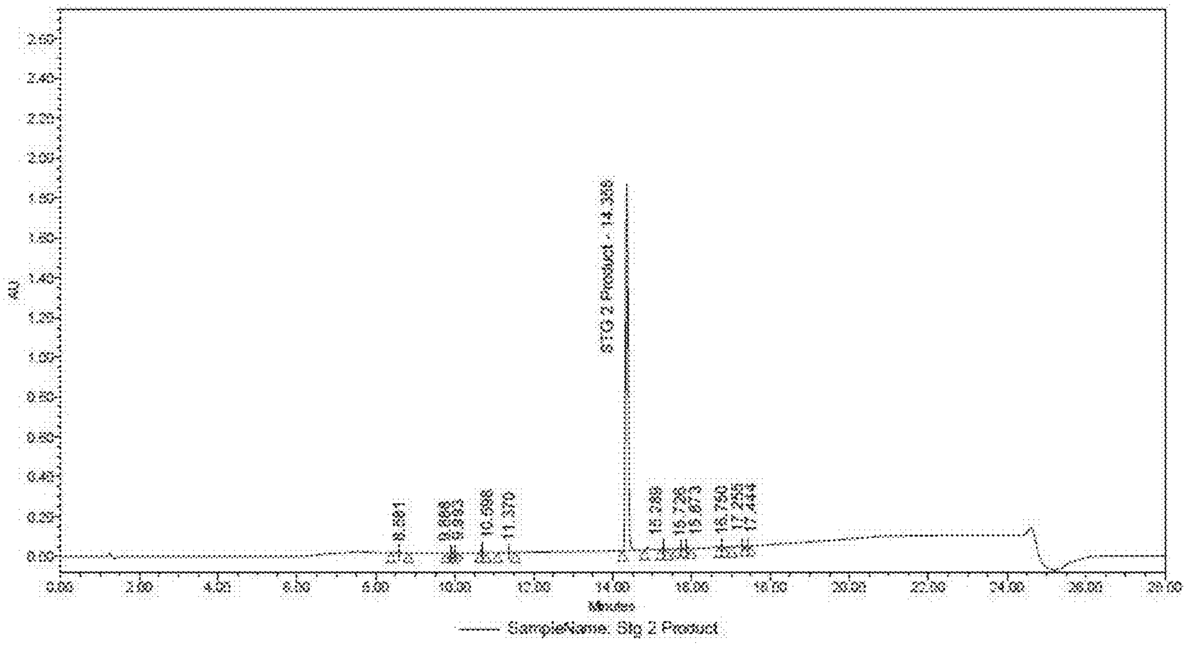
FIG. 3: High performance liquid chromatography (HPLC) chromatogram of 6-(3-(1H-pyrazol-4-yl)-1,2,4-oxadiazol-5-yl)-2,2-diethylchroman-4-one (Compound 6-1).

Unless defined otherwise, all technical and scientific terms have the same meaning as is commonly understood by one of ordinary skill in the art to which the embodiments disclosed belongs. In the event that there is a plurality of definitions for terms cited herein, those in this section prevail unless otherwise stated. All patents, applications, published applications, and other publications cited herein are incorporated by reference in their entirety.

As used herein, the terms "a" or "an" means that "at least one" or "one or more" unless the context clearly indicates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

As used herein, the term "additive" or "coupling additive" means a reagent that is suitable in combination with a coupling reagent in coupling reactions to inhibit side reactions and reduce or eliminate racemization. In some embodiments, an additive is, but not limited to, ethyl cyanohydroxyiminoacetate, N-hydroxysuccinimide (HOSu), N-hydroxy-5-norbornene2,3-dicarboximide (HONB), 1-hydroxybenzotriazole (HOBt), 6-chloro-1-hydroxybenzotriazole (6-Cl-HOBt), 1-hydroxy-7-azabenzotriazole (HOAt) or 3-hydroxy-4-oxo-3,4-dihydro-1,2,3-benzotriazine (HODhbt), aza derivative of 3-hydroxy-4-oxo-3,4-dihydro-1,2,3-benzotriazine (HODhat), 4-(N,N-Dimethylamino) pyridine) (DMAP), N-hydroxysuccinimide (HOSu), N-hydroxy-5-norbornene-2,3-dicarboximide (HONB), or any combinations thereof.

As used herein, the term "alcohol" means any organic compound in which a hydroxyl group (—OH) is bound to a carbon atom, which in turn is bound to other hydrogen and/or carbon atoms. For example, the term "alcohol" means a straight or branched alkyl-OH group of 1 to 20 carbon atoms, including, but not limited to, methanol, ethanol, n-propanol, isopropanol, t-butanol, and the like. In some embodiments, the alkyl-OH chain is from 1 to 10 carbon atoms in length, from 1 to 8 carbon atoms in length, from 1 to 6 carbon atoms in length, from 1 to 4 carbon atoms in length, from 2 to 10 carbon atoms in length, from 2 to 8 carbon atoms in length, from 2 to 6 carbon atoms in length, or from 2 to 4 carbon atoms in length.

As used herein, the terms "alkoxy", "phenyloxy", "benzoxy" and "pyrimidinyloxy" refer to an alkyl group, phenyl group, benzyl group, or pyrimidinyl group, respectively, each optionally substituted, that is bonded through an oxygen atom. For example, the term "alkoxy" means a straight or branched-O-alkyl group of 1 to 20 carbon atoms, including, but not limited to, methoxy, ethoxy, n-propoxy, isopropoxy, t-butoxy, and the like. In some embodiments, the alkoxy chain is from 1 to 10 carbon atoms in length, from 1 to 8 carbon atoms in length, from 1 to 6 carbon atoms in length, from 1 to 4 carbon atoms in length, from 2 to 10 carbon atoms in length, from 2 to 8 carbon atoms in length, from 2 to 6 carbon atoms in length, or from 2 to 4 carbon atoms in length.

As used herein, the term “alkyl” means a saturated hydrocarbon group, which is straight-chained or branched. An alkyl group can contain from 1 to 20, from 2 to 20, from 1 to 10, from 2 to 10, from 1 to 8, from 2 to 8, from 1 to 6, from 2 to 6, from 1 to 4, from 2 to 4, from 1 to 3, or 2 or 3 carbon atoms. Examples of alkyl groups include, but are not limited to, methyl (Me), ethyl (Et), propyl (e.g., n-propyl and isopropyl), butyl (e.g., n-butyl, t-butyl, isobutyl), pentyl (e.g., n-pentyl, isopentyl, neopentyl), hexyl, isohexyl, heptyl, 4,4-dimethylpentyl, octyl, 2,2,4-trimethylpentyl, nonyl, decyl, undecyl, dodecyl, 2-methyl-1-propyl, 2-methyl-2-propyl, 2-methyl-1-butyl, 3-methyl-1-butyl, 2-methyl-3-butyl, 2-methyl-1-pentyl, 2,2-dimethyl-1-propyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, and the like.

As used herein, the term “alkylene” or “alkylenyl” means a divalent alkyl linking group. An example of an alkylene (or alkylenyl) is methylene or methylenyl (—CH2-).

As used herein, the term “alkynyl” means a straight or branched alkyl group having one or more triple carbon-carbon bonds and 2-20 carbon atoms, including, but not limited to, acetylene, 1-propylene, 2-propylene, and the like. In some embodiments, the alkynyl chain is 2 to 10 carbon atoms in length, from 2 to 8 carbon atoms in length, from 2 to 6 carbon atoms in length, or from 2 to 4 carbon atoms in length.

As used herein, the terms “ambient temperature” and “room temperature” or “RT”, as used herein, are understood in the art, and refer generally to a temperature, e.g. a reaction temperature, that is about the temperature of the room in which the reaction is carried out, for example, a temperature from about 20° C. to about 30° C., such as at or about 25° C.

As used herein, the term “amide” means to a functional group containing a carbonyl group linked to a nitrogen atom or any compound containing the amide functional group. For example, amides are derived from carboxylic acid and an amine.

As used herein, the term “aryl” means a monocyclic, bicyclic, or polycyclic (e.g., having 2, 3 or 4 fused rings) aromatic hydrocarbons. In some embodiments, aryl groups have from 6 to 20 carbon atoms or from 6 to 10 carbon atoms. Examples of aryl groups include, but are not limited to, phenyl, naphthyl, anthracenyl, phenanthrenyl, indanyl, indenyl, tetrahydronaphthyl, and the like. Examples of aryl groups include, but are not limited to:

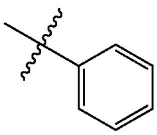
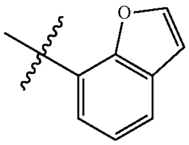
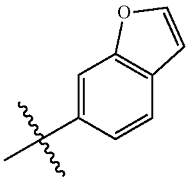
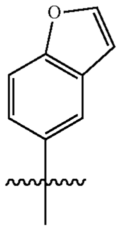
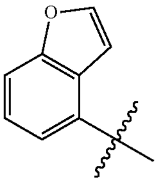

-continued

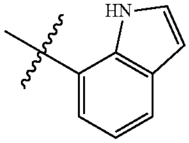
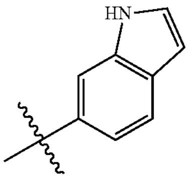
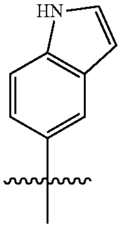
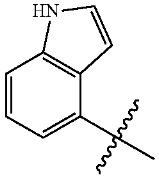
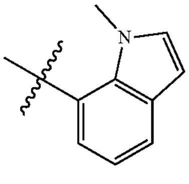
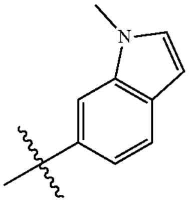
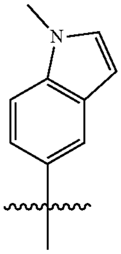
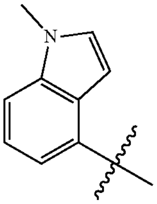
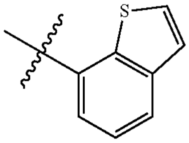
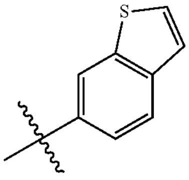
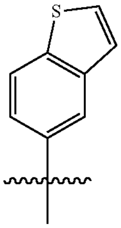
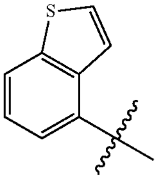
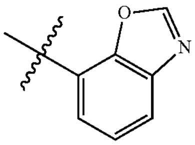
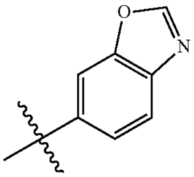
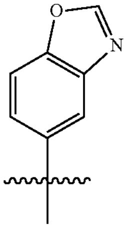
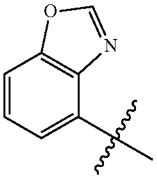
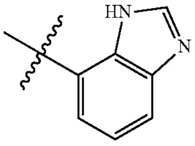
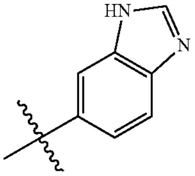
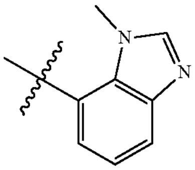
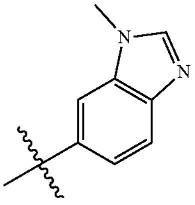

13
-continued
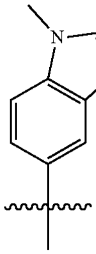
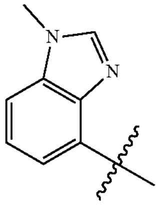
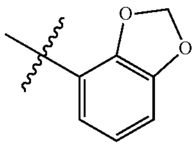
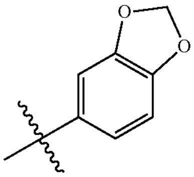
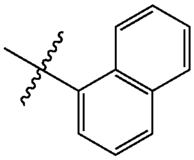
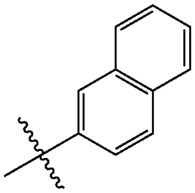
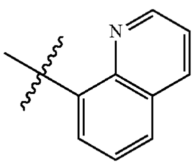
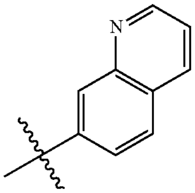
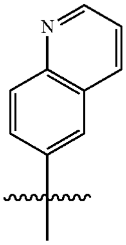
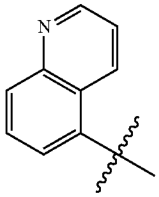
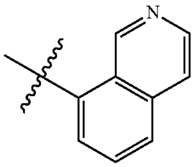
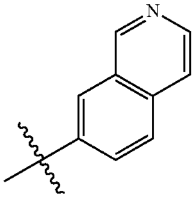
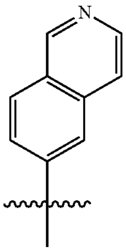
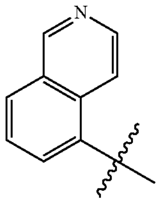
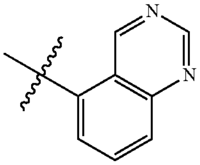
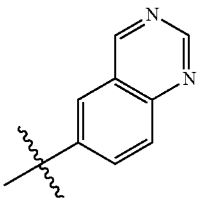
14
-continued
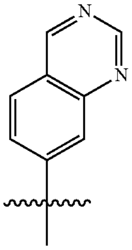
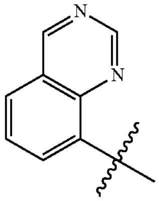
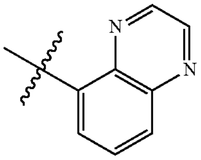
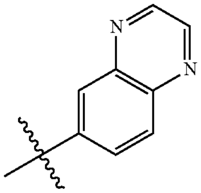
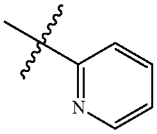
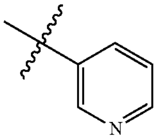
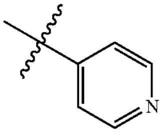
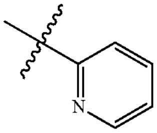
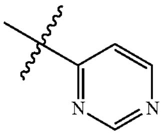
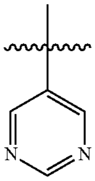
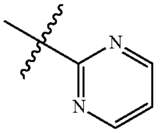
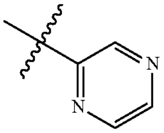
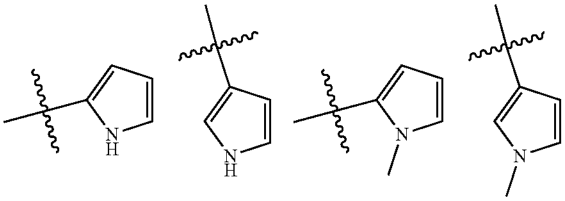
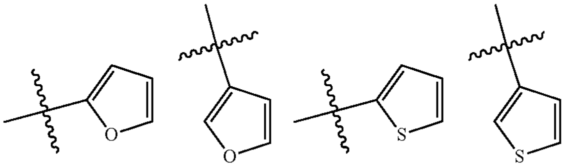
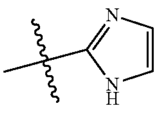
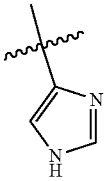

-continued

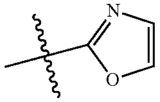 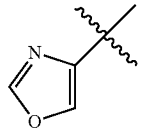 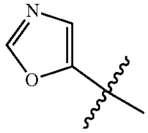

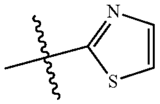 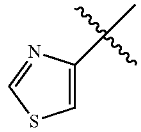 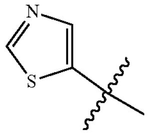

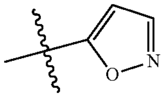 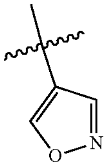 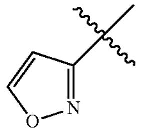

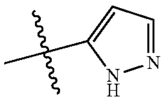 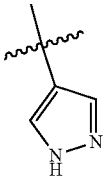 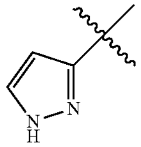

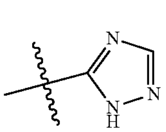 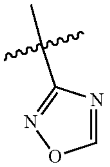 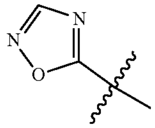

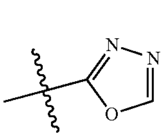 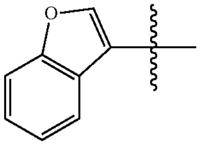

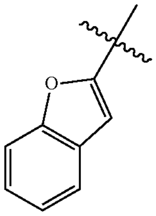 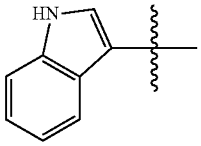 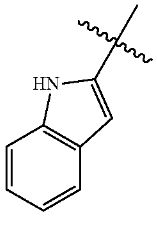

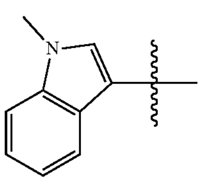 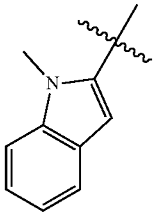

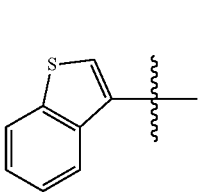 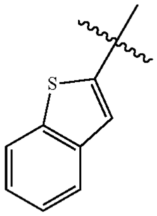

-continued

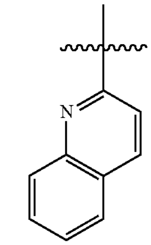 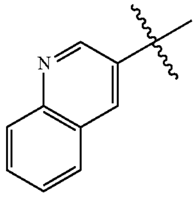

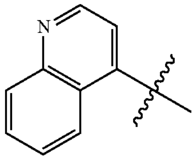 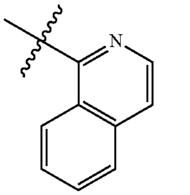

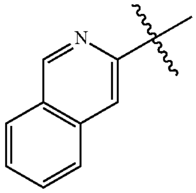 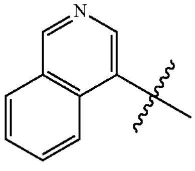

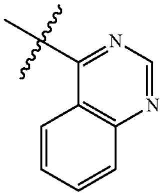 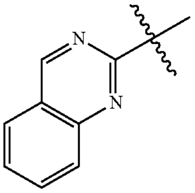

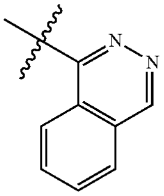 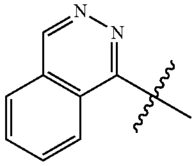

As used herein, the term "carbocycle" means a 5-, 6, or 7-membered, saturated or unsaturated cyclic ring, optionally containing O, S, or N atoms as part of the ring. Examples of carbocycles include, but are not limited to, cyclopentyl, cyclohexyl, cyclopenta-1,3-diene, phenyl, and any of the heterocycles recited above.

As used herein, the term, "compound" means all stereoisomers, tautomers, and isotopes of the compounds described herein.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the term "contacting" means bringing together of two compounds/atoms to form at least one covalent bond between the compounds or atoms.

As used herein, the term "coupling reagent" or "peptide coupling reagent" means a reagent that facilitate to form an amide bond between an amine and carboxylic acid including but not limited to carbodiimides, aminium/uronium and phosphonium salts, and propanephosphonic acid anhydride. For example, the coupling reagent is diisopropylcarbodiimide (DIC), dicyclohexylcarbodiimide (DCC), 1-Ethyl-3-(3-dimethylaminopropyl) carbodiimide (EDC, EDAC or EDCI), 1-[Bis(dimethylamino)methylene]-1H-1,2,3-triazolo[4,5-b]pyridinium 3-oxide hexafluorophosphate, Hexafluorophosphate Azabenzotriazole Tetramethyl Uronium (HATU), 2-(1H-benzotriazol-1-yl)-1,1,3,3-tetramethyluronium hexafluorophosphate, Hexafluorophosphate Benzotriazole Tetramethyl Uronium (HBTU), O-(1H-6-Chlorobenzotriazole-1-yl)-1,1,3,3-tetramethyluronium hexafluorophosphatO-(1H-6-Chlorobenzotriazole-1-yl)-1,1,3,3-tetramethyluronium hexafluorophosphate (HCTU), Benzotriazol-1-yloxy)tripyrrolidinophosphonium hexafluorophosphate (PyBOP), 7-Azabenzotriazol-1-yloxy)tripyrrolidinophosphonium hexafluorophosphate (PyAOP), Propanephosphonic acid anhydride (PPAA, T3P), or any combination thereof.

As used herein, the term "cyano" means —CN.

As used herein, the term "cycloalkyl" means non-aromatic cyclic hydrocarbons including cyclized alkyl, alkenyl, and alkynyl groups that contain up to 20 ring-forming carbon atoms. Cycloalkyl groups can include mono- or polycyclic ring systems such as fused ring systems, bridged ring systems, and spiro ring systems. In some embodiments, polycyclic ring systems include 2, 3, or 4 fused rings. A cycloalkyl group can contain from 3 to 15, from 3 to 10, from 3 to 8, from 3 to 6, from 4 to 6, from 3 to 5, or 5 or 6 ring-forming carbon atoms. Ring-forming carbon atoms of a cycloalkyl group can be optionally substituted by oxo or sulfido. Examples of cycloalkyl groups include, but are not limited to, cyclopropyl, cyclobutyl, cyclopentyl, cyclohexyl, cycloheptyl, cyclooctyl, cyclononyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (having a bond in common with) to the cycloalkyl ring, for example, benzo or thienyl derivatives of pentane, pentene, hexane, and the like (e.g., 2,3-dihydro-1H-indene-1-yl, or 1H-inden-2 (3H)-one-1-yl).

As used herein, the term "cycloheteroalkyl" means as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)n$ (where n is 0, 1, 2 or 3). The above groups may include 1 to 4 substituents such as alkyl, halo, oxo and/or any of the substituents for alkyl or aryl set out herein. In addition, any of the cycloheteroalkyl rings can be fused to a cycloalkyl, aryl, heteroaryl or cycloheteroalkyl ring.

As used herein, the terms "for example" and "such as," and grammatical equivalences thereof.

As used herein, the term "halo" means halogen groups including, but not limited to fluoro, chloro, bromo, and iodo.

As used herein, the term "haloalkoxy" means an —O-haloalkyl group. An example of an haloalkoxy group is $OCF_3$.

As used herein, the term "haloalkyl" means a $C_{1-6}$alkyl group having one or more halogen substituents. Examples of haloalkyl groups include, but are not limited to, $CF_3$, $C_2F_5$, $CH_2F$, $CHF_2$, $CCl_3$, $CHCl_2$, $CH_2CF_3$, and the like.

As used herein, the term "heteroaryl" means an aromatic heterocycle having up to 20 ring-forming atoms (e.g., C) and having at least one heteroatom ring member (ring-forming atom) such as sulfur, oxygen, or nitrogen. In some embodiments, the heteroaryl group has at least one or more heteroatom ring-forming atoms, each of which are, independently, sulfur, oxygen, or nitrogen. In some embodiments, the heteroaryl group has from 3 to 20 ring-forming atoms, from 3 to 10 ring-forming atoms, from 3 to 6 ring-forming atoms, or from 3 to 5 ring-forming atoms. In some embodiments, the heteroaryl group contains 2 to 14 carbon atoms, from 2 to 7 carbon atoms, or 5 or 6 carbon atoms. In some embodiments, the heteroaryl group has 1 to 4 heteroatoms, 1 to 3 heteroatoms, or 1 or 2 heteroatoms. Heteroaryl groups include monocyclic and polycyclic (e.g., having 2, 3 or 4 fused rings) systems. Examples of heteroaryl groups include, but are not limited to, pyridyl, pyrimidinyl, pyrazinyl, pyridazinyl, triazinyl, furyl, quinolyl, isoquinolyl, thienyl, imidazolyl, thiazolyl, indolyl (such as indol-3-yl), pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, pyranyl, oxadiazolyl, isoxazolyl, triazolyl, thianthrenyl, indolizinyl, isoindolyl, isobenzofuranyl, benzoxazolyl, xanthenyl, 2H-pyrrolyl, pyrrolyl, 3H-indolyl, 4H-quinolizinyl, phthalazinyl, naphthyridinyl, quinazolinyl, phenanthridinyl, acridinyl, perimidinyl, phenanthrolinyl, phenazinyl, isothiazolyl, phenothiazinyl, isoxazolyl, furanyl, phenoxazinyl groups, and the like. Suitable heteroaryl groups include 1,2,3-triazole, 1,2,4-triazole, 5-amino-1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, and 2-aminopyridine.

As used herein, the term "heterocycle" or "heterocyclic ring" means a 5- to 7-membered mono- or bicyclic or 7- to 10-membered bicyclic heterocyclic ring system any ring of which may be saturated or unsaturated, and which consists of carbon atoms and from one to three heteroatoms chosen from N, O and S, and wherein the N and S heteroatoms may optionally be oxidized, and the N heteroatom may optionally be quaternized, and including any bicyclic group in which any of the above-defined heterocyclic rings is fused to a benzene ring. Particularly useful are rings containing one oxygen or sulfur, one to three nitrogen atoms, or one oxygen or sulfur combined with one or two nitrogen atoms. The heterocyclic ring may be attached at any heteroatom or carbon atom which results in the creation of a stable structure. Examples of heterocyclic groups include, but are not limited to, piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

As used herein, the term "heterocycloalkyl" means non-aromatic heterocycles having up to 20 ring-forming atoms including cyclized alkyl, alkenyl, and alkynyl groups, where one or more of the ring-forming carbon atoms is replaced by a heteroatom such as an O, N, or S atom. Hetercycloalkyl groups can be mono or polycyclic (e.g., fused, bridged, or spiro systems). In some embodiments, the heterocycloalkyl group has from 1 to 20 carbon atoms or from 3 to 20 carbon atoms. In some embodiments, the heterocycloalkyl group contains 3 to 14 ring-forming atoms, 3 to 7 ring-forming atoms, or 5 or 6 ring-forming atoms. In some embodiments, the heterocycloalkyl group has 1 to 4 heteroatoms, 1 to 3 heteroatoms, or 1 or 2 heteroatoms. In some embodiments, the heterocycloalkyl group contains 0 to 3 double bonds. In some embodiments, the heterocycloalkyl group contains 0 to 2 triple bonds. Examples of heterocycloalkyl groups include, but are not limited to, morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, oxazolidinyl, isothiazolidinyl, pyrazolidinyl, thiazolidinyl, imidazolidinyl, pyrrolidin-2-one-3-yl, and the like. In addition, ring-forming carbon atoms and heteroatoms of a heterocycloalkyl group can be optionally substituted by oxo or sulfido. For example, a ring-forming S atom can be substituted by 1 or 2 oxo (form a S(O) or $S(O_2)$. For another example, a ring-forming C atom can be substituted by oxo (form carbonyl). Also included in the definition of heterocycloalkyl are moieties that have one or more aromatic rings fused (having a bond in common with) to the nonaromatic heterocyclic ring including, but not limited to, pyridinyl, thiophenyl, phthalimidyl, naphthalimidyl, and benzo derivatives of heterocycles such as indolene, isoindolene, 4,5,6,7-tetrahydrothieno[2,3-c]pyridine-5-yl, 5,6-dihydrothieno[2,3-c]pyridin-7(4H)-one-5-yl, isoindolin-1-one-3-yl, and 3,4-dihydroisoquinolin-1(2H)-one-3yl groups. Ring-forming carbon atoms and heteroatoms of the heterocycloalkyl group can be optionally substituted by oxo or sulfido.

As used herein, the term "heterocycloalkylalkyl" means a $C_{1-6}$ alkyl substituted by heterocycloalkyl.

As used herein, the term "hydroxy" or "hydroxyl" means an —OH group.

As used herein, the term "hydroxyalkyl" or "hydroxylalkyl" means an alkyl group substituted by a hydroxyl group. Examples of a hydroxylalkyl include, but are not limited to, $—CH_2OH$ and $—CH_2CH_2OH$.

As used herein, the term "patient." means any animal, including mammals, such as mice, rats, other rodents, rabbits, dogs, cats, swine, cattle, sheep, horses, or primates, such as humans.

As used herein, the term "isolating" means that separating the compounds described herein from other components of a synthetic organic chemical reaction mixture by conventional techniques, such as filtration.

As used herein, the term "mammal" means a rodent (i.e., a mouse, a rat, or a guinea pig), a monkey, a cat, a dog, a cow, a horse, a pig, or a human. In some embodiments, the mammal is a human.

As used herein, the term "nitro" means $—NO_2$.

As used herein, the term "n-membered", where n is an integer, typically describes the number of ring-forming atoms in a moiety, where the number of ring-forming atoms is n. For example, pyridine is an example of a 6-membered heteroaryl ring and thiophene is an example of a 5-membered heteroaryl ring.

As used herein, the phrase "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent groups, provided that the normal valency of the designated atom or moiety is not exceeded, and that the substitution results in a stable compound. For example, if a methyl group is optionally substituted, then 3 hydrogen atoms on the carbon atom can be replaced with substituent groups.

As used herein, the phrase "pharmaceutically acceptable" means those compounds, materials, compositions, and/or dosage forms which are, within the scope of sound medical judgment, suitable for use in contact with tissues of humans and animals. In some embodiments, "pharmaceutically acceptable" means approved by a regulatory agency of the Federal or a state government or listed in the U.S. Pharmacopeia or other generally recognized pharmacopeia for use in animals, and more particularly in humans.

In some embodiments, the salt of a compound described herein is a pharmaceutically acceptable salt thereof. As used herein, the phrase "pharmaceutically acceptable salt(s)," includes, but is not limited to, salts of acidic or basic groups. Compounds that are basic in nature are capable of forming a wide variety of salts with various inorganic and organic acids. Acids that may be used to prepare pharmaceutically acceptable acid addition salts of such basic compounds are those that form non-toxic acid addition salts, i.e., salts containing pharmacologically acceptable anions including, but not limited to, sulfuric, thiosulfuric, citric, maleic, acetic, oxalic, hydrochloride, hydrobromide, hydroiodide, nitrate, sulfate, bisulfate, bisulfite, phosphate, acid phosphate, isonicotinate, borate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, bicarbonate, malonate, mesylate, esylate, napsydisylate, tosylate, besylate, orthophoshate, trifluoroacetate, and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include, but are not limited to, alkali metal or alkaline earth metal salts and, particularly, calcium, magnesium, ammonium, sodium, lithium, zinc, potassium, and iron salts. The present embodiments also includes quaternary ammonium salts of the compounds described herein, where the compounds have one or more tertiary amine moiety.

As used herein, the term "phenyl" means $—C_6H_5$. A phenyl group can be unsubstituted or substituted with one, two, or three suitable substituents.

As used herein, the term "purified" means that when isolated, the isolate contains at least 90%, at least 95%, at least 98%, or at least 99% of a compound described herein by weight of the isolate.

As used herein, the phrase "quaternary ammonium salts" means derivatives of the disclosed compounds with one or more tertiary amine moieties wherein at least one of the tertiary amine moieties in the parent compound is modified by converting the tertiary amine moiety to a quaternary ammonium cation via alkylation (and the cations are balanced by anions such as $Cl^-$, $CH_3COO^-$, and $CF_3COO^-$), for example methylation or ethylation.

As used herein, the term "solution/suspension" means a liquid composition wherein a first portion of the active agent is present in solution and a second portion of the active agent is present in particulate form, in suspension in a liquid matrix.

As used herein, the term "solvent" means a usually liquid substance capable of dissolving or dispersing one or more other substances including water, inorganic nonaqueous solvent, and organic solvents. The term "inorganic nonaqueous solvent" means a solvent other than water, that is not an organic compound. Examples of the "inorganic nonaqueous solvent" include, but are not limited to: liquid ammonia, liquid sulfur dioxide, sulfuryl chloride and sulfuryl chloride fluoride, phosphoryl chloride, dinitrogen tetroxide, antimony trichloride, bromine pentafluoride, hydrogen fluoride, pure sulfuric acid and other inorganic acids. The term "organic solvent" means carbon-based solvent. Examples of the "organic solvent" include, but are not limited to: aromatic compounds, e.g., benzene and toluene, alcohols, e.g., methanol, ethanol, and propanol, esters, ethers, ketones, e.g., acetone, amines, and nitrated and halogenated hydrocarbons. The "organic solvent" includes both polar and non-polar organic solvent. The "polar organic solvent" means an organic solvent that has large dipole moments (aka "partial charges") and in general the organic solvent with dielectric constants greater than about 5 is considered as "polar organic solvent" while those with dielectric constants less than 5 are considered "non-polar organic solvent." Examples of the "polar organic solvent" include, but are not limited to, acetic acid, methanol, acetone, and acetonitrile, DMSO, and DMF. Examples of the non-polar organic solvent include, but are not limited to, benzene, carbon tetrachloride, and n-hexane. The "organic solvent" includes both protonic and non-protonic organic solvent. The term "protonic organic solvent" means an organic solvent having a hydrogen atom bonded to oxygen or nitrogen (an acidic hydrogen atom). Examples of the "protonic organic solvent" include, but are not limited to, methanol, ethanol, propanol, isopropanol, butanol, hexanol, phenol, acetic acid, benzoic acid and partly fluorinated compounds thereof. Examples of the "non-protonic organic solvent" or "non-protonic solvent" include, but are not limited to: 2-methyl-tetrahydrofuran, tetrahydrofuran, acetonitrile, acetone, dicholoromethane, chloroform, ethyl acetate, diethylether, tert-butylmethylether, and N,N-Dimethylformamide.

As used herein, the phrase "substantially isolated" means a compound that is at least partially or substantially separated from the environment in which it is formed or detected.

As used herein, the phrase "suitable substituent" or "substituent" means a group that does not nullify the synthetic or pharmaceutical utility of the compounds described herein or the intermediates useful for preparing them. Examples of suitable substituents include, but are not limited to: $C_1$-$C_6$alkyl, $C_1$-$C_6$alkenyl, $C_1$-$C_6$alkynyl, $C_5$-$C_6$aryl, $C_1$-$C_6$alkoxy, $C_3$-$C_5$heteroaryl, $C_3$-$C_6$cycloalkyl, $C_5$-$C_6$aryloxy, —CN, —OH, oxo, halo, haloalkyl, —$NO_2$, —$CO_2H$, —$NH_2$, —NH($C_1$-$C_8$alkyl), —N($C_1$-$C_8$alkyl)$_2$, —NH($C_6$aryl), —N($C_5$-$C_6$aryl)$_2$, —CHO, —CO($C_1$-$C_6$alkyl), —CO(($C_5$-$C_6$aryl), —$CO_2$(($C_1$-$C_6$)alkyl), and —$CO_2$(($C_5$-$C_6$)aryl). One of skill in art can readily choose a suitable substituent based on the stability and pharmacological and synthetic activity of the compounds described herein.

As used herein, the term "and without limitation" is understood to follow unless explicitly stated otherwise.

At various places in the present specification, substituents of compounds may be disclosed in groups or in ranges. It is specifically intended that embodiments include each and every individual subcombination of the members of such groups and ranges. For example, the term "$C_1$-$C_6$ alkyl" is specifically intended to individually disclose methyl, ethyl, propyl, $C_4$ alkyl, $C_5$ alkyl, and $C_6$ alkyl.

For compounds in which a variable appears more than once, each variable can be a different moiety selected from the Markush group defining the variable. For example, where a structure is described having two R groups that are simultaneously present on the same compound, the two R groups can represent different moieties selected from the Markush groups defined for R. In another example, when an optionally multiple substituent is designated in the form, for example,

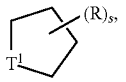

then it is understood that substituent R can occur s number of times on the ring, and R can be a different moiety at each occurrence. In the above example, where the variable $T^1$ is defined to include hydrogens, such as when $T^1$ is $CH_2$, NH, etc., any H can be replaced with a substituent.

It is further appreciated that certain features described herein, which are, for clarity, described in the context of separate embodiments, can also be provided in combination in a single embodiment. Conversely, various features, which are, for brevity, described in the context of a single embodiment, can also be provided separately or in any suitable subcombination.

It is understood that the present embodiments encompasses the process, where applicable, of stereoisomers, diastereomers and optical stereoisomers of the compounds, as well as mixtures thereof. Additionally, it is understood that stereoisomers, diastereomers, and optical stereoisomers of the compounds, and mixtures thereof, are within the scope of the embodiments. By way of non-limiting example, the mixture may be a racemate or the mixture may comprise unequal proportions of one particular stereoisomer over the other. Additionally, the compounds can be provided as a substantially pure stereoisomers, diastereomers and optical stereoisomers (such as epimers).

The compounds described herein can be asymmetric (e.g., having one or more stereocenters). All stereoisomers, such as enantiomers and diastereomers, are intended to be included within the scope of the embodiments unless otherwise indicated. Compounds that contain asymmetrically substituted carbon atoms can be isolated in optically active or racemic forms. Methods of preparation of optically active forms from optically active starting materials are known in the art, such as by resolution of racemic mixtures or by stereoselective synthesis. Many geometric isomers of olefins, C═N double bonds, and the like can also be present in the compounds described herein, and all such stable isomers are provided herein. Cis and trans geometric isomers of the compounds are also included within the present embodiments and can be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

In some embodiments, the composition comprises a compound, or a pharmaceutically acceptable salt thereof, that is at least 90%, at least 95%, at least 98%, or at least 99%, or 100% enantiomeric pure, which means that the ratio of one enantiomer to the other in the composition is at least 90:1 at least 95:1, at least 98:1, or at least 99:1, or is completely in the form of one enantiomer over the other.

Resolution of racemic mixtures of compounds can be carried out by any of numerous methods known in the art, including, for example, chiral HPLC, fractional recrystallization using a chiral resolving acid, which is an optically active, salt-forming organic acid. Suitable resolving agents for fractional recrystallization methods include, but are not limited to, optically active acids, such as the D and L forms of tartaric acid, diacetyltartaric acid, dibenzoyltartaric acid, mandelic acid, malic acid, lactic acid, and the various optically active camphorsulfonic acids such as β-camphorsulfonic acid. Other resolving agents suitable for fractional crystallization methods include, but are not limited to, stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent compositions can be determined by one skilled in the art.

Compounds may also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Examples of prototropic tautomers include, but are not limited to, ketone-enol pairs, amide-imidic acid pairs, lactam-lactim pairs, amide-imidic acid pairs, enamine-imine pairs, and annular forms where a proton can occupy two or more positions of a heterocyclic system including, but not limited to, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds also include hydrates and solvates, as well as anhydrous and non-solvated forms.

Compounds can also include all isotopes of atoms occurring in the intermediates or final compounds. Isotopes include those atoms having the same atomic number but different mass numbers. For example, isotopes of hydrogen include tritium and deuterium.

In some embodiments, the compounds, or salts thereof, are substantially isolated. Partial separation can include, for example, a composition enriched in the compound. Substantial separation can include compositions containing at least about 50%, at least about 60%, at least about 70%, at least about 80%, at least about 90%, at least about 95%, at least about 97%, or at least about 99% by weight of the compound, or salt thereof. Methods for isolating compounds and their salts are routine in the art.

Although the disclosed compounds are suitable, other functional groups can be incorporated into the compound with an expectation of similar results. In particular, thioamides and thioesters are anticipated to have very similar properties. The distance between aromatic rings can impact the geometrical pattern of the compound and this distance can be altered by incorporating aliphatic chains of varying length, which can be optionally substituted or can comprise an amino acid, a dicarboxylic acid or a diamine. The distance between and the relative orientation of monomers within the compounds can also be altered by replacing the amide bond with a surrogate having additional atoms. Thus, replacing a carbonyl group with a dicarbonyl alters the distance between the monomers and the propensity of dicarbonyl unit to adopt an anti-arrangement of the two carbonyl moiety and alter the periodicity of the compound. Pyromellitic anhydride represents still another alternative to simple amide linkages which can alter the conformation and physical properties of the compound. Modern methods of solid phase organic chemistry (E. Atherton and R. C. Sheppard, Solid Phase Peptide Synthesis A Practical Approach IRL Press Oxford 1989) now allow the synthesis of homodisperse compounds with molecular weights approaching 5,000 Daltons. Other substitution patterns are equally effective.

Embodiments of various processes of preparing compounds of Formula (I) and salts thereof are provided. Where a variable is not specifically recited, the variable can be any option described herein, except as otherwise noted or dictated by context.

In some embodiments, the processes of preparing compounds of formula (I) or a pharmaceutically acceptable salt thereof is as described in the appended exemplary, non-limiting claims.

In some embodiments, processes or methods of preparing compounds of Formula (I), or a pharmaceutically acceptable salt thereof are provided. In some embodiments, the methods comprise: contacting a compound of Formula (II)

Formula (II)

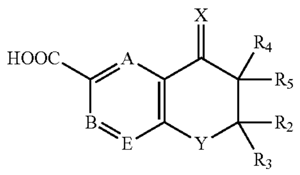

With a compound of Formula (III)

Formula (III)

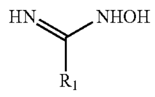

under suitable conditions to form a compound having the structure of

Formula (I)

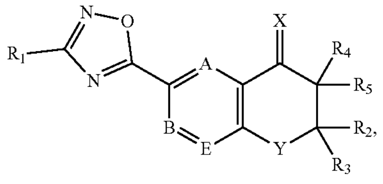

wherein:

A, B, and E are each independently N or $CR_6$;

X and Y are each independently O, S, or $NR_7$;

$R_1$ is H, OH, $NH_2$, $NO_2$, optionally substituted carbocycle, optionally substituted aryl group, optionally substituted heteroaryl group, branched or unbranched alkyl alcohol, halo, branched or unbranched alkyl, amide, cyano, alkoxy, haloalkyl, aklylsulfonyl, nitrite, or alkylsulfanyl; and $R_2$, $R_3$, $R_4$, $R_5$, $R_6$, and $R_7$, are each independently H, optionally substituted $C_1$-$C_6$ alkyl, optionally substituted $C_1$-$C_6$ hydroxyalkyl, optionally substituted $C_1$-$C_6$ alkoxy, optionally substituted cycloalkyl, or optionally substituted cycloheteroalkyl; $R_2$ and $R_3$ are together optionally substituted cycloalkyl, or optionally substituted cycloheteroalkyl; or $R_4$ and $R_5$ are together optionally substituted cycloalkyl, or optionally substituted cycloheteroalkyl.

In some embodiments, provided are processes of preparing compounds of Formula (I), or a pharmaceutically acceptable salt thereof, wherein the contacting is reacting. In some embodiments, the contacting is condensing. In some embodiments, the contacting is coupling. In some embodiments, the contacting is cyclizing.

In some embodiments, provided are processes of preparing compounds of Formula (I), or a pharmaceutically acceptable salt thereof, wherein A is N or $CR_6$. In some embodiments, A is N. In some embodiments, A is $CR_6$.

In some embodiments, provided are processes of preparing compounds of Formula (I), or a pharmaceutically acceptable salt thereof, wherein B is N or $CR_6$. In some embodiments, B is N. In some embodiments, B is $CR_6$.

In some embodiments, provided are processes of preparing compounds of Formula (I), or a pharmaceutically acceptable salt thereof, wherein E is N or $CR_6$. In some embodiments, E is N. In some embodiments, E is $CR_6$.

In some embodiments, provided are processes of preparing compounds of Formula (I), or a pharmaceutically acceptable salt thereof, wherein X is O, S, or $NR_7$. In some embodiments, X is O. In some embodiments, X is S. In some embodiments, X is $NR_7$.

In some embodiments, provided are processes of preparing compounds of Formula (I), or a pharmaceutically acceptable salt thereof, wherein Y is O, S, or $NR_7$. In some embodiments, Y is O. In some embodiments, Y is S. In some embodiments, Y is $NR_7$.

In some embodiments, provided are processes of preparing compounds of Formula (I), or a pharmaceutically acceptable salt thereof, wherein $R_1$ is H, OH, $NH_2$, $NO_2$, optionally substituted carbocycle, optionally substituted aryl group, optionally substituted heteroaryl group, branched or unbranched alkyl alcohol, halo, branched or unbranched alkyl, amide, cyano, alkoxy, haloalkyl, aklylsulfonyl, nitrite, or alkylsulfanyl. In some embodiments, $R_1$ is H. In some embodiments, $R_1$ is OH. In some embodiments, $R_1$ is $NH_2$. In some embodiments, $R_1$ is $NO_2$. In some embodiments. $R_1$ is optionally substituted carbocycle. In some embodiments, $R_1$ is optionally substituted aryl group. In some embodiments. $R_1$ is optionally substituted heteroaryl group. In some embodiments, $R_1$ is branched or unbranched alkyl alcohol. In some embodiments, $R_1$ is halo. In some embodiments, $R_1$ is branched or unbranched alkyl. In some embodiments, $R_1$ is amide. In some embodiments, $R_1$ is cyano. In some embodiments, $R_1$ is alkoxy. In some embodiments, $R_1$ is haloalkyl. In some embodiments, $R_1$ is aklylsulfonyl. In some embodiments, $R_1$ is nitrite. In some embodiments. $R_1$ is alkylsulfanyl.

In some embodiments, $R_2$ is H, optionally substituted $C_1$-$C_6$ alkyl, optionally substituted $C_1$-$C_6$ hydroxyalkyl, optionally substituted $C_1$-$C_6$ alkoxy, optionally substituted cycloalkyl, or optionally substituted cycloheteroalkyl. In some embodiments, $R_2$ is H. In some embodiments, $R_2$ is optionally substituted $C_1$-$C_6$ alkyl. In some embodiments, $R_2$ is optionally substituted $C_1$-$C_6$ hydroxyalkyl. In some embodiments, $R_2$ is optionally substituted $C_1$-$C_6$ alkoxy. In some embodiments, $R_2$ is optionally substituted cycloalkyl. In some embodiments, $R_2$ is optionally substituted cycloheteroalkyl.

In some embodiments, provided are processes of preparing compounds of Formula (I), or a pharmaceutically acceptable salt thereof, wherein $R_3$ is H, optionally substituted $C_1$-$C_6$ alkyl, optionally substituted $C_1$-$C_6$ hydroxyalkyl, optionally substituted $C_1$-$C_6$ alkoxy, optionally substituted cycloalkyl, or optionally substituted cycloheteroalkyl. In some embodiments, $R_3$ is H. In some embodiments. $R_3$ is optionally substituted $C_1$-$C_6$ alkyl. In some embodiments, $R_3$ is optionally substituted $C_1$-$C_6$ hydroxyalkyl. In some embodiments. $R_3$ is optionally substituted $C_1$-$C_6$ alkoxy. In some embodiments. $R_3$ is optionally substituted cycloalkyl. In some embodiments, $R_3$ is optionally substituted cycloheteroalkyl.

In some embodiments, provided are processes of preparing compounds of Formula (I), or a pharmaceutically acceptable salt thereof, wherein $R_4$ is H, optionally substituted $C_1$-$C_6$ alkyl, optionally substituted $C_1$-$C_6$ hydroxyalkyl, optionally substituted $C_1$-$C_6$ alkoxy, optionally substituted cycloalkyl, or optionally substituted cycloheteroalkyl. In some embodiments, $R_4$ is H. In some embodiments, $R_4$ is optionally substituted $C_1$-$C_6$ alkyl. In some embodiments, $R_4$ is optionally substituted $C_1$-$C_6$ hydroxyalkyl. In some embodiments, $R_4$ is optionally substituted $C_1$-$C_6$ alkoxy. In some embodiments. $R_4$ is optionally substituted cycloalkyl. In some embodiments, $R_4$ is optionally substituted cycloheteroalkyl.

In some embodiments, provided are processes of preparing compounds of Formula (I), or a pharmaceutically acceptable salt thereof, wherein $R_5$ is H, optionally substituted $C_1$-$C_6$ alkyl, optionally substituted $C_1$-$C_6$ hydroxyalkyl, optionally substituted $C_1$-$C_6$ alkoxy, optionally substituted cycloalkyl, or optionally substituted cycloheteroalkyl. In some embodiments, $R_5$ is H. In some embodiments, $R_5$ is optionally substituted $C_1$-$C_6$ alkyl. In some embodiments, $R_5$ is optionally substituted $C_1$-$C_6$ hydroxyalkyl. In some embodiments, $R_5$ is optionally substituted $C_1$-$C_6$ alkoxy. In some embodiments, $R_5$ is optionally substituted cycloalkyl. In some embodiments, $R_5$ is optionally substituted cycloheteroalkyl.

In some embodiments, provided are processes of preparing compounds of Formula (I), or a pharmaceutically acceptable salt thereof, wherein $R_6$ is H, optionally substituted $C_1$-$C_6$ alkyl, optionally substituted $C_1$-$C_6$ hydroxyalkyl, optionally substituted $C_1$-$C_6$ alkoxy, optionally substituted cycloalkyl, or optionally substituted cycloheteroalkyl. In some embodiments, $R_6$ is H. In some embodiments, $R_6$ is optionally substituted $C_1$-$C_6$ alkyl. In some embodiments, $R_6$ is optionally substituted $C_1$-$C_6$ hydroxyalkyl. In some embodiments. $R_6$ is optionally substituted $C_1$-$C_6$ alkoxy. In some embodiments, $R_6$ is optionally substituted cycloalkyl. In some embodiments, $R_6$ is optionally substituted cycloheteroalkyl.

In some embodiments, $R_7$ is H, optionally substituted $C_1$-$C_6$ alkyl, optionally substituted $C_1$-$C_6$ hydroxyalkyl, optionally substituted $C_1$-$C_6$ alkoxy, optionally substituted cycloalkyl, or optionally substituted cycloheteroalkyl. In some embodiments, $R_7$ is H. In some embodiments, $R_7$ is optionally substituted $C_1$-$C_6$ alkyl. In some embodiments, $R_7$ is optionally substituted $C_1$-$C_6$ hydroxyalkyl. In some embodiments, $R_7$ is optionally substituted $C_1$-$C_6$ alkoxy. In some embodiments, $R_7$ is optionally substituted cycloalkyl. In some embodiments, $R_7$ is optionally substituted cycloheteroalkyl.

In some embodiments, provided are processes of preparing compounds of Formula (I), or a pharmaceutically acceptable salt thereof, wherein $R_2$ and $R_3$ are together optionally substituted cycloalkyl, or optionally substituted cycloheteroalkyl. In some embodiments, $R_2$ and $R_3$ are together optionally substituted cycloalkyl. In some embodiments, $R_2$ and $R_3$ are together optionally substituted cycloheteroalkyl.

In some embodiments, $R_4$ and $R_5$ are together optionally substituted cycloalkyl, or optionally substituted cycloheteroalkyl. In some embodiments, $R_4$ and $R_5$ are together optionally substituted cycloalkyl. In some embodiments, $R_4$ and $R_5$ are together optionally substituted cycloheteroalkyl.

In some embodiments, processes of preparing compounds of Formula (I), or a pharmaceutically acceptable salt thereof further comprise coupling the compound of Formula (II)

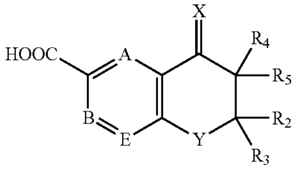

with the compound of

Formula (III)

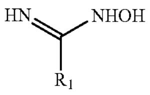

to form compounds of

Formula (I)

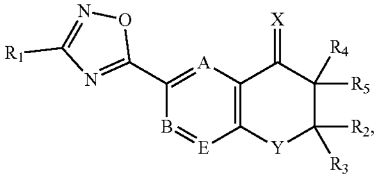

or a pharmaceutically acceptable salt thereof.

In some embodiments, provided are processes of preparing compounds of Formula (I), or a pharmaceutically acceptable salt thereof, wherein the coupling comprises reacting the compounds of Formula (II) and Formula (III) for at least about 5 minutes. In some embodiments, the reacting comprises heating the reaction to a temperature of at least about 40° C. for at least about 1, 2, 3, 4, or 5 minutes.

In some embodiments, processes of preparing compounds of Formula (I), or a pharmaceutically acceptable salt thereof further comprise quenching the reaction of a compound of Formula (II) and a compound of Formula (III) to form a slurry comprising the compound of Formula (I)

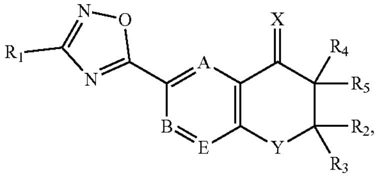

or a pharmaceutically acceptable salt thereof. In some embodiments, the quenching comprises cooling and/or adding water to the reaction of a compound of Formula (II) and a compound of Formula (III) to quench the reaction to form the slurry.

In some embodiments, processes of preparing compounds of Formula (I), or a pharmaceutically acceptable salt thereof further comprise isolating the compound of Formula (I)

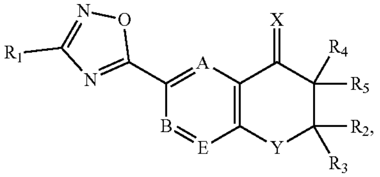

or a pharmaceutically acceptable salt thereof. In some embodiments, the isolating comprises filtering, washing, and/or drying the slurry to obtain the compound of Formula (I)

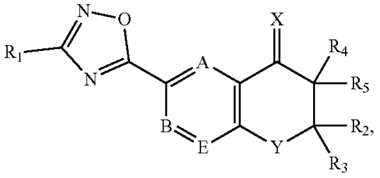

or a pharmaceutically acceptable salt thereof.

In some embodiments, the isolating comprises filtering the slurry to obtain the compound of Formula (I)

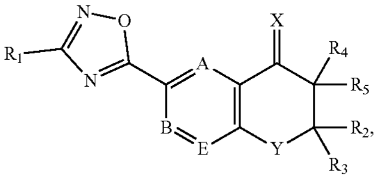

or a pharmaceutically acceptable salt thereof. In some embodiments, the isolating comprises washing the slurry to obtain the compound of Formula (I)

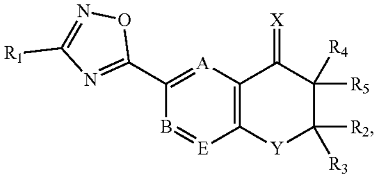

or a pharmaceutically acceptable salt thereof. In some embodiments, the isolating comprises drying the slurry to obtain the compound of Formula (I)

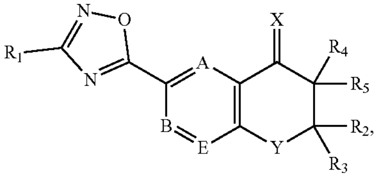

or a pharmaceutically acceptable salt thereof. In some embodiments, the isolating comprises filtering and drying the slurry to obtain the compound of Formula (I)

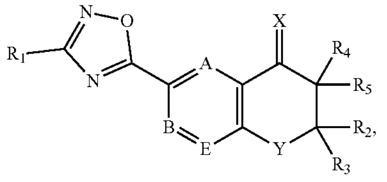

or a pharmaceutically acceptable salt thereof. In some embodiments, the isolating comprises filtering and washing the slurry to obtain the compound of Formula (I)

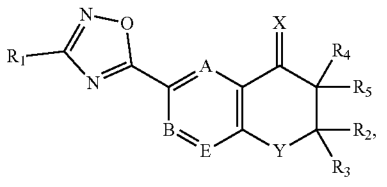

or a pharmaceutically acceptable salt thereof. In some embodiments, the isolating comprises washing and drying the slurry to obtain the compound of Formula (I)

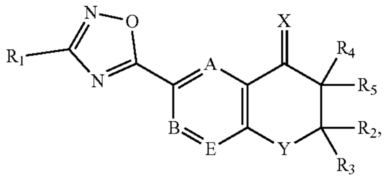

or a pharmaceutically acceptable salt thereof. In some embodiments, the isolating comprises filtering, washing, and drying the slurry to obtain the compound of Formula (I)

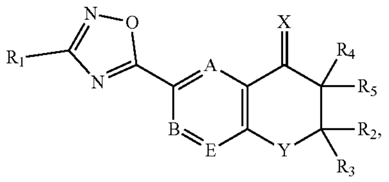

or a pharmaceutically acceptable salt thereof.

In some embodiments, provided are processes of preparing compounds of Formula (I), or a pharmaceutically acceptable salt thereof comprise washing to obtain the compound of Formula (I)

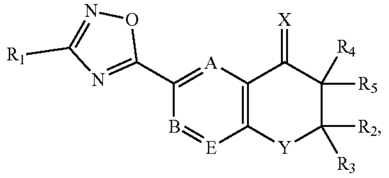

or a pharmaceutically acceptable salt thereof, wherein the washing comprises washing with water and/or an organic solvent. In some embodiments, the washing comprise washing with solvents to remove impurities such as unreacted or excess the compound of Formula (II) or the compound of Formula (III), the byproducts derived from the coupling regent and/or additives, and any combination thereof. In some embodiments, the washing comprise washing with water. In some embodiments, the washing comprise washing with an organic solvent. In some embodiments, the washing comprise washing with water and an organic solvent. In some embodiments, the washing does not comprise washing with water. In some embodiments, the washing does not comprise washing with an organic solvent.

In some embodies, provided are processes of preparing compounds of Formula (I), or a pharmaceutically acceptable salt thereof comprising the steps of:

(a) adding a coupling reagent and optionally an additive to a solution of a compound of Formula (II)

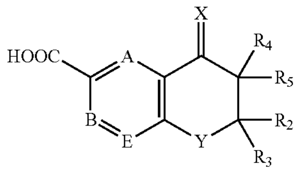

in a first organic solvent to form a mixture and stirring the mixture for at least about 5 minutes;

Formula (III)

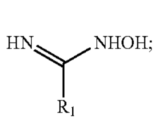

(b) stirring the mixture of step (a) with a compound of (c) heating the mixture of step (b) to a temperature of at least about 40° C. and stirring the mixture under the temperature;

(d) cooling the mixture of step (c) and adding water to the mixture to form a slurry;

(e) stirring the slurry of step (d);

(f) filtering the slurry of step (e) to obtain a solid;

(g) washing the solid of the step (f) with water and/or a second organic solvent; and (h) drying the solid of the step (g) at a temperature of at least about 30° C. under vacuum to form the compound of Formula (I)

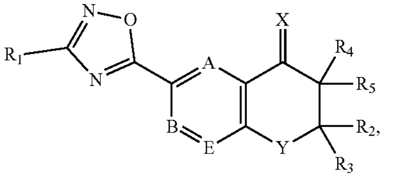

wherein the variables are defined herein.

In some embodiments, provided are processes of preparing compounds of Formula (I), or a pharmaceutically acceptable salt thereof, wherein the coupling reagent is a carbodiimide. In some embodiments, the carbodiimide is DCC, DIC, or EDC hydrochloride. In some embodiments, the carbodiimide is DCC. In some embodiments, the carbodiimide is DIC. In some embodiments, the coupling reagent is EDC hydrochloride.

In some embodiments, provided are processes of preparing compounds of Formula (I), or a pharmaceutically acceptable salt thereof, wherein the additive is HOBt, HOAt, or ethyl cyanohydroxyiminoacetate. In some embodiments, the additive is HOBt. In some embodiments, the additive is HOAt. In some embodiments, the additive is ethyl cyanohydroxyiminoacetate.

In some embodiments, provided are processes of preparing compounds of Formula (I), or a pharmaceutically acceptable salt thereof, wherein the first organic solvent is a polar organic solvent. In some embodiments, wherein the polar organic solvent is a polar non-protonic organic solvent. In some embodiments, the polar non-protonic organic solvent is dimethylformamide or diethylformamide. In some embodiments, the polar non-protonic organic solvent is diethylformamide. In some embodiments, the polar non-protonic organic solvent is dimethylformamide.

In some embodiments, provided are processes of preparing compounds of Formula (I), or a pharmaceutically acceptable salt thereof, wherein the amount of the coupling reagent is at least about 1.0 equivalent in molar ratio to the amount of the compound of Formula (II). In some embodiments, the amount of the coupling reagent is about 1.2 equivalent in molar ratio to the amount of the compound of Formula (II). In some embodiments, the amount of the additive is at least about 1.0 equivalent in molar ratio to the amount of the compound of Formula (II). In some embodiments, the amount of the additive is about 1.0 equivalent in molar ratio to the amount of the compound of Formula (II).

In some embodiments, provided are processes of preparing compounds of Formula (I), or a pharmaceutically acceptable salt thereof, wherein the concentration of the compound of Formula (II) in the first organic solvent is at least about 0.1 mol/L. In some embodiments, the concentration of the compound of Formula (II) in the first organic solvent is about 0.8 mol/L.

In some embodiments, provided are processes of preparing compounds of Formula (I), or a pharmaceutically acceptable salt thereof, wherein in the step (a), the mixture is stirred for at least about 5 minutes. In some embodiments, in the step (a), the mixture is stirred for about 1 hour.

In some embodiments, provided are processes of preparing compounds of Formula (I), or a pharmaceutically acceptable salt thereof, wherein the amount of the compound of Formula (III) is at least about 1.0 equivalent in molar ratio to the amount of the compound of Formula (II). In some embodiments, the amount of the compound of Formula (III) is about 1.2 equivalent in molar ratio to the amount of the compound of Formula (II).

In some embodiments, in the step (b), the mixture is stirred for at least 5 minutes. In some embodiments, in the step (b), the mixture is stirred for at least about 1 hour.

In some embodiments, in the step (c), the temperature is at least about 60° C. In some embodiments, in the step (c), the temperature is at least about 75° C. In some embodiments, in the step (c), the temperature is about 95° C. In some embodiments, in the step (c), the mixture of step (a) is heated to between about 90° C. and about 95° C. In some embodiments, in the step (c), the mixture of step (a) is heated to between about 85° C. and about 95° C. In some embodiments, in the step (c), the mixture of step (a) is heated to between about 80° C. and about 95° C. In some embodiments, in the step (c), the mixture of step (a) is heated to between about 75° C. and about 95° C. In some embodiments, in the step (c), the mixture of step (a) is heated to between about 95° C. and about 100° C. In some embodiments, in the step (c), the mixture of step (a) is heated to between about 95° C. and about 105° C. In some embodiments, in the step (c), the mixture of step (a) is heated to between about 95° C. and about 110° C. In some embodiments, in the step (c), the mixture of step (a) is heated to between about 90° C. and about 115° C.

In some embodiments, processes of preparing compounds of Formula (I), or a pharmaceutically acceptable salt thereof, wherein in the step (c), the mixture is stirred at the temperature for at least about 1, 2, 3, 4, or 5 minutes. In some embodiments, in the step (c), the mixture is stirred at the temperature for at least about 1 hour. In some embodiments, in the step (c), the mixture is stirred at the temperature for about 5 hours. In some embodiments, in the step (c), the mixture is stirred at the temperature for about 18 hours.

In some embodiments, provided are processes of preparing compounds of Formula (I), or a pharmaceutically acceptable salt thereof, wherein in the step (d), the mixture is cooled to about 5-25° C. I. In some embodiments, in the step (d), the mixture is cooled to about 15-20° C.

In some embodiments, in the step (d), the volume ratio of water to the first organic solvent is at least about 1. In some embodiments, in the step (d), the volume ratio of water to the first organic solvent is about 2.

In some embodiments, in the step (e), the mixture is stirred at about 5-25° C. I. In some embodiments, in the step (e), the mixture is stirred at about 15-20° C.

In some embodiments, in the step (e), the slurry is stirred for at least about 5 minutes. In some embodiments, in the step (e), the slurry is stirred for about 1 hour.

In some embodiments, provided are processes of preparing compounds of Formula (I), wherein in the step (g), the volume ratio of water to the first organic solvent in each wash cycle is at least about 0.5. In some embodiments, in the step (g), the volume ratio of water to the first organic solvent in each wash cycle is about 0.5.

In some embodiments, provided are processes of preparing compounds of Formula (I), or a pharmaceutically acceptable salt thereof, wherein the solid is washed with water at least once. In some embodiments, the solid is washed with water twice.

In some embodiments, provided are processes of preparing compounds of Formula (I), or a pharmaceutically acceptable salt thereof, wherein the volume ratio of the second organic solvent to the first organic solvent in each wash cycle is at least about 0.5. In some embodiments, the volume ratio of the second organic solvent to the first organic solvent in each wash cycle is about 0.5.

In some embodiments, provided are processes of preparing compounds of Formula (I), or a pharmaceutically acceptable salt thereof, wherein the solid is washed with the second organic solvent at least once. In some embodiments, the solid is washed with the second organic solvent twice.

In some embodiments, provided are processes of preparing compounds of Formula (I), or a pharmaceutically acceptable salt thereof, wherein the second organic solvent is an ether. In some embodiments, the ether is a dialkyl ether. In some embodiments, the ether is methyl-tert-butyl ether.

In some embodiments, provided are processes of preparing compounds of Formula (I), or a pharmaceutically acceptable salt thereof, wherein the solid is dried at about 55° C. In some embodiments, the solid is dried between about 45° C. to about 55° C. In some embodiments, the solid is dried between about 55° C. to about 65° C. In some embodiments, the solid is dried between about 50° C. to about 60° C.

In some embodiments, also provided are processes of preparing compounds of Formula (I), or a pharmaceutically acceptable salt thereof comprising the steps of:

(a) adding EDC hydrochloride and ethyl cyanohydroxyiminoacetate to a solution of a compound of Formula (II)

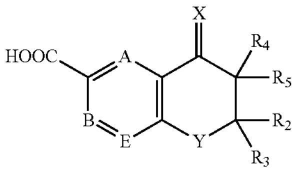

in dimethylformamide to form a mixture and stirring the mixture for at least about 1 hour;

Formula (III)

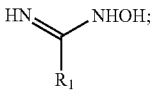

(b) stirring the mixture of the step (a) with a compound of (c) heating the mixture of the step (b) to a temperature at about 95° C. and stirring the mixture under the temperature for at least about 5 hour;

(d) cooling the mixture of the step (c) to about 15-20° C. and adding water to form a slurry;

(e) stirring the slurry of the step (d) at about 15-20° C. for about 1 h;

(f) filtering the slurry of the step (e) to from a solid;

(g) washing the solid of the step (f) with water and methyl-tert-butyl ether; and (h) drying the solid of the step (g) at about 55° C. under vacuum to form the compound of Formula (I)

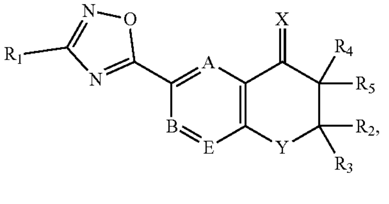

wherein the variables are as defined herein.

In some embodiments, provided are processes of preparing compounds of Formula (I), or a pharmaceutically acceptable salt thereof, wherein, in the step (c), the mixture of step (b) is heated to or close to reflux. In some embodiments, in the step (c), the mixture of step (b) is heated to about 95° C. In some embodiments, in the step (c), in the step (c), the mixture of step (b) is heated to between about 90° C. and about 95° C. In some embodiments, in the step (c), the mixture of step (b) is heated to between about 85° C. and about 95° C. In some embodiments, in the step (c), the mixture of step (b) is heated to between about 80° C. and about 95° C. In some embodiments, in the step (c), the mixture of step (b) is heated to between about 75° C. and about 95° C. In some embodiments, in the step (c), the mixture of step (b) is heated to between about 95° C. and about 100° C. In some embodiments, in the step (c), the mixture of step (b) is heated to between about 95° C. and about 105° C. In some embodiments, the mixture of step (b) is heated to between about 95° C. and about 110° C. In some embodiments, the mixture of step (b) is heated to between about 90° C. and about 115° C.

In some embodiments, processes of preparing compounds of Formula (I), or a pharmaceutically acceptable salt thereof, further comprise recrystallizing the solid of the step (h) from a solvent. In some embodiments, the solvent for recrystallization is water, dimethylformadimade, ethanol, or methyl-tert-butyl ether. In some embodiments, the solvent for recrystallization is ethanol. In some embodiments, when the solvent for recrystallization is ethanol or methyl-tert-butyl ether, the mixture forms a slurry.

In some embodiments, provided are processes of preparing compounds of Formula (I), or a pharmaceutically acceptable salt thereof, wherein when the solvent for recrystallization is ethanol, the slurry is heated to a temperature of at least about 50° C. In some embodiments, when the solvent is ethanol, the slurry is heated to a temperature of about 75° C. In some embodiments, the slurry is stirred at about 75° C. for about 15 hours.

In some embodiments, when the solvent is methyl-tert-butyl ether, the slurry is heated to a temperature of at least about 30° C. In some embodiments, when the solvent is methyl-tert-butyl ether, the slurry is heated to a temperature of about 45° C. In some embodiments, the slurry is stirred at about 45° C. for about 15 hours.

In some embodiments, provided are processes of preparing compounds of Formula (I), or a pharmaceutically acceptable salt thereof, wherein the purity of the recrystallized solid is at least about 95%. In some embodiments, the purity of the recrystallized solid is at least about 99%. In some embodiments, the purity of the recrystallized solid is at about 99.5%.

In some embodiments, provided are processes of preparing compounds of Formula (I), or a pharmaceutically acceptable salt thereof, wherein the color of the recrystallized solid is white to off-white.

In some embodiments, provided are processes of preparing compounds of Formula (I), or a pharmaceutically acceptable salt thereof, wherein the solid is dried at about 55° C. In some embodiments, the solid is dried between about 45° C. to about 55° C. In some embodiments, the solid is dried between about 55° C. to about 65° C. In some embodiments, the solid is dried between about 50° C. to about 60° C.

In some embodiments, processes of preparing compounds of Formula (I), or a pharmaceutically acceptable salt thereof, wherein X is O.

In some embodiments, processes of preparing compounds of Formula (I), or a pharmaceutically acceptable salt thereof, wherein Y is O.

In some embodiments, processes of preparing compounds of Formula (I), or a pharmaceutically acceptable salt thereof, wherein the compound that is prepared or produced has a formula of Formula (VI)

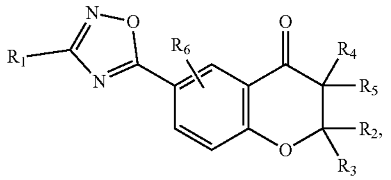

Formula (VII)

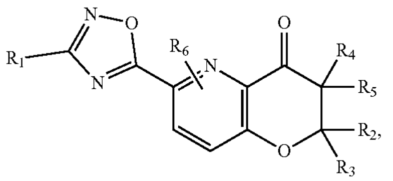

Formula (VIII)

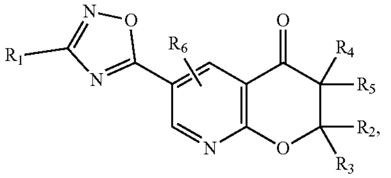

or

Formula (IX)

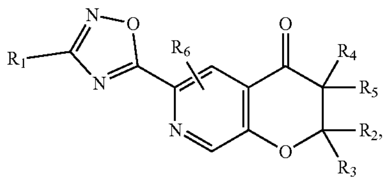

wherein the variables are as defined in claim 1. In some embodiments, processes of preparing compounds of Formula (I), or a pharmaceutically acceptable salt thereof, wherein the compound has a formula of Formula (VI)

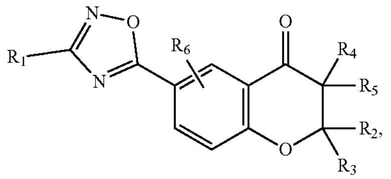

wherein the variables are as defined in claim 1. In some embodiments, processes of preparing compounds of Formula (I), or a pharmaceutically acceptable salt thereof, wherein the compound that is produced has a formula of Formula (VII)

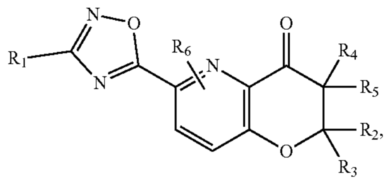

wherein the variables are as defined in claim 1. In some embodiments, processes of preparing compounds of Formula (I), or a pharmaceutically acceptable salt thereof, wherein the compound that is produced has a formula of Formula (VIII)

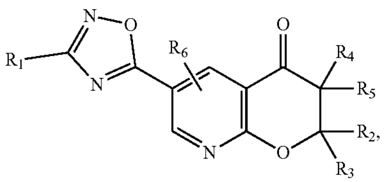

wherein the variables are as defined in claim 1. In some embodiments, processes of preparing compounds of Formula (I), or a pharmaceutically acceptable salt thereof, wherein the compound that is produced has a formula of Formula (IX)

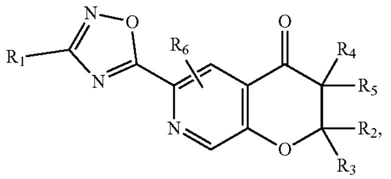

wherein the variables are as defined in claim 1.

In some embodiments, provided are processes of preparing compounds of Formula (I), or a pharmaceutically acceptable salt thereof, wherein $R_4$ and $R_5$ are each is independently H or optionally substituted $C_1$-$C_6$ alkyl.

In some embodiments, provided are processes of preparing compounds of Formula (I), or a pharmaceutically acceptable salt thereof, wherein either $R_4$ or $R_5$ is H.

In some embodiments, provided are processes of preparing compounds of Formula (I), or a pharmaceutically acceptable salt thereof, wherein the compound of Formula (I), or a pharmaceutically acceptable salt thereof, has a formula of Formula (X)

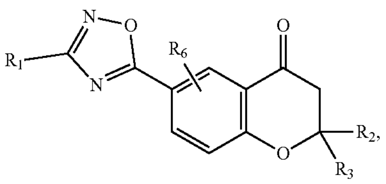

wherein the variables are as defined in claim 1.

In some embodiments, provided are processes of preparing compounds of Formula (I), or a pharmaceutically acceptable salt thereof, wherein the compound of Formula (I), or a pharmaceutically acceptable salt thereof, has a formula of Formula (XI)

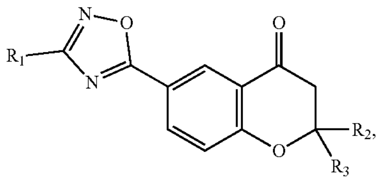

wherein the variables are as defined in claim 1.

In some embodiments, provided are processes of preparing compounds of Formula (I), or a pharmaceutically acceptable salt thereof, wherein $R_2$ and $R_3$ are each is independently H or optionally substituted $C_1$-$C_6$ alkyl.

In some embodiments, provided are processes of preparing compounds of Formula (I), or a pharmaceutically acceptable salt thereof, wherein $R_2$ and $R_3$ are both optionally substituted $C_1$-$C_6$ alkyl.

In some embodiments, provided are processes of preparing compounds of Formula (I), or a pharmaceutically acceptable salt thereof, wherein both $R_2$ and $R_3$ are methyl or ethyl. In some embodiments, provided are processes of preparing compounds of Formula (I), or a pharmaceutically acceptable salt thereof, wherein both $R_2$ and $R_3$ are methyl. In some embodiments, provided are processes of preparing compounds of Formula (I), or a pharmaceutically acceptable salt thereof, wherein both $R_2$ and $R_3$ are ethyl.

In some embodiments, provided are processes of preparing compounds of Formula (I), or a pharmaceutically acceptable salt thereof, wherein the compound of Formula (I), or a pharmaceutically acceptable salt thereof, has a formula of Formula (XII)

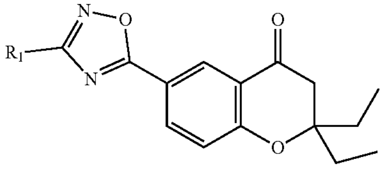

and $R_1$ is as defined in claim 1.

In some embodiments, provided are processes of preparing compounds of Formula (I), or a pharmaceutically acceptable salt thereof, wherein either $R_2$ or $R_3$ is H.

In some embodiments, provided are processes of preparing compounds of Formula (I), or a pharmaceutically acceptable salt thereof, wherein $R_2$ and $R_3$ are together optionally substituted cycloalkyl, or optionally substituted cycloheteroalkyl.

In some embodiments, provided are processes of preparing compounds of Formula (I), or a pharmaceutically acceptable salt thereof, wherein $R_2$ and $R_3$ are together optionally substituted 5-, 6-, or 7-membered cycloalkyl or cycloheteroalkyl.

In some embodiments, provided are processes of preparing compounds of Formula (I), or a pharmaceutically acceptable salt thereof, wherein $R_1$ is optionally substituted $C_1$-$C_6$ alkyl, optionally substituted carbocycle, optionally substituted aryl group, or optionally substituted heteroaryl group.

In some embodiments, provided are processes of preparing compounds of Formula (I), or a pharmaceutically acceptable salt thereof, wherein $R_1$ is optionally substituted aryl group or optionally substituted heteroaryl group.

In some embodiments, provided are processes of preparing compounds of Formula (I), or a pharmaceutically acceptable salt thereof, wherein $R_1$ is optionally substituted heteroaryl group. In some embodiments, provided are processes of preparing compounds of Formula (I), or a pharmaceutically acceptable salt thereof, wherein $R_1$ is optionally substituted nitrogen-containing heteroaryl group.

In some embodiments, provided are processes of preparing compounds of Formula (I), or a pharmaceutically acceptable salt thereof, wherein $R_1$ is

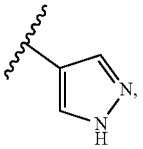 , 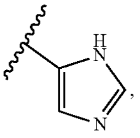 , 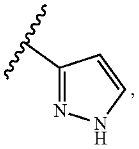 ,

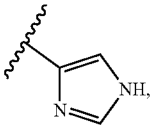 or 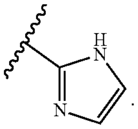 .

In some embodiments, provided are processes of preparing compounds of Formula (I), or a pharmaceutically acceptable salt thereof, wherein $R_1$ is

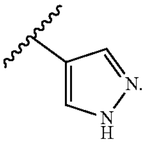 [SMILES: *c1cn[nH]c1]

In some embodiments, provided are processes of preparing compounds of Formula (I), or a pharmaceutically acceptable salt thereof, wherein $R_1$ is

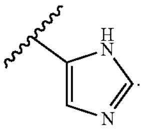 [SMILES: *c1cnc[nH]1]

In some embodiments, provided are processes of preparing compounds of Formula (I), or a pharmaceutically acceptable salt thereof, wherein $R_1$ is

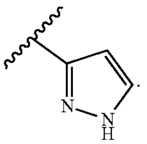 [SMILES: *c1cc[nH]n1]

In some embodiments, provided are processes of preparing compounds of Formula (I), or a pharmaceutically acceptable salt thereof, wherein $R_1$ is

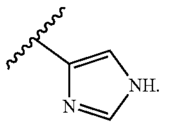 [SMILES: *c1c[nH]cn1]

In some embodiments, provided are processes of preparing compounds of Formula (I), or a pharmaceutically acceptable salt thereof, wherein $R_1$ is

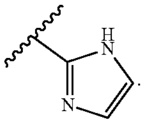 [SMILES: *c1ncc[nH]1]

In some embodiments, provided are processes of preparing compounds of Formula (I), or a pharmaceutically acceptable salt thereof, wherein the compound of Formula (I) is

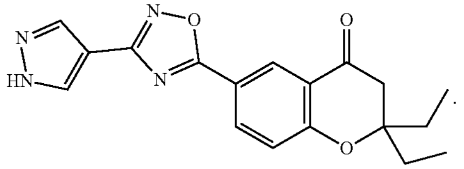 [SMILES: CCC1(CC)CC(=O)c2cc(-c3nc(-c4cn[nH]c4)no3)ccc2O1]

In some embodiments, also provided are processes of preparing the compound having the structure of

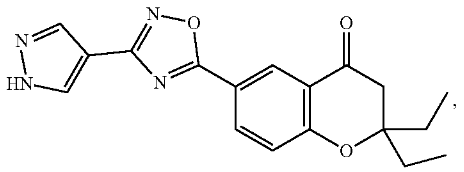 [SMILES: CCC1(CC)CC(=O)c2cc(-c3nc(-c4cn[nH]c4)no3)ccc2O1]

or a pharmaceutically acceptable salt thereof comprising the steps of:

(a) adding EDC hydrochloride and ethyl cyanohydroxyiminoacetate to a solution of

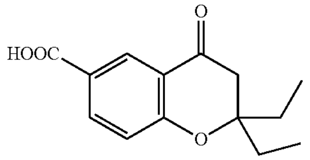 [SMILES: CCC1(CC)CC(=O)c2cc(C(=O)O)ccc2O1]

in dimethylformamide to form a mixture and stirring the mixture for at least about 1 hour;

(b) stirring the mixture of the step (a) with

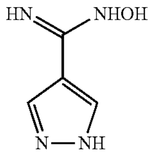

for about 1 hour;

(c) heating the mixture of the step (b) to a temperature at about 95° C. and stirring the mixture under the temperature for at least about 5 hour;

(d) cooling the mixture of the step (c) to about 15-20° C. and adding water to the mixture form a slurry;

(e) stirring the slurry of the step (d) at about 15-20° C. for about 1 h;

(f) filtering the slurry of the step (e) to from a solid;

(g) washing the solid of the step (f) with water and methyl-tert-butyl ether; and (h) drying the solid of the step (g) at least about 55° C. under vacuum to form

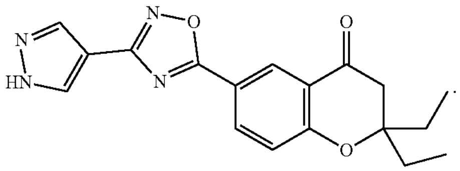 [SMILES: CCC1(CC)CC(=O)c2cc(-c3nc(-c4cn[nH]c4)no3)ccc2O1]

In some embodiments, provided are processes of preparing compounds of Formula (I), or a pharmaceutically acceptable salt thereof further comprising a method of preparing a compound of Formula (II)

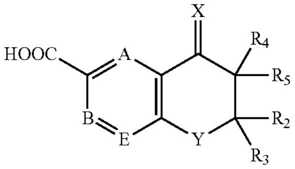

by contacting

Formula (V)

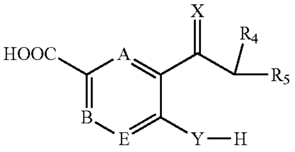

with $R_2R_3C{=}O$ under suitable conditions, wherein the variables are as defined herein. In some embodiments, wherein the contacting is reacting. In some embodiments, the contacting is condensing. In some embodiments, the contacting is coupling. In some embodiments, the contacting is cyclizing.

In some embodiments, also provided are methods of preparing compounds of

Formula (II)

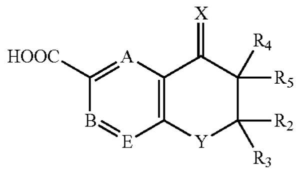

comprising the steps of:

(a) adding pyrrolidine to a solution of a compound of

Formula (V)

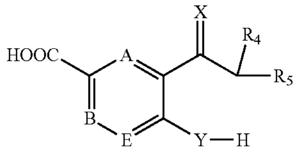

in a compound of $R_2R_3C{=}O$ to form a mixture;

(b) heating the mixture of step (a) to reflux and stirring the refluxing mixture for about 19.5 hours under the temperature, cooling the mixture to about 15-20° C., and adding water to the mixture;

(c) adjusting the pH of the mixture of step (b) to about 2 with HCl;

(d) stirring the mixture of step (c) with n-heptane to form a slurry and stirring the slurry at about 15-20° C. for about 1 hour, and filtering the slurry to form a solid; and (e) washing the solid of step (d) with water and n-heptane; and (f) drying the solid of step (e) at about 50° C. under vacuum to form the compound of Formula (II)

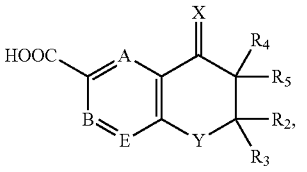

wherein:

A, B, and E are each independently N or $CR_6$;

X and Y are each independently O, S, or $NR_7$, $R_4$, $R_5$, $R_6$, and $R_7$, are each independently H, optionally substituted $C_1$-$C_6$ alkyl, optionally substituted $C_1$-$C_6$ hydroxyalkyl, optionally substituted $C_1$-$C_6$ alkoxy, optionally substituted cycloalkyl, or optionally substituted cycloheteroalkyl or $R_4$ and $R_5$ are together optionally substituted cycloalkyl, or optionally substituted cycloheteroalkyl.

In some embodiments, provided are processes of preparing compounds of Formula (II), or a pharmaceutically acceptable salt thereof, wherein, in the step (b), the mixture of step (a) is heated to reflux at or close to the boiling point of the compound of $R_2R_3C{=}O$. In some embodiments, in the step (b), the mixture of step (a) is heated to about 95° C. In some embodiments, in the step (b), the mixture of step (a) is heated to between about 90° C. and about 95° C. In some embodiments, in the step (b), the mixture of step (a) is heated to between about 85° C. and about 95° C. In some embodiments, in the step (b), the mixture of step (a) is heated to between about 80° C. and about 95° C. In some embodiments, in the step (b), the mixture of step (a) is heated to between about 75° C. and about 95° C. In some embodiments, in the step (b), the mixture of step (a) is heated to between about 95° C. and about 100° C. In some embodiments, in the step (b), the mixture of step (a) is heated to between about 95° C. and about 105° C. In some embodiments, in the step (b), the mixture of step (a) is heated to between about 95° C. and about 110° C. In some embodiments, in the step (b), the mixture of step (a) is heated to between about 90° C. and about 115° C.

In some embodiments, provided are processes of preparing compounds of Formula (II), or a pharmaceutically acceptable salt thereof, wherein A is N or $CR_6$. In some embodiments, A is N. In some embodiments, A is $CR_6$.

In some embodiments, provided are processes of preparing compounds of Formula (II), or a pharmaceutically acceptable salt thereof, wherein B is N or $CR_6$. In some embodiments, B is N. In some embodiments, B is $CR_6$.

In some embodiments, provided are processes of preparing compounds of Formula (II), or a pharmaceutically acceptable salt thereof, wherein E is N or $CR_6$. In some embodiments, E is N. In some embodiments, E is $CR_6$.

In some embodiments, provided are processes of preparing compounds of Formula (II), or a pharmaceutically acceptable salt thereof, wherein X is O, S, or $NR_7$. In some embodiments, X is O. In some embodiments, X is S. In some embodiments, X is $NR_7$.

In some embodiments, provided are processes of preparing compounds of Formula (II), or a pharmaceutically acceptable salt thereof, wherein Y is O, S, or $NR_7$. In some embodiments, Y is O. In some embodiments, Y is S. In some embodiments, Y is $NR_7$.

In some embodiments, provided are processes of preparing compounds of Formula (II), or a pharmaceutically acceptable salt thereof, wherein $R_2$ is H, optionally substituted $C_1$-$C_6$ alkyl, optionally substituted $C_1$-$C_6$ hydroxyalkyl, optionally substituted $C_1$-$C_6$ alkoxy, optionally substituted cycloalkyl, or optionally substituted cycloheteroalkyl. In some embodiments, $R_2$ is H. In some embodiments, $R_2$ is optionally substituted $C_1$-$C_6$ alkyl. In some embodiments, $R_2$ is optionally substituted $C_1$-$C_6$ hydroxyalkyl. In some embodiments, $R_2$ is optionally substituted $C_1$-$C_6$ alkoxy. In some embodiments, $R_2$ is optionally substituted cycloalkyl. In some embodiments, $R_2$ is optionally substituted cycloheteroalkyl.

In some embodiments, provided are processes of preparing compounds of Formula (II), or a pharmaceutically acceptable salt thereof, wherein $R_3$ is H, optionally substituted $C_1$-$C_6$ alkyl, optionally substituted $C_1$-$C_6$ hydroxyalkyl, optionally substituted $C_1$-$C_6$ alkoxy, optionally substituted cycloalkyl, or optionally substituted cycloheteroalkyl. In some embodiments, $R_3$ is H. In some embodiments. $R_3$ is optionally substituted $C_1$-$C_6$ alkyl. In some embodiments, $R_3$ is optionally substituted $C_1$-$C_6$ hydroxyalkyl. In some embodiments, $R_3$ is optionally substituted $C_1$-$C_6$ alkoxy. In some embodiments. $R_3$ is optionally substituted cycloalkyl. In some embodiments, $R_3$ is optionally substituted cycloheteroalkyl.

In some embodiments, provided are processes of preparing compounds of Formula (I), or a pharmaceutically acceptable salt thereof, wherein $R_4$ is H, optionally substituted $C_1$-$C_6$ alkyl, optionally substituted $C_1$-$C_6$ hydroxyalkyl, optionally substituted $C_1$-$C_6$ alkoxy, optionally substituted cycloalkyl, or optionally substituted cycloheteroalkyl. In some embodiments, $R_4$ is H. In some embodiments, $R_4$ is optionally substituted $C_1$-$C_6$ alkyl. In some embodiments, $R_4$ is optionally substituted $C_1$-$C_6$ hydroxyalkyl. In some embodiments. $R_4$ is optionally substituted $C_1$-$C_6$ alkoxy. In some embodiments, $R_4$ is optionally substituted cycloalkyl. In some embodiments, $R_4$ is optionally substituted cycloheteroalkyl.

In some embodiments, provided are processes of preparing compounds of Formula (I), or a pharmaceutically acceptable salt thereof, wherein $R_5$ is H, optionally substituted $C_1$-$C_6$ alkyl, optionally substituted $C_1$-$C_6$ hydroxyalkyl, optionally substituted $C_1$-$C_6$ alkoxy, optionally substituted cycloalkyl, or optionally substituted cycloheteroalkyl. In some embodiments, $R_5$ is H. In some embodiments, $R_5$ is optionally substituted $C_1$-$C_6$ alkyl. In some embodiments, $R_5$ is optionally substituted $C_1$-$C_6$ hydroxyalkyl. In some embodiments, $R_5$ is optionally substituted $C_1$-$C_6$ alkoxy. In some embodiments, $R_5$ is optionally substituted cycloalkyl. In some embodiments, $R_5$ is optionally substituted cycloheteroalkyl.

In some embodiments, provided are processes of preparing compounds of Formula (I), or a pharmaceutically acceptable salt thereof, wherein $R_6$ is H, optionally substituted $C_1$-$C_6$ alkyl, optionally substituted $C_1$-$C_6$ hydroxyalkyl, optionally substituted $C_1$-$C_6$ alkoxy, optionally substituted cycloalkyl, or optionally substituted cycloheteroalkyl. In some embodiments, $R_6$ is H. In some embodiments. $R_6$ is optionally substituted $C_1$-$C_6$ alkyl. In some embodiments, $R_6$ is optionally substituted $C_1$-$C_6$ hydroxyalkyl. In some embodiments, $R_6$ is optionally substituted $C_1$-$C_6$ alkoxy. In some embodiments, $R_6$ is optionally substituted cycloalkyl. In some embodiments, $R_6$ is optionally substituted cycloheteroalkyl.

In some embodiments, provided are processes of preparing compounds of Formula (II), or a pharmaceutically acceptable salt thereof, wherein $R_7$ is H, optionally substituted $C_1$-$C_6$ alkyl, optionally substituted $C_1$-$C_6$ hydroxyalkyl, optionally substituted $C_1$-$C_6$ alkoxy, optionally substituted cycloalkyl, or optionally substituted cycloheteroalkyl. In some embodiments, $R_7$ is H. In some embodiments. $R_7$ is optionally substituted $C_1$-$C_6$ alkyl. In some embodiments, $R_7$ is optionally substituted $C_1$-$C_6$ hydroxyalkyl. In some embodiments, $R_7$ is optionally substituted $C_1$-$C_6$ alkoxy. In some embodiments, $R_7$ is optionally substituted cycloalkyl. In some embodiments, $R_7$ is optionally substituted cycloheteroalkyl.

In some embodiments, provided are processes of preparing compounds of Formula (II), or a pharmaceutically acceptable salt thereof, wherein $R_2$ and $R_3$ are together optionally substituted cycloalkyl, or optionally substituted cycloheteroalkyl. In some embodiments, $R_2$ and $R_3$ are together optionally substituted cycloalkyl. In some embodiments, $R_2$ and $R_3$ are together optionally substituted cycloheteroalkyl.

In some embodiments, provided are processes of preparing compounds of Formula (II), or a pharmaceutically acceptable salt thereof, wherein $R_4$ and $R_5$ are together optionally substituted cycloalkyl, or optionally substituted cycloheteroalkyl. In some embodiments, $R_4$ and $R_5$ are together optionally substituted cycloalkyl. In some embodiments, $R_4$ and $R_5$ are together optionally substituted cycloheteroalkyl.

In some embodiments, provided are processes of preparing compounds of Formula (I), or a pharmaceutically acceptable salt thereof further comprising methods of preparing a compound of Formula (III)

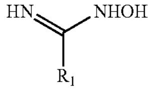

by contacting a compound of a formula of $R_1CN$ with ammonium hydroxide and wherein $R_1$ is H, OH, $NH_2$, $NO_2$, optionally substituted carbocycle, optionally substituted aryl group, optionally substituted heteroaryl group, branched or unbranched alkyl alcohol, halo, branched or unbranched alkyl, amide, cyano, alkoxy, haloalkyl, aklylsulfonyl, nitrite, or alkylsulfanyl. In some embodiments, wherein the contacting is reacting. In some embodiments, the contacting is condensing. In some embodiments, the contacting is coupling. In some embodiments, the contacting is cyclizing.

In some embodiments, also provided are methods of preparing a compound of

Formula (III)

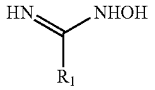

comprising the steps of:

(a) adding hydroxylamine to a solution of a compound of $R_1CN$ in an alcohol form a mixture;
(b) heating the mixture of the step (a) to a temperature of about 75° C. and stirring the mixture for about 4 hours under the temperature to form a slurry
(c) cooling the slurry of the step (b) to ambient temperature and stirring for about 16 hours under the ambient temperature;
(d) filtering the slurry of the step (c) to form a solid; and
(e) washing the solid of the step (d) with the alcohol and drying the washed solid at about 50° C. under vacuum to form the compound of Formula (III)

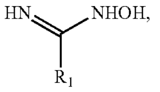

wherein $R_1$ is as defined herein.

In some embodiments, provided are processes of preparing compounds of Formula (III), or a pharmaceutically acceptable salt thereof, wherein $R_1$ is H, OH, $NH_2$, $NO_2$, optionally substituted carbocycle, optionally substituted aryl group, optionally substituted heteroaryl group, branched or unbranched alkyl alcohol, halo, branched or unbranched alkyl, amide, cyano, alkoxy, haloalkyl, aklylsulfonyl, nitrite, or alkylsulfanyl. In some embodiments, $R_1$ is H. In some embodiments, $R_1$ is OH. In some embodiments, $R_1$ is $NH_2$. In some embodiments, $R_1$ is $NO_2$. In some embodiments, $R_1$ is optionally substituted carbocycle. In some embodiments, $R_1$ is optionally substituted aryl group. In some embodiments. $R_1$ is optionally substituted heteroaryl group. In some embodiments, $R_1$ is branched or unbranched alkyl alcohol. In some embodiments, $R_1$ is halo. In some embodiments, $R_1$ is branched or unbranched alkyl. In some embodiments. $R_1$ is amide. In some embodiments, $R_1$ is cyano. In some embodiments, $R_1$ is alkoxy. In some embodiments, $R_1$ is haloalkyl. In some embodiments, $R_1$ is aklylsulfonyl. In some embodiments, $R_1$ is nitrite. In some embodiments, $R_1$ is alkylsulfanyl.

In some embodiments, provided are processes of preparing compounds of Formula (III), or a pharmaceutically acceptable salt thereof, wherein the alcohol is an optionally substituted $C_1$-$C_6$ alkyl alcohol. In some embodiments, the alcohol is methanol, ethanol, propanol, or butanol. In some embodiments, the alcohol is ethanol. In some embodiments, the alcohol is methanol. In some embodiments, the alcohol is propanol. In some embodiments, the alcohol is butanol.

In some embodiments, provided are processes of preparing compounds of Formula (III), or a pharmaceutically acceptable salt thereof, wherein the hydroxylamine is hydroxylamine hydrochloride salt. In some embodiments, provided are processes of preparing compounds of Formula (III), or a pharmaceutically acceptable salt thereof, wherein when the hydroxylamine is hydroxylamine hydrochloride salt, an organic based is added. In some embodiments, the organic based is diisopropylethylamine. In some embodiments, the amount of the organic based is at least about 1.5 equivalent in molar ratio of the amount of hydroxylamine hydrochloride salt.

In some embodiments, provided are processes of preparing compounds of Formula (III), or a pharmaceutically acceptable salt thereof, in the step (a), the amount of hydroxylamine is at least about 1.5 equivalent in molar ratio to the amount of $R_1CN$.

In some embodiments, provided are processes of preparing compounds of Formula (III), or a pharmaceutically acceptable salt thereof, wherein, in the step (b), the mixture of step (a) is heated to reflux at or close to the boiling point of the alcohol. In some embodiments, the mixture of step (a) is heated to about 75° C. In some embodiments, in the step (b), the mixture of step (a) is heated to between about 70° C. and about 75° C. In some embodiments, in the step (b), the mixture of step (a) is heated to between about 65° C. and about 75° C. In some embodiments, in the step (b), the mixture of step (a) is heated to between about 60° C. and about 75° C. In some embodiments, in the step (b), the mixture of step (a) is heated to between about 75° C. and about 75° C. In some embodiments, in the step (b), the mixture of step (a) is heated to between about 75° C. and about 80° C. In some embodiments, in the step (b), the mixture of step (a) is heated to between about 75° C. and about 85° C. In some embodiments, in the step (b), the mixture of step (a) is heated to between about 75° C. and about 90° C. In some embodiments, in the step (b), the mixture of step (a) is heated to between about 90° C. and about 95° C.

In some embodiments, provided are processes of preparing compounds of Formula (I), or a pharmaceutically acceptable salt thereof, wherein the compound of Formula (II)

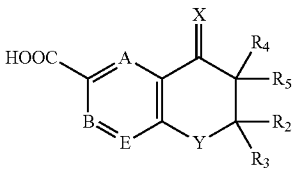

is contacted with a coupling reagent, with or without the addictive, to form an intermediate having the structure of Formula (XIII)

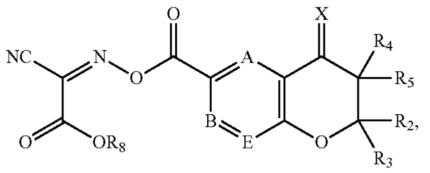

wherein $R_5$ is optionally substituted $C_1$-$C_6$ alkyl and $R_2$, $R_3$, $R_4$, $R_5$, $R_6$, and $R_7$, are as defined herein, is provided. In some embodiments, wherein the compound of Formula (II) reacts with the coupling reagent, with or without the addictive, to form the intermediate Formula (XIII). In some embodiments, wherein the compound of Formula (II) couples with the coupling reagent, with or without the addictive, to form the intermediate Formula (XIII).

In some embodiments, provided are processes of preparing compounds of Formula (I), or a pharmaceutically acceptable salt thereof, wherein the intermediate of Formula (XIII) is a compound having the structure of Formula (XIV)

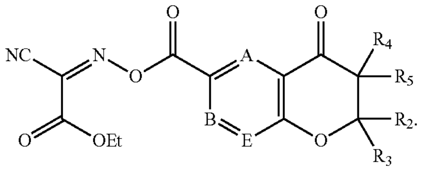

In some embodiments, the intermediate of Formula (XIII) is a compound having the structure of Formula (XIV-I)

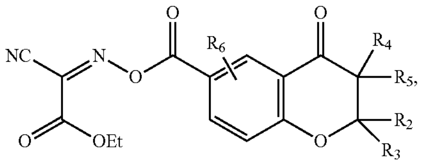

Formula (XIV-II)

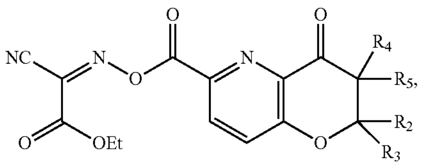

Formula (XIV-III)

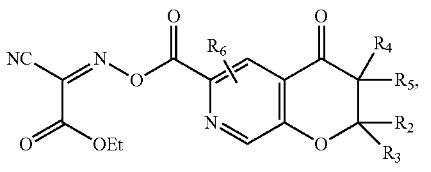

or

-continued

Formula (XIV-IV)

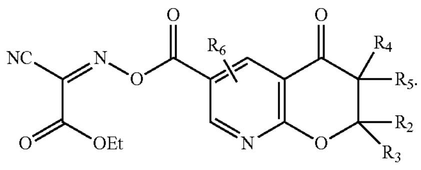

In some embodiments, the intermediate of Formula (XIII) is a compound having the structure of Formula (XIV-I)

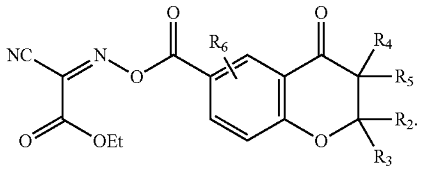

In some embodiments, the intermediate of Formula (XIII) is a compound having the structure of Formula (XIV-V)

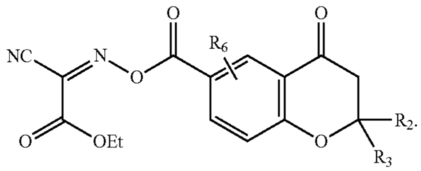

In some embodiments, the intermediate of Formula (XIII) is a compound having the structure of Formula (XIV-VI)

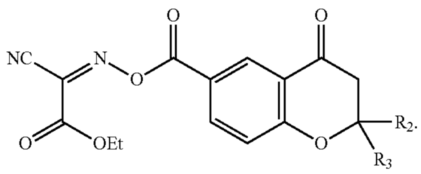

In some embodiments, the intermediate of Formula (XIII) is a compound having the structure of

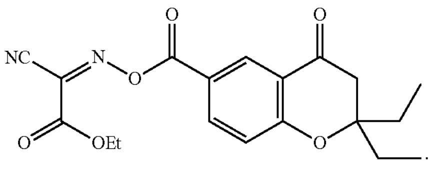 [SMILES: CCOC(=O)/C(C#N)=N\OC(=O)c1ccc2c(c1)C(=O)CC(CC)(CC)O2]

In some embodiments, provided are processes of preparing compounds of Formula (I), or a pharmaceutically acceptable salt thereof, wherein the intermediate having the structure of Formula (XIII)

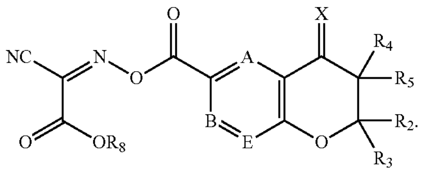

further contacts the compound of

Formula (III)

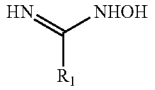

to form an intermediate having a structure of

Formula (XVI)

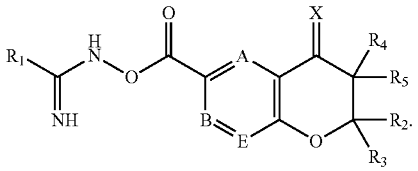

In some embodiments, the intermediate of Formula (XIII) further reacts with the compound of Formula (III) to form an intermediate of Formula (XVI). In some embodiments, the intermediate of Formula (XIII) further couples with the compound of Formula (III) to form an intermediate of Formula (XVI).

In some embodiments, the intermediate of Formula (XVI) is a compound having the structure of Formula (XVII)

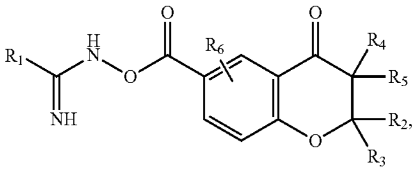

Formula (XVIII)

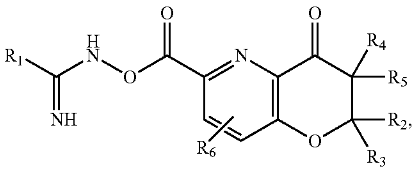

Formula (XIX)

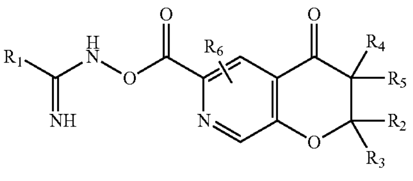

or

-continued

Formula (XX)

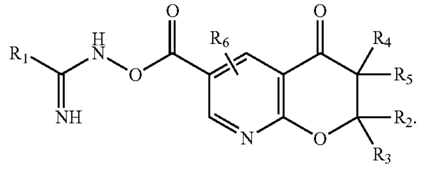

In some embodiments, wherein the intermediate of Formula (XVI) is a compound having the structure of Formula (XVII)

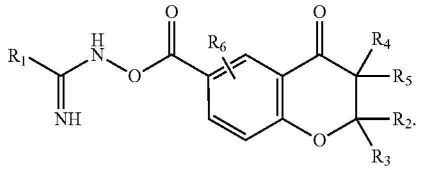

In some embodiments, the intermediate of Formula (XVI) is a compound having the structure of Formula (XVII-I)

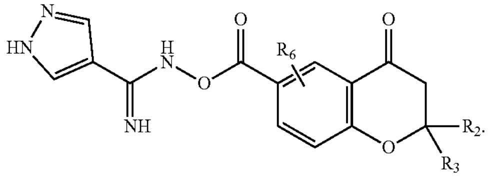

In some embodiments, the intermediate of Formula (XVI) is a compound having the structure of Formula (XVII-II)

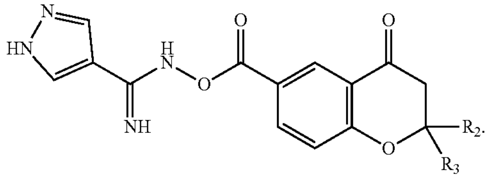

In some embodiments, the intermediate of Formula (XVI) is a compound having the structure of

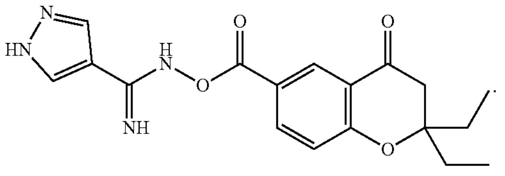 [SMILES: CCC1(CC)CC(=O)c2cc(C(=O)ONC(=N)c3cn[nH]c3)ccc2O1]

In some embodiments, provided are processes of preparing compounds of Formula (I), or a pharmaceutically acceptable salt thereof, wherein the intermediate having the structure of Formula (XVI)

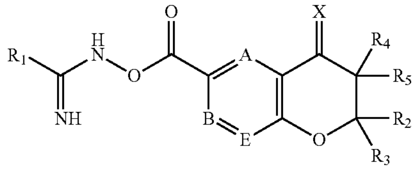

further forms the compound of

Formula (I)

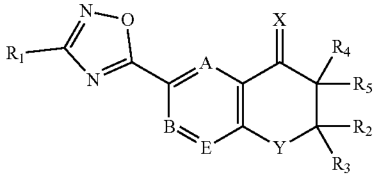

under thermal cyclodehydration conditions. In some embodiments, the intermediate of Formula (XVI) further condenses to form the compound of Formula (I) under thermal cyclodehydration conditions. In some embodiments, the intermediate of Formula (XVI) further cyclizes to form the compound of Formula (I) under thermal cyclodehydration conditions. In some embodiments, wherein the compound of Formula (I)

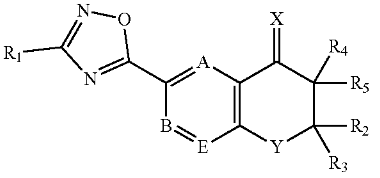 is

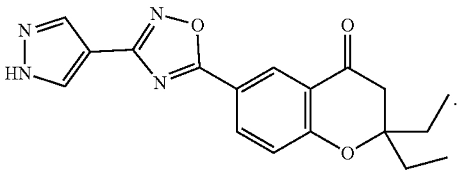

In some embodiments, also provided are compounds of

Formula (XIII)

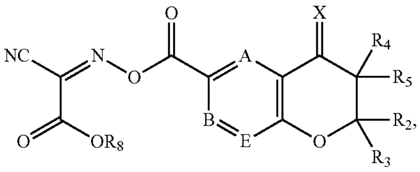

or a pharmaceutically acceptable salt thereof, which are isolated from the processes as described herein.

In some embodiments, also provided compositions comprising one or more compounds of Formula (XIII)

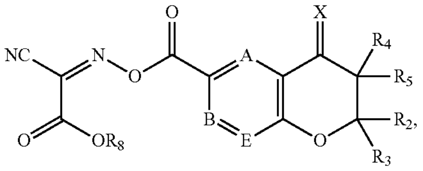

or a pharmaceutically acceptable salt thereof.

In some embodiments, also provided solutions comprising one or more compounds of Formula (XIII)

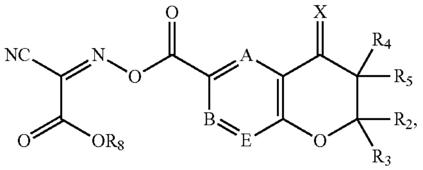

or a pharmaceutically acceptable salt thereof.

In some embodiments, also provided are compounds of

Formula (XVI)

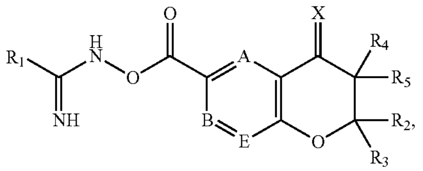

or a pharmaceutically acceptable salt thereof, which are isolated from the processes as described herein.

In some embodiments, also provided compositions comprising one or more compounds of Formula (XVI)

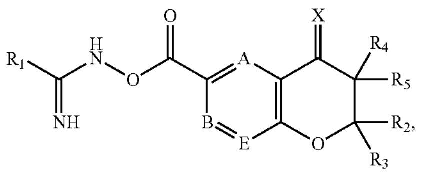

or a pharmaceutically acceptable salt thereof.

In some embodiments, also provided solutions comprising one or more compounds of Formula (XVI)

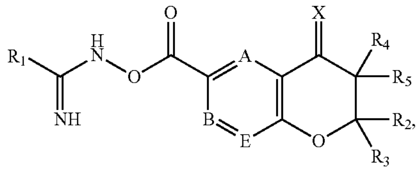

or a pharmaceutically acceptable salt thereof.

In some embodiments, also provided are methods of forming a compound of Formula I, the method comprising reacting the compound having the structure of Formula (XVI)

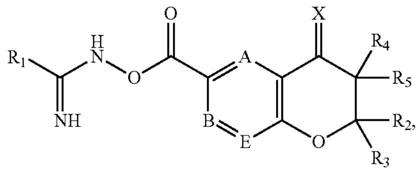

under thermal cyclodehydration conditions to form a compound of

Formula I

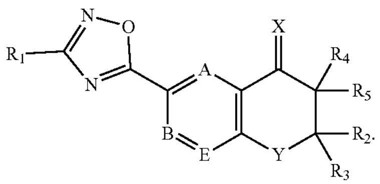

In some embodiments, provided are crystalline forms of the compound having the structure

Figure 6:
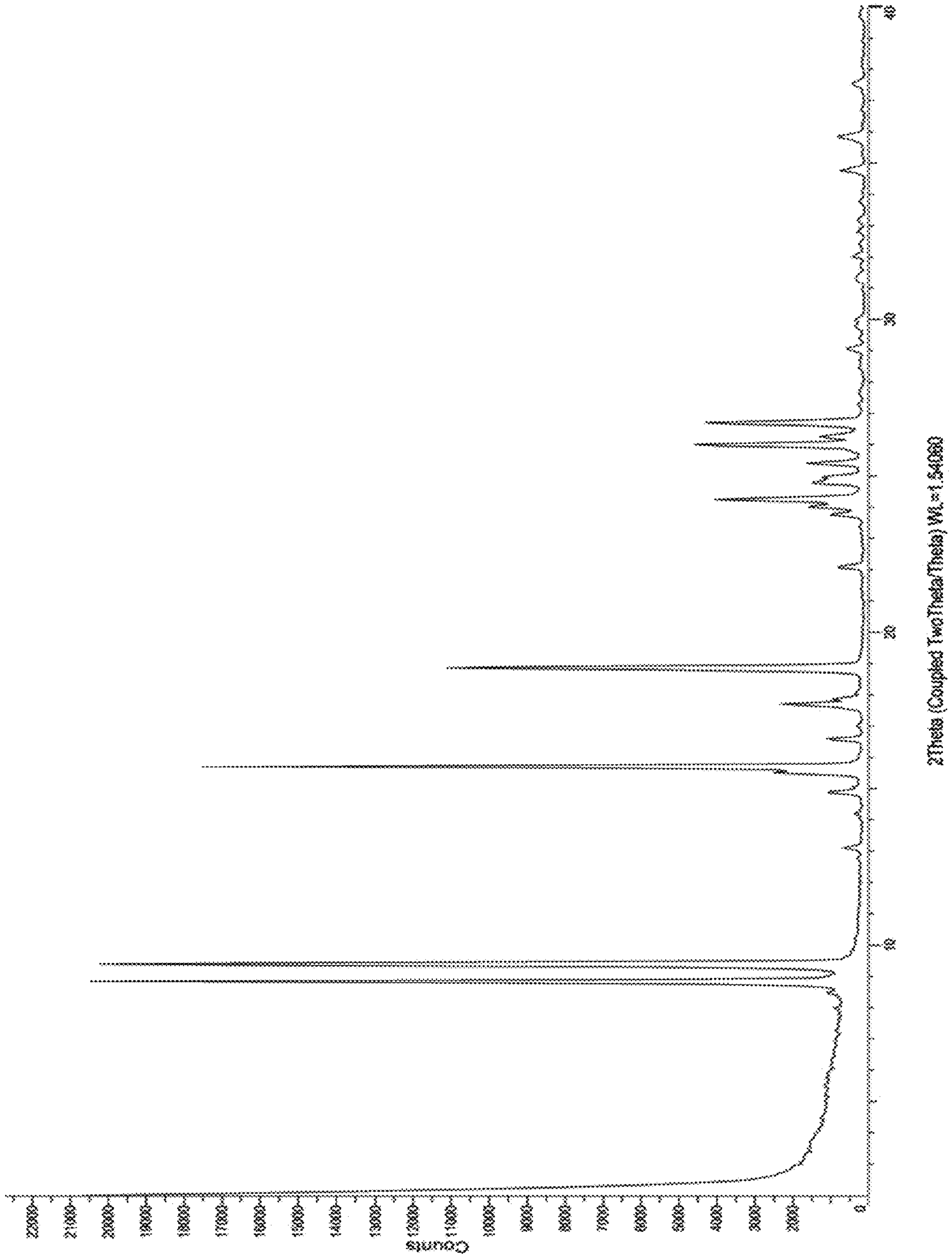
FIG. 6: X-ray powder diffraction (XRPD) results of 6-(3-(1H-pyrazol-4-yl)-1,2,4-oxadiazol-5-yl)-2,2-diethylchroman-4-one (Compound 6-1).

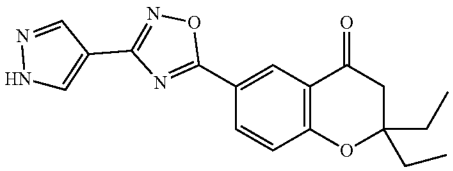 [SMILES: CCC1(CC)CC(=O)c2cc(-c3nc(-c4cn[nH]c4)no3)ccc2O1]

is provided. In some embodiments, the crystalline form is Form I. In some embodiments, the crystalline Form I characterized by an X-ray powder diffraction pattern comprising peaks: at about 8.9±0.5 degrees 2θ, at about 9.4±0.5 degrees 2θ, 15.7±0.5 degrees 2θ, at about 17.7±0.5 degrees 2θ, at about 18.9±0.5 degrees 2θ, 24.3±0.5 degrees 2θ, at about 26.0±0.5 degrees 2θ, and at about 26.7±0.5 degrees 2θ. In some embodiments, the crystalline Form I is characterized by an X-ray powder diffraction pattern comprising one or more peaks as shown in FIG. 6. In some embodiments, the crystalline Form I is characterized by an X-ray powder diffraction pattern comprising one or more peaks as shown in Table 14. In some embodiments, the crystalline Form I is characterized by an X-ray powder diffraction pattern comprising one or more d-spacing values at about 10.0±0.5 degrees angstroms, at about 9.4±0.5 degrees angstroms, at about 5.6±0.5 degrees angstroms, at about 5.0±0.5 degrees angstroms, at about 4.7±0.5 degrees angstroms, at about 3.7±0.5 degrees angstroms, at about 3.4±0.5 degrees angstroms, and at about 3.3±0.5 degrees angstroms.

Although the compounds described herein may be shown with specific stereochemistries around certain atoms, such as cis or trans, the compounds can also be made in the opposite orientation or in a racemic mixture. Such isomers or racemic mixtures are encompassed by the present disclosure. Additionally, although the compounds are shown collectively in a table, any compounds, or a pharmaceutically acceptable salt thereof, can be chosen from the table and used in the embodiments provided for herein.

In some embodiments, pharmaceutical compositions comprising a compound or pharmaceutically salt thereof of any compound described herein are provided.

The compounds described herein can be made by can be made according to the methods described herein and in the examples. The methods described herein can be adapted based upon the compounds desired and described herein. In some embodiments, this method can be used to make one or more compounds as described herein and will be apparent to one of skill in the art which compounds can be made according to the methods described herein.

The conditions and temperatures can be varied, such as shown in the examples described herein. These schemes are non-limiting synthetic schemes and the synthetic routes can be modified as would be apparent to one of skill in the art reading the present specification. The compounds can also be prepared according to the schemes described in the Examples.

The compounds can be used to modulate the $S_1P_1$ receptor. Thus, in some embodiments, the compounds can be referred to as $S_1P_1$ receptor modulating compounds.

Although the compounds in the tables above or in the examples section are shown with specific stereochemistries around certain atoms, such as cis or trans, the compounds can also be made in the opposite orientation or in a racemic mixture.

In some embodiments, the present embodiments provide pharmaceutical compositions comprising a compound or pharmaceutically salt thereof any compound described herein.

In some embodiments, the compounds are made according to schemes described in the examples. The schemes can be used to prepare the compounds and compositions described herein. The conditions and temperatures can be varied, or the synthesis can be performed according to the examples described herein with modifications that are readily apparent based upon the compound being synthesized.

The conditions and temperatures can be varied, such as shown in the examples described herein. These schemes are non-limiting synthetic schemes and the synthetic routes can be modified as would be apparent to one of skill in the art reading the present specification.

The present disclosure also provides the following non-limiting embodiments:

In order that the embodiments disclosed herein may be more efficiently understood, examples are provided below. It should be understood that these examples are for illustrative purposes only and are not to be construed as limiting the embodiments in any manner.

The following examples are illustrative, but not limiting, of the processes described herein. Other suitable modifications and adaptations of the variety of conditions and parameters normally encountered in therapy, synthesis, and other embodiments disclosed herein are within the spirit and scope of the embodiments.

EXAMPLES

Example 1: Processes of Preparing Compounds of Formula (I)

Certain synthetic schemes, both general and specific, are provided herein. The compounds disclosed herein can be made according to the methods described herein or intermediates that lead to the compounds disclosed herein can be made according to the methods described herein. The substitutions can be varied according to the compound or intermediate being made based upon the following examples and other modifications known to one of skill in the art.

The processes disclosed herein were used to prepare the following compounds in the following examples or the examples were varied according to one of skill in the art to prepare the compounds.

General Procedure A:

Scheme 1

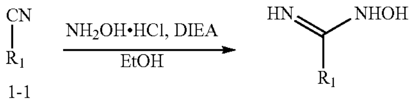

1-1 1-2

$R_1$:

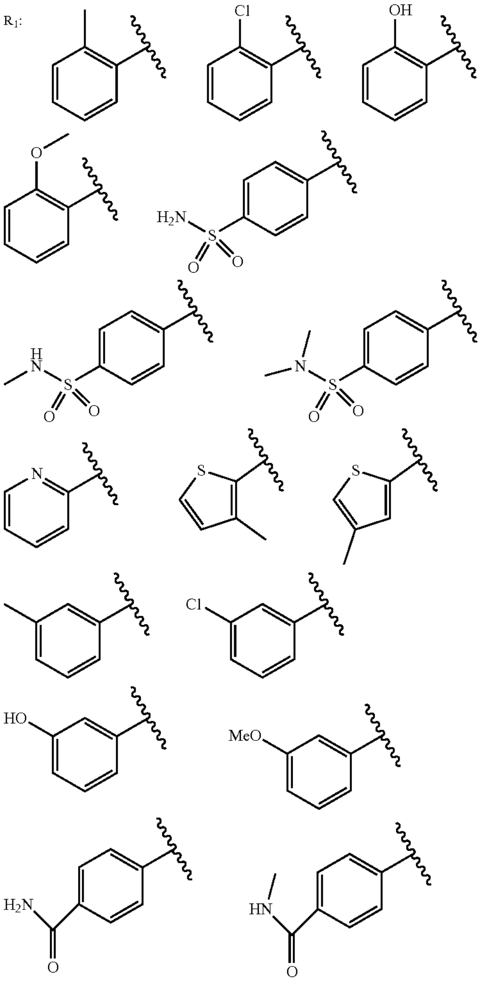

-continued
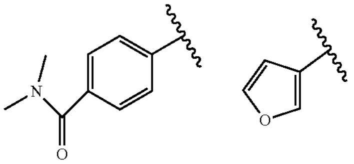
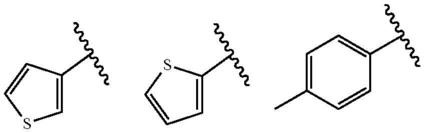
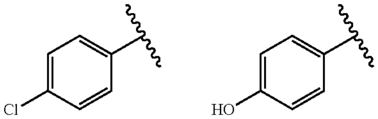
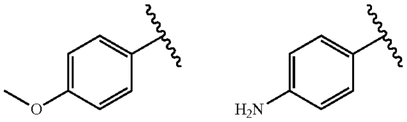
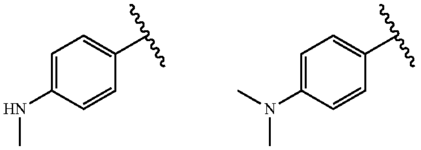
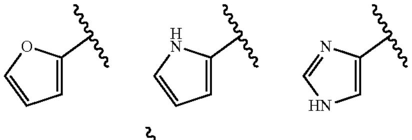
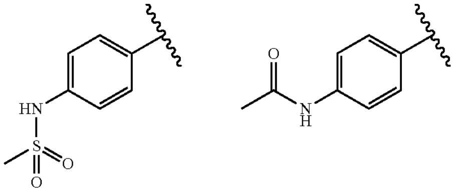
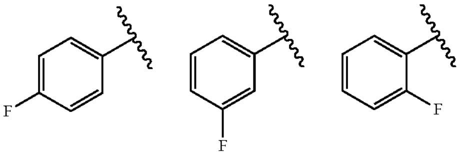
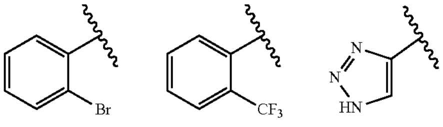
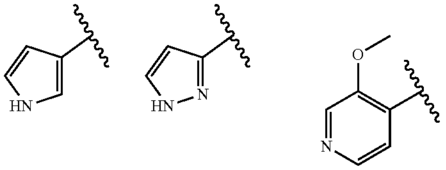
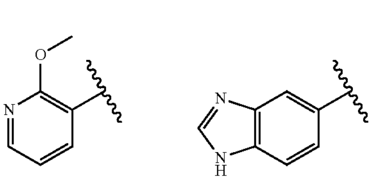
-continued
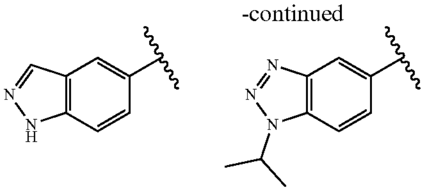
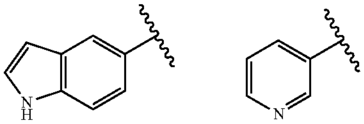
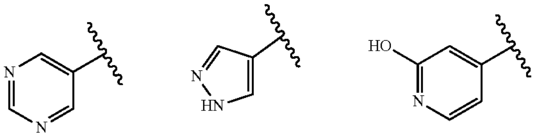
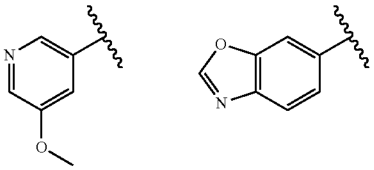
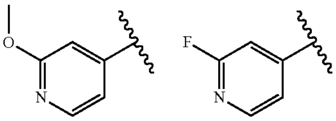
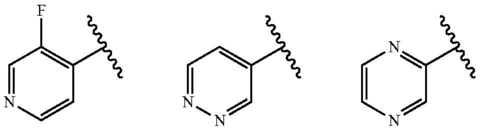
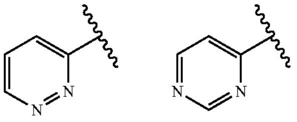
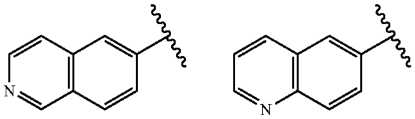
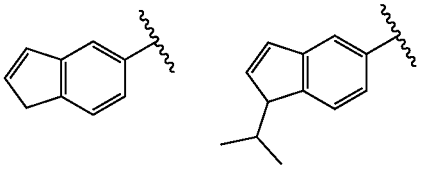
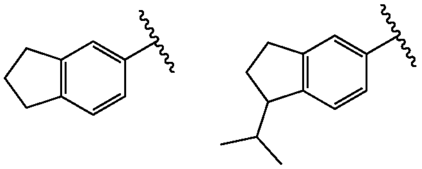
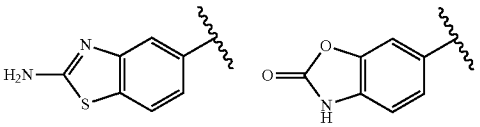
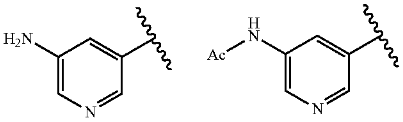

-continued

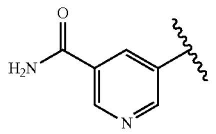
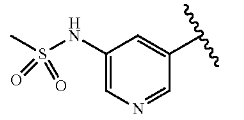
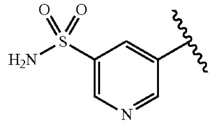
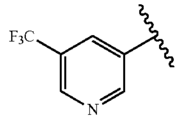
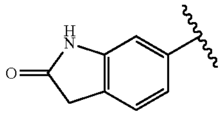
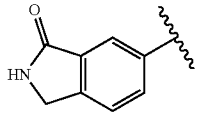
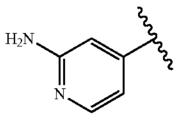
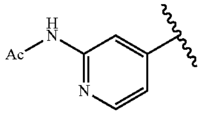
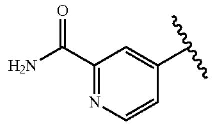
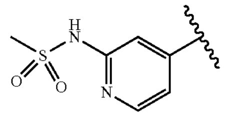
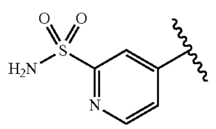
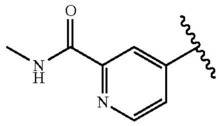
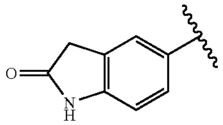
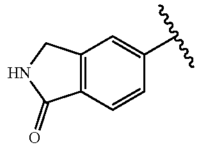
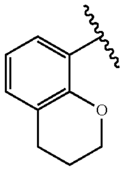
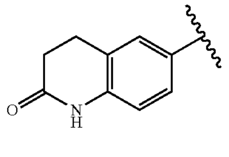
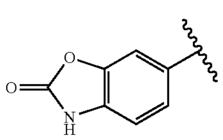
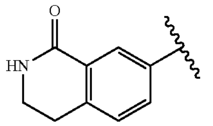
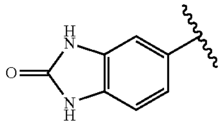
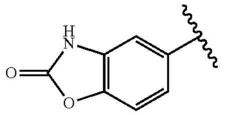

Synthesis of Compound 2-2: N-Hydroxy-1H-pyrazole-4-carboximidamide 2-2

Scheme 2

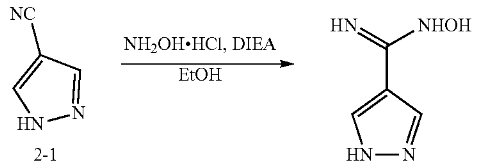

2-1

2-2

Synthesis of Compound 2-2: N-Hydroxy-1H-pyrazole-4-carboximidamide

Based on the results seen in Table 1, EtOH was found to be the preferred solvent for the synthesis of N-hydroxy-1H-pyrazole-4-carboximidamide (Compound 2-2).

TABLE 1

Reaction Condition Screen for Synthesis of Compound 2-2.

| Run | Solvent | Vol | $NH_2OH$•HCl (eq.) | Base (eq.) | Temp (° C.) | Compound 2-2 (%)* | Yield (%) |
|---|---|---|---|---|---|---|---|
| 1 | EtOH | 50 | 1.5 | DIPEA (2.0) | 75 | 98.3 | 70.1 |
| 2 | MeOH | 50 | 1.0 | TEA (1.0) | 65 | 86.0 | 40.6 |
| 3 | MeOH | 25 | 1.5 | TEA (1.5) | 65 | 100 | 22.1 |
| 4 | MeOH | 25 | 1.5 | DIPEA (1.5) | 65 | 98.7 | 29.5 |

*Note:
Compound 2-2 (%) = AUC (%) by HPLC

Next, the volume of ethanol (EtOH) was used for the isolation of N-hydroxy-1H-pyrazole-4-carboximidamide (Compound 2-2) (Table 2). First, the volume of EtOH was decreased to 25 volumes (25 vol) of the Compound 2-1 in Scheme 2. It was observed that by performing the reaction in a lower volume of solvent, the product precipitated out of the reaction mixture upon completion of the reaction. A direct filtration was utilized to isolate the desired product as a white solid (99.9% purity, 84.9% yield). Next, different volumes of EtOH were studied. The yield for EtOH in 5, 10 and 20 volumes of the Compound 2-1 in Scheme 2 were similar. However a decrease in yield was observed with EtOH in 15 volumes. The purity of the product was consistent which suggests that the quality of product was not dependent on the solvent loading. The reaction was performed on a 25 g scale of Compound 2-1 using EtOH in 5, 10 and 25 volumes of Compound 2-1 to study the impact of the yield on a larger scale (Table 3). It was observed the yield increased as the volume of EtOH decreased. The volume of EtOH that provided the best yield for the synthesis of N-hydroxy-1H-pyrazole-4-carboximidamide (Compound 2-2) was found to be 5 volumes (5 vol) of the Compound 2-1. This result could not have been predicted.

TABLE 2

| Isolation Condition Screen for Synthesis of Compound 2-2. | | | | | | | |
|---|---|---|---|---|---|---|---|
| Run | Sol-vent | Vol | NH2OH•HCl (eq.) | DIPEA (eq.) | Temp (° C.) | Com-pound 2-2 (%)* | Yield (%) |
| 1 | EtOH | 50 | 1.5 | 2.0 | 75 | 98.3 | 70.1 |
| 2 | EtOH | 25 | 1.5 | 2.0 | 75 | 99.9 | 84.9 |
| 3 | EtOH | 20 | 1.5 | 2.0 | 75 | 99.9 | 77.5 |
| 4 | EtOH | 15 | 1.5 | 2.0 | 75 | 99.9 | 66.4 |
| 5 | EtOH | 10 | 1.5 | 2.0 | 75 | 99.9 | 75.0 |
| 6 | EtOH | 5 | 1.5 | 2.0 | 75 | 99.9 | 76.5 |

*Note:
Compound 2-2 (%) = AUC (%) by HPLC

TABLE 3

| Volume of EtOH Screen for Synthesis of Compound 2-2 on 25 g Scale. | | | | | | | |
|---|---|---|---|---|---|---|---|
| Run | Scale | EtOH (Vol) | NH2OH•HCl (eq.) | DIPEA (eq.) | Temp (° C.) | Com-pound 2 (%)* | Yield (%) |
| 1 | 25 g | 25 | 1.5 | 2.0 | 75 | 99.9 | 59.8 |
| 2 | 25 g | 10 | 1.5 | 2.0 | 75 | 99.9 | 63.7 |
| 3 | 25 g | 5 | 1.5 | 2.0 | 75 | 98.7 | 67.3 |

*Note:
Compound 2-2 (%) = AUC (%) by HPLC

Experimental of Synthesis of Compound 2-2: N-Hydroxy-1H-pyrazole-4-carboximidamide To a stirred solution of 4-cyanopyrazole (2-1, 25 g) in ethanol (125 mL) was added hydroxylamine hydrochloride (28 g) and N,N-diisopropylethylamine (DIPEA) (93.8 mL). The reaction was heated to 75° C. and stirred for 4 hr. During the 4 hr stirring period, the reaction mixture became a white slurry. The slurry was cooled to ambient temperature and stirred for 16 hr. The slurry was filtered to obtain a solid and the solid was washed with EtOH (50 mL×2). The collected solid was dried at 50° C. under vacuum to yield N-hydroxy-1H-pyrazole-4-carboximidamide (Compound 2-2) as a white solid (22.8 g, 67.3% yield).

UPLC-qDa ($C_4H_6N_4O$) calcd 127.05 $[M+H]^+$, found 127.03.

$^1H$ NMR (500 MHZ, DMSO-$d_6$) δ ppm 5.63 (s, 2H), 7.67 (bs, 1H), 7.96 (bs, 1H), 9.11 (s, 1H), 12.87 (bs, 1H).

General Procedure B:

Scheme 3

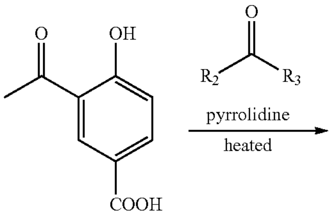

3-1

-continued

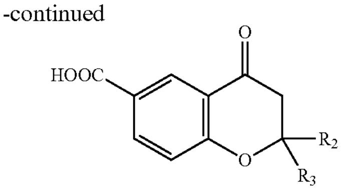

3-2

R2, R3:

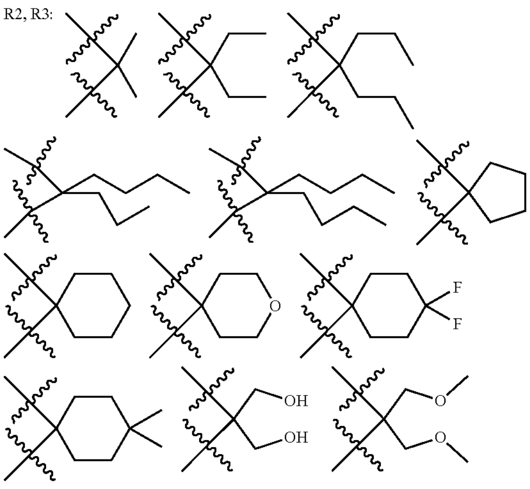

Synthesis of Compound 4-2:2,2-diethyl-4-oxo-3,4-dihydro-2H-1-benzopyran-6-carboxylic Acid Scheme 4

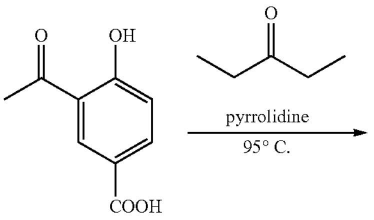

4-1

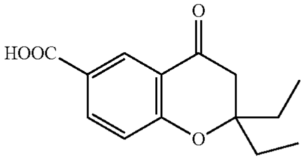

4-2

Synthesis of Compound 4-2:2,2-diethyl-4-oxo-3,4-dihydro-2H-1-benzopyran-6-carboxylic Acid The synthetic route in Scheme 4 involved reacting 3-acetyl-4-hydroxy-benzoic acid Compound 4-1 with 3-pentanone in the presence of pyrrolidine to yield 2,2-diethyl-4-oxo-3,4-dihydro-2H-1-benzopyran-6-carboxylic acid (Compound 2-2). The screening for reaction solvents began by carrying out the reaction in toluene (Table 4). The initial lab run followed the procedure outlined in Patent WO 2000/03681 where pyrrolidine (0.5 eq.) and 3-pentanone (1.0 eq.)

were added to hot toluene in an amount of 15 volumes (15 vol) of Compound 4-1, followed by addition of 3-acetyl-4-hydroxy-benzoic acid (Compound 4-1). The reaction mixture was stirred at 80° C. for 24 hr and showed a low conversion of 3.0%. Next, the order of addition was changed where pyrrolidine and 3-pentanone were added to 3-acetyl-4-hydroxy-benzoic acid (Compound 4-1) in toluene. The equivalences of pyrrolidine and 3-pentanone were increased as well in attempt to further progress the completion of reaction. The reaction was slow in toluene and did not show high conversion to the desired product. Due to the slow kinetics of the reaction in a non-polar solvent such as toluene, polar solvents were screened. The reaction carried out in EtOH showed 80.6% conversion after 48 hr. Next, acetic acid was incorporated as an additive in attempt to increase the progression of the reaction by aiding the proton transfer occurring mechanistically. The addition of acetic acid did not show a significant increase in conversion. The reaction in isopropanol (IPA) showed similar results as EtOH. 1-Propanol was included due to its higher boiling point, which would allow the reaction to be carried out at a higher temperature. The reaction in 1-propanol showed a similar conversion as the reactions carried out in EtOH and IPA except in a shorter reaction time. 3-Pentanone was incorporated as a solvent in which it would have a dual role in the reaction as both solvent and reagent. The reaction carried out in 3-pentanone in an amount of the 10 volumes (10 vol) of Compound 4-1, at 95° C. showed the highest conversion and the shortest reaction

TABLE 4

Reaction Condition Screen for Synthesis of Compound 4-2.

| Run | Solvent | Vol | Temp (° C.) | Reaction Time (hr) | Pyrrolidine (eq.) | 3-Pentanone (eq.) | Compound 4-2 (%)* |
|---|---|---|---|---|---|---|---|
| 1 | Toluene | 15 | 80 | 48 | 0.5 | 1.5 | 3.0 |
| 2 | Toluene | 15 | 80 | 48 | 1.2 | 1.2 | 82.8 |
| 3 | Toluene | 15 | 90 | 48 | 1.5 | 1.5 | 72.7 |
| 4 | EtOH | 10 | 75 | 48 | 1.5 | 1.5 | 80.6 |
| 5** | EtOH | 10 | 75 | 48 | 1.5 | 1.5 | 83.4 |
| 6 | EtOH | 10 | 75 | 48 | 2.0 | 1.5 | 76.0 |
| 7 | IPA | 10 | 75 | 24 | 2.0 | 1.5 | 68.8 |
| 8 | 1-Propanol | 10 | 95 | 16 | 2.0 | 1.5 | 81.0 |
| 9 | 3-Pentanone | 10 | 95 | 15 | 2.0 | — | 95.5 |

*Note:
Compound 4-2 (%) = AUC (%) by HPLC
**0.5 eq. of Acetic Acid used as an additive Encouraged by the results where 3-pentanone played a dual role as both solvent and reagent, the volume of 3-pentanone was examined (Table 5). The reaction was carried out in 2.5 volumes (2.5 vol) of Compound 4-1 and the reaction showed a conversion of 71.9% at 16 hr. Additional 3-pentanone (1.25 vol) was added to the reaction and the conversion increased to 90.6% at 21 hr. The reaction was carried out in 3-pentanone (5 vol) and the reaction showed a conversion of 73.2% at 16 hr. Additional 3-pentanone (1.25 vol) was added to the reaction and the conversion increased to 92.6% at 21 hr. Based on the results seen in Run 2, the reaction was carried out in 3-pentanone (6.25 vol) and 100% conversion was observed at 19 hr. It was found that the reaction proceeded at a faster rate and went to completion with the excess 3-pentanone (6.25 vol) being initially used during the reaction. The volume of 3-pentanone as a solvent that provided the best yield was found to be 6.25 volumes of Compound 4-1.

TABLE 5

Volume of 3-Pentanone Screen for Synthesis of Compound 4-2.

| Run | Solvent | Vol | Temp (° C.) | Reaction Time (hr) | Pyrrolidine (eq.) | Compound 4-2 (%)* |
|---|---|---|---|---|---|---|
| 1** | 3-Pentanone | 2.5 | 95 | 21 | 2.0 | 90.6 |
| 2** | 3-Pentanone | 5.0 | 95 | 21 | 2.0 | 92.6 |
| 3 | 3-Pentanone | 6.25 | 95 | 19 | 2.0 | 100 |

*Note:
Compound 4-2 (%) = AUC (%) by HPLC
**Additional 3-pentanone (1.25 vol) added to progress the reaction to reported conversion.

Crystallization conditions were developed for the isolation of 2,2-diethyl-4-oxo-3,4-dihydro-2H-1-benzopyran-6-carboxylic acid Compound 4-2 (Table 6). The initial isolation of the product involved an acid-base extraction to yield Compound 4-2 as a yellow solid. The reaction mixture was diluted with ethyl acetate (EtOAc) and the pH was adjusted to 2 using 0.5 M HCl. Phase separation was carried out and the pH of the organic layer was adjusted to 5 using 5 M NaOH. The organic layer was concentrated under pressure to yield the desired product as a crystalline yellow solid. Next, direct crystallization from the reaction mixture was studied. It was found that crystallization occurred by first adding $H_2O$ followed by adjusting the pH of the reaction mixture to 2 using 5 M HCl to form a slurry. The slurry was filtered to yield Compound 4 as a yellow solid with a 59.8% yield. Different solvents were screened in attempts to improve the yield. Solids were not isolated when acetone and IPA were used as anti-solvents. n-Heptane was added to the slurry at 20° C. after the pH adjustment which resulted in a minor increase in yield. Next, the addition of n-heptane to the slurry at 10-15° C. caused a yield increase of 77.4%. These conditions were found to enhance the crystallization for 2,2-diethyl-4-oxo-3,4-dihydro-2H-1-benzopyran-6-carboxylic acid (Compound 4-2).

TABLE 6

Isolation Condition Screen for Synthesis of Compound 4-2.

| Run | Isolation Technique | Solvent | Anti-solvent | Temp (° C.) | Yield (%) | Compound 4-2 (%)* |
|---|---|---|---|---|---|---|
| 1 | Acid-Base Extraction | EtOAc | — | 20 | 60.3 | 100 |
| 2 | Crystallization | $H_2O$ | 5M HCl | 20 | 59.8 | 100 |
| 3 | Crystallization | $H_2O$ | Acetone | 20 | — | — |

TABLE 6-continued

| Isolation Condition Screen for Synthesis of Compound 4-2. | | | | | | |
|---|---|---|---|---|---|---|
| Run | Isolation Technique | Solvent | Anti-solvent | Temp (° C.) | Yield (%) | Compound 4-2 (%)* |
| 4 | Crystallization | $H_2O$ | IPA | 20 | — | — |
| 5 | Crystallization | $H_2O$ | n-Heptane | 20 | 61.4 | 100 |
| 6 | Crystallization | $H_2O$ | n-Heptane | 10-15 | 77.4 | 100 |

*Note:
Compound 4-2 (%) = AUC (%) by HPLC

Experimental of Synthesis of Compound 4-2:2,2-diethyl-4-oxo-3,4-dihydro-2H-1-benzopyran-6-carboxylic Acid To a stirred solution of 3-acetyl-4-hydroxy-benzoic acid (Compound 4-1, 20 g) in 3-pentanone (125 mL) was added pyrrolidine (18.5 mL). The reaction was heated to 95° C. and stirred for 19.5 hr. The reaction was cooled to 15-20° C. and $H_2O$ (60 mL) was added to form a slurry. The pH of the slurry was adjusted to 2 by addition of 5 M HCl, aq. (55 mL). n-Heptane (60 mL) was added and the slurry was stirred at 15-20° C. for approximately 1 hr. The slurry was filtered and the solid was washed with water (20 mL×2) and n-heptane (20 mL×2). The collected solid was dried at 50° C. under vacuum to yield 2,2-diethyl-4-oxo-3,4-dihydro-2H-1-benzopyran-6-carboxylic acid Compound 4-2 as a yellow solid (17.8 g, 64.5% yield). UPLC-qDa ($C_{14}H_{16}O_4$) calcd 249.11 $[M+H]^+$, found 249.19. $^1H$ NMR (500 MHZ, $CDCl_3$) δ ppm 0.95-0.98 (t, J=7.44 Hz, 6H), 1.74-1.87 (m, 4H), 2.79 (s, 2H), 7.03-7.05 (d, J=8.78 Hz, 1H), 8.19-8.21 (dd, J=8.78, 2.20 Hz, 1H), 8.65 (d, J=2.2 Hz, 1H).

Figure 4:
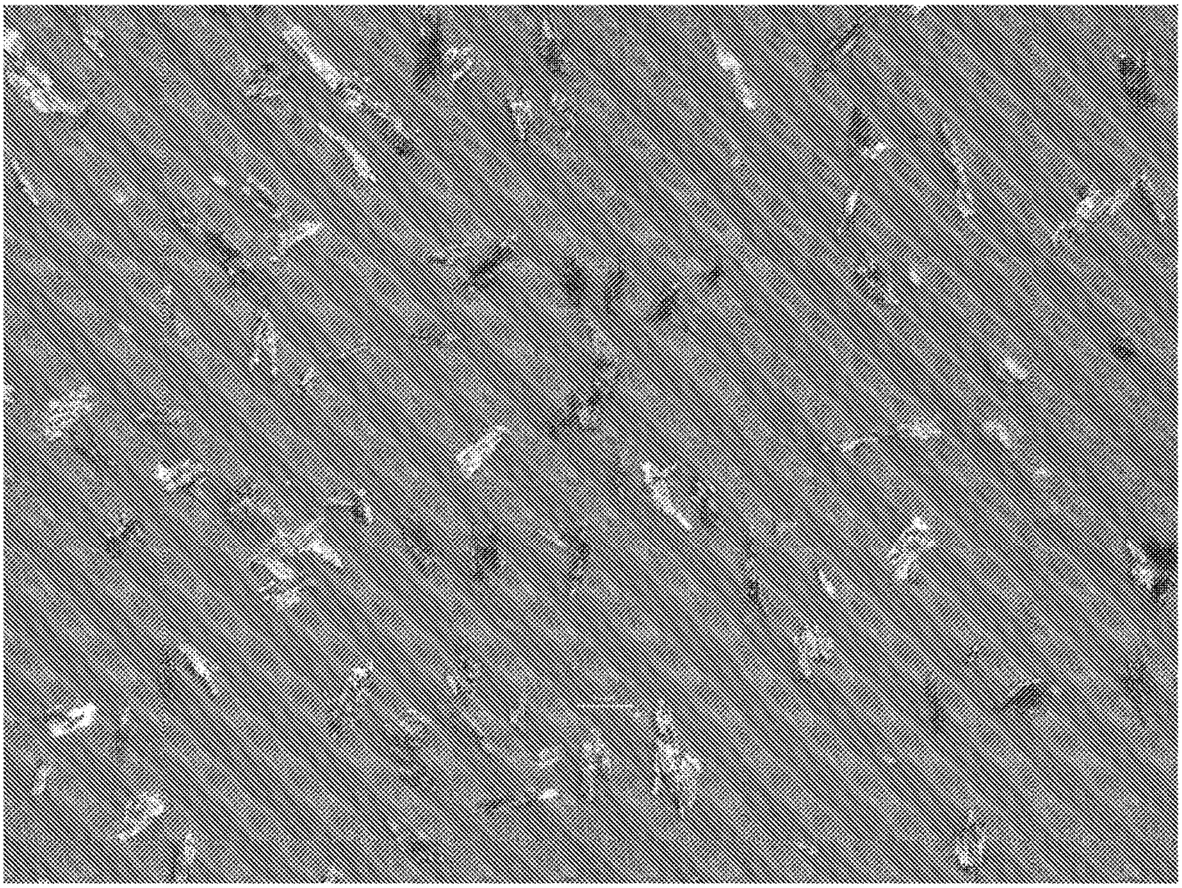
FIG. 4: Polarized Light Microscopy (PLM) analysis result of 6-(3-(1H-pyrazol-4-yl)-1,2,4-oxadiazol-5-yl)-2,2-diethylchroman-4-one (Compound 6-1) (10 μm Scale).
Figure 5:
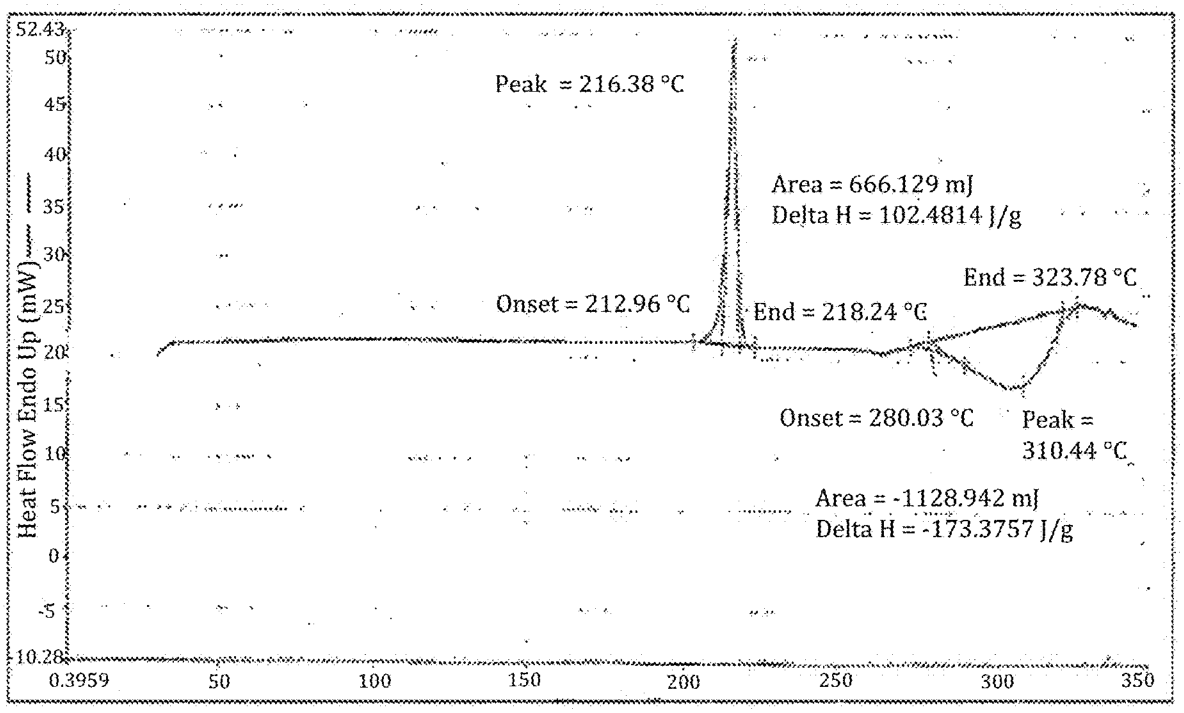
FIG. 5: Differential thermal analysis (DSC) result of 6-(3-(1H-pyrazol-4-yl)-1,2,4-oxadiazol-5-yl)-2,2-diethylchroman-4-one (Compound 6-1).

FIG. 4 shows the result of Polarized Light Microscopy (PLM) Analysis of 6-(3-(1H-pyrazol-4-yl)-1,2,4-oxadiazol-5-yl)-2,2-diethylchroman-4-one (Compound 6-1) (10 μm Scale) and one of skill in the art will understand that the result is generated by the traditional Polarized Light Microscopy method, which is known and appreciated by the one of skill in the art:

FIG. 5 shows the result of Differential thermal analysis. (DSC) of 6-(3-(1H-pyrazol-4-yl)-1,2,4-oxadiazol-5-yl)-2,2-diethylchroman-4-one (Compound 6-1) and one of skill in the art will understand that the result is generated by the traditional Polarized Light Microscopy method, which is known and appreciated by the one of skill in the art:

FIG. 6 and Table 14 show the result of X-ray powder diffraction (XRPD) results of 6-(3-(1H-pyrazol-4-yl)-1,2,4-oxadiazol-5-yl)-2,2-diethylchroman-4-one (Compound 6-1) and one of skill in the art will understand that the result is generated by the traditional Polarized Light Microscopy method, which is known and appreciated by the one of skill in the art. The parameters and conditions used for the X-ray powder diffraction (XRPD) regarding 2Theta are listed below:

| | |
|---|---|
| Name | S-19-0051893 TRV045 (5043) #1 |
| Parent | 2Theta |
| Sample ID | S-19-0051893 TRV045 |
| File Name | S-19-0051893 TRV045 (5043) |
| Experiment ID | 650 |
| Experiment Name | RM0858 General Method.bsml |
| Job ID | 5043 |
| Scan Type | Coupled TwoTheta/Theta |
| Scan Mode | Continuous PSD fast |
| Start | 2.000° |
| End | 40.017° |
| Step Size | 0.050° |
| Total time/Step | 192.00 s |
| Time/Step | 1.00 s |
| Sample Rotation | 15.000 1/min |
| Anode | Cu |
| ka1 | 1.54060 Å |
| Generator kV | 40.0 kV |
| Generator mA | 40.0 mA |
| Detector Name | LYNXEYE_XE_T (1D mode) |
| Detector Opening | 2.940° |
| Primary Soller slit | 2.500° |
| Secondary Soller slit | 2.500° |
| Divergence Slit | 0.600 mm |
| Antiscatter Slit | 3.000 mm |
| Slit Mode | Fixed |
| Operator Name | Harper |
| Sample Position | 1A01 |
| Creation Date/Time | Sep. 19, 2019 6:25:42 PM |
| Last Write Date/Time | Sep. 19, 2019 6:39:46 PM |
| Measurement Duration | 00:14:03 |

TABLE 14

X-ray powder diffraction (XRPD) results of 6-(3-(1H-pyrazol-4-yl)-1,2,4-oxadiazol-5-yl)-2,2-diethylchroman-4-one (Compound 6-1). XRPD peaks in FIG. 6 are indexed and listed herein.

| Index | Angle | d Value | Net Intensity | Gross Intensity | Rel. Intensity |
|---|---|---|---|---|---|
| 1 | 8.003° | 11.03897 Å | 210 | 919 | 1.1% |
| 2 | 8.501° | 10.39263 Å | 450 | 1089 | 2.3% |
| 3 | 8.853° | 9.98053 Å | 19893 | 20478 | 100.0% |
| 4 | 9.403° | 9.39772 Å | 19771 | 20266 | 99.4% |
| 5 | 12.804° | 6.90809 Å | 94.5 | 313 | 0.5% |
| 6 | 13.105° | 6.75037 Å | 465 | 677 | 2.3% |
| 7 | 14.055° | 6.29621 Å | 45.2 | 239 | 0.2% |
| 8 | 14.205° | 6.22987 Å | 175 | 368 | 0.9% |
| 9 | 14.857° | 5.95798 Å | 849 | 1056 | 4.3% |
| 10 | 15.055° | 5.87996 Å | 199 | 411 | 1.0% |
| 11 | 15.506° | 5.71006 Å | 2289 | 2509 | 11.5% |
| 12 | 15.706° | 5.63778 Å | 17312 | 17533 | 87.0% |
| 13 | 16.606° | 5.33417 Å | 885 | 1098 | 4.4% |
| 14 | 17.043° | 5.19850 Å | 93.6 | 300 | 0.5% |
| 15 | 17.156° | 5.16429 Å | 17.2 | 223 | 0.1% |
| 16 | 17.707° | 5.00498 Å | 2102 | 2315 | 10.6% |
| 17 | 17.857° | 4.96327 Å | 726 | 941 | 3.6% |
| 18 | 18.058° | 4.90850 Å | 144 | 360 | 0.7% |
| 19 | 18.857° | 4.70211 Å | 10882 | 11090 | 54.7% |
| 20 | 22.059° | 4.02630 Å | 668 | 835 | 3.4% |
| 21 | 23.760° | 3.74181 Å | 796 | 1013 | 4.0% |
| 22 | 24.010° | 3.70341 Å | 1348 | 1575 | 6.8% |
| 23 | 24.260° | 3.66587 Å | 3818 | 4054 | 19.2% |
| 24 | 24.806° | 3.58637 Å | 1223 | 1471 | 6.1% |
| 25 | 24.960° | 3.56460 Å | 971 | 1221 | 4.9% |
| 26 | 25.410° | 3.50243 Å | 1397 | 1648 | 7.0% |
| 27 | 26.010° | 3.42298 Å | 4318 | 4563 | 21.7% |
| 28 | 26.261° | 3.39092 Å | 1051 | 1290 | 5.3% |
| 29 | 26.711° | 3.33479 Å | 4077 | 4300 | 20.5% |
| 30 | 27.310° | 3.26290 Å | 91.9 | 286 | 0.5% |
| 31 | 27.661° | 3.22230 Å | 99.1 | 272 | 0.5% |
| 32 | 28.462° | 3.13347 Å | 117 | 272 | 0.6% |
| 33 | 28.662° | 3.11206 Å | 85.3 | 243 | 0.4% |
| 34 | 28.812° | 3.09616 Å | 52.7 | 212 | 0.3% |
| 35 | 29.062° | 3.07013 Å | 440 | 601 | 2.2% |
| 36 | 29.412° | 3.03436 Å | 97.2 | 257 | 0.5% |
| 37 | 29.762° | 2.99942 Å | 206 | 362 | 1.0% |
| 38 | 30.011° | 2.97515 Å | 214 | 364 | 1.1% |
| 39 | 30.918° | 2.88992 Å | 19.5 | 168 | 0.1% |
| 40 | 31.338° | 2.85210 Å | 175 | 333 | 0.9% |
| 41 | 32.013° | 2.79349 Å | 284 | 448 | 1.4% |
| 42 | 32.313° | 2.76824 Å | 51.2 | 213 | 0.3% |
| 43 | 32.414° | 2.75986 Å | 96.0 | 257 | 0.5% |
| 44 | 32.813° | 2.72717 Å | 184 | 337 | 0.9% |

TABLE 14-continued

X-ray powder diffraction (XRPD) results of 6-(3-(1H-pyrazol-4-yl)-1,2,4-oxadiazol-5-yl)-2,2-diethylchroman-4-one (Compound 6-1). XRPD peaks in FIG. 6 are indexed and listed herein.

| Index | Angle | d Value | Net Intensity | Gross Intensity | Rel. Intensity |
|---|---|---|---|---|---|
| 45 | 32.912° | 2.71919 Å | 97.2 | 248 | 0.5% |
| 46 | 33.212° | 2.69533 Å | 148 | 289 | 0.7% |
| 47 | 33.764° | 2.65255 Å | 119 | 250 | 0.6% |
| 48 | 34.764° | 2.57847 Å | 627 | 768 | 3.2% |
| 49 | 35.314° | 2.53959 Å | 44.1 | 188 | 0.2% |
| 50 | 35.864° | 2.50189 Å | 659 | 800 | 3.3% |
| 51 | 36.265° | 2.47515 Å | 73.9 | 209 | 0.4% |
| 52 | 36.666° | 2.44900 Å | 72.0 | 207 | 0.4% |
| 53 | 37.516° | 2.39541 Å | 288 | 430 | 1.4% |

General Procedure C:

Scheme 5

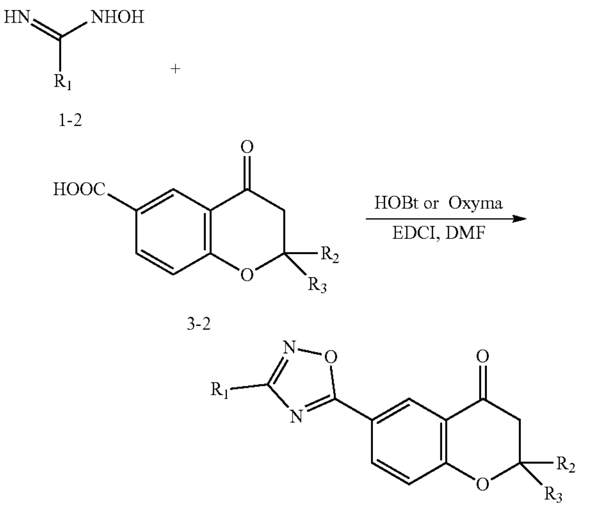

1-2

3-2

5-1

Example 2: Synthesis of Compound 6-1:6-(3-(1H-pyrazol-4-yl)-1,2,4-oxadiazol-5-yl)-2,2-diethylchroman-4-one Scheme 6

Route 1

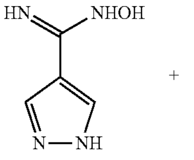

2-2

-continued

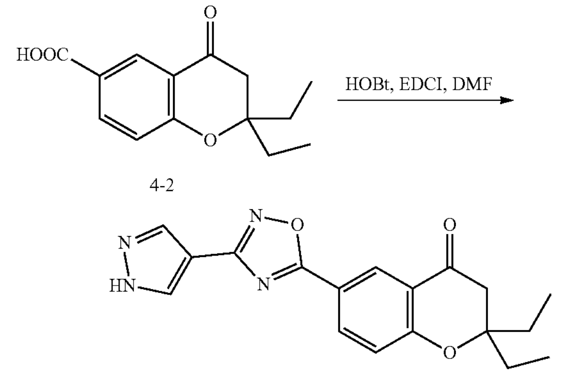

4-2

6-1

Route 2

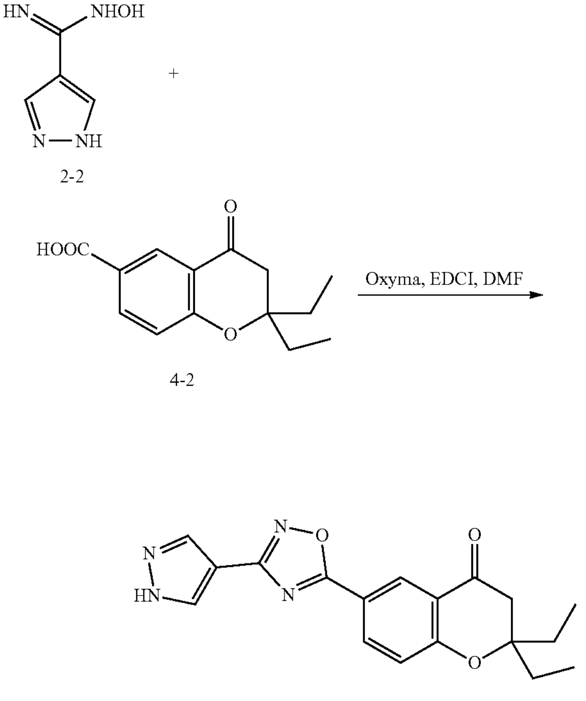

2-2

4-2

6-1

Synthesis of Compound 6-1:6-(3-(1H-pyrazol-4-yl)-1,2,4-oxadiazol-5-yl)-2,2-diethylchroman-4-one 2-Methyltetrahydrofuran (MeTHF) was screened as a potential solvent for the synthesis of Compound 6-1 (Table 7). An alternative solvent was studied because DMF can be difficult to purge due to its low evaporation rate. The reaction was carried out in MeTHF (10 vol) in 10 volumes of Compound 4-2 at 75° C. Over the course of the reaction, the reaction mixture became very viscous and isolation of the product proved to be difficult. The reaction produced Compound 4-2 in 21.9% yield. For comparison purpose, a reaction was carried out in DMF (10 vol) in 10 volumes of Compound 4-2 at 95° C. in parallel. The isolation of the Compound 6-1 was obtained via crystallization with 64.3% yield. DMF was found to be the an appropriate solvent for the synthesis of Compound 6-1.

TABLE 7

Solvent Screen for Synthesis of Compound 6-1.

| Run | Solvent | Vol | Temp (° C.) | Reaction Time (hr) | EDCI (eq.) | Oxyma (eq.) | Compound 2-2 (eq.) | Yield (%) |
|---|---|---|---|---|---|---|---|---|
| 1 | MeTHF | 10 | 75 | 16 | 1.2 | 1.0 | 1.2 | 21.9 |
| 2 | DMF | 10 | 95 | 18 | 1.2 | 1.0 | 1.2 | 64.3 |

Volumes of DMF were screened to identify the concentration for the reaction and crystallization (Table 8). The reaction carried out in DMF (15 vol) in 15 volumes of Compound 4-2 resulted in a low yield which could be caused to the solubility of the product in DMF. The reaction carried out DMF (2.5 vol) in 2.5 volumes of Compound 4-2 became very viscous and isolation of the product proved to be difficult. Even though the reaction resulted in a good yield, the purity of Compound 6-1 was found to be low. The reactions carried out in DMF (5 vol and 10 vol) in 5 and 10 volumes of Compound 4-2 showed promising results with similar yield. The volume of DMF for in one embodiments of the reaction was found to be 5 volumes of Compound 4-2.

TABLE 8

Volume of DMF Screen for Synthesis of Compound 6-1.

| Run | Solvent | Vol | Temp (° C.) | Reaction Time (hr) | EDCI (eq.) | Oxyma (eq.) | Compound 2-2 (eq.) | Yield (%) | Compound 6-1 (%)* |
|---|---|---|---|---|---|---|---|---|---|
| 1 | DMF | 15 | 95 | 14.5 | 1.2 | 1.0 | 1.2 | 34.6 | 96.2 |
| 2 | DMF | 10 | 95 | 18 | 1.2 | 1.0 | 1.2 | 71.5 | 97.3 |
| 3 | DMF | 5 | 95 | 18 | 1.2 | 1.0 | 1.2 | 72.7 | 97.9 |
| 4 | DMF | 2.5 | 95 | 20 | 1.2 | 1.0 | 1.2 | 75.9 | 58.9 |

*Note:
Compound 6-1 (%) = AUC (%) by HPLC

The initial isolation technique for Compound 6-1 involved column chromatography. The isolation of the desired Compound 6-1 via column chromatography resulted in a low yield of 34.6%. Crystallization conditions were screened to eliminate chromatography (Table 9). Direct crystallization from the reaction mixture was explored for the isolation of Compound 6-1. The addition of water to the reaction mixture initiated crystallization of the desired Compound 6-1. The appearance of Compound 6-1 was reported as a white solid in Patent Application Publication WO 2018/231745. However, the solid isolated from the crystallization was a tan solid. In the attempt to improve the appearance of the solid and the yield, the addition of anti-solvent was explored. The addition of $H_2O$ followed by 5 M NaOH at 20° C. resulted in a slight improvement in appearance but a lower yield of 64.3%. Next, the addition of $H_2O$ and 5 M NaOH at 5° C. showed a small increase in yield. The addition of $H_2O$ followed by 5 M HCl at 20° C. resulted in a minor improvement in appearance and a lower yield of 63.5%. Incorporating MeOH as an anti-solvent resulted in a significant decrease in yield. The addition of water to the reaction mixture at 5° C. resulted in a similar yield when compared to the addition performed at 20° C. Higher volumes of water were explored, and it was found that the yield did not increase significantly with the increased volume of water. Based on yield and appearance, crystallization via the addition of $H_2O$ (10 vol) in 10 volumes of Compound 4-2 at 20° C. was found to be the best condition for the isolation of Compound 6-1.

TABLE 9

Isolation Condition Screen for Synthesis of Compound 6-1.

| Run | Isolation Technique | Solvent (Vol) | Anti-solvent | Temp (° C.) | Yield (%) |
|---|---|---|---|---|---|
| 1 | Column Chromatography | — | — | — | 34.6 |
| 2 | Crystallization | $H_2O$ (5) | — | 20 | 71.5 |
| 3 | Crystallization | $H_2O$ (5) | 5M NaOH | 20 | 64.3 |
| 4 | Crystallization | $H_2O$ (5) | 5M NaOH | 5 | 71.2 |
| 5 | Crystallization | $H_2O$ (5) | 5M HCl | 20 | 63.5 |
| 6 | Crystallization | $H_2O$ (5) | MeOH | 20 | 30.8 |
| 7 | Crystallization | $H_2O$ (5) | — | 5 | 69.9 |
| 8 | Crystallization | $H_2O$ (10) | — | 20 | 72.8 |
| 9 | Crystallization | $H_2O$ (15) | — | 20 | 73.4 |

Crystallization of Compound 6-1 resulted in a crystalline tan solid. The presence of Oxyma in the product was a potential contributing factor to the color of the product therefore the Oxyma loading was screened (Table 10). The progression of the reaction decreased considerably with the lower Oxyma loading. The lower Oxyma loading did not improve the appearance of the Compound 6-1and resulted in a substantial decrease in yield.

TABLE 10

Reagent Loading Screen for Synthesis of Compound 6-1.

| Run | Solvent | Vol | Temp (° C.) | Reaction Time (hr) | EDCI (eq.) | Oxyma (eq.) | Compound 2-2 (eq.) | Yield (%) |
|---|---|---|---|---|---|---|---|---|
| 1 | DMF | 5 | 95 | 24 | 1.2 | 0.10 | 1.0 | 31.8 |
| 2 | DMF | 5 | 95 | 24 | 1.2 | 0.25 | 1.0 | 42.0 |
| 3 | DMF | 5 | 95 | 24 | 1.2 | 0.50 | 1.0 | 45.6 |

Different color remediation conditions were screened to improve the appearance of Compound 6-1. The purity and potency (% w/w) of the drug substance was analyzed concurrently. The potency was tabulated based on the input material being normalized to 100%. First, recrystallization of the tan Compound 6-1 was explored as a color remediation method to improve the appearance of Compound 6-1 (Table 11). DMF and dimethyl sulfoxide (DMSO) were chosen due to the fact that Compound 6-1 was soluble in these two solvents. The tan Compound 6-1 was brought into solution with the noted solvent at the desired temperature and stirred for 4 hr. Crystallization occurred upon the addition of water at 15-20° C. and the solid was obtained via filtration. Recrystallization in DMSO at 20° C. resulted in improved appearance, purity and potency. Different temperatures were screened for the recrystallization in DMF. The higher temperatures in DMF yielded a decrease in both the potency and recovery of the final Compound 6-1.

TABLE 11

Color Remediation Screen for Recrystallization of tan Compound 6-1

| | Vol of Solvent | Temp (° C.) | Appearance | Purity (%)* | Compound 6-1 (% w/w) | Recovery (%) |
|---|---|---|---|---|---|---|
| Input | — | — | Orangish-White | 95.8 | 100 | — |
| DMSO | 5 | 20 | Off White to White | 98.3 | 106.9 | 84.4 |
| DMF | 5 | 20 | Off White to White | 97.7 | 107.1 | 83.0 |

TABLE 11-continued

Color Remediation Screen for Recrystallization of tan Compound 6-1

| | Vol of Solvent | Temp (° C.) | Appearance | Purity (%)* | Compound 6-1 (% w/w) | Recovery (%) |
|---|---|---|---|---|---|---|
| DMF | 5 | 45 | Off White to White | 97.8 | 101.7 | 82.2 |
| DMF | 5 | 90 | Off White to White | 97.4 | 102.0 | 77.3 |

*Note:
Purity (%) = AUC (%) by HPLC

Next, charcoal treatment was utilized as a color remediation approach (Table 12). DMF and DMSO were used as solvents due to the solubility of Compound 6-1. The charcoal treatment comprised of activated charcoal (5 wt %) being charged to a solution of the tan Compound 6-1 in the noted solvent and stirred at 20° C. for 5 hr. The charcoal was filtered off, crystallization occurred upon the addition of water at 15-20° C. and the solid was obtained via filtration. The charcoal treatment in DMF resulted in an increase in both purity and potency with a 63.4% recovery. The charcoal treatment in DMSO showed a slightly lower purity and potency but a higher recovery of 70.4% when compared to DMF.

TABLE 12

Color Remediation Screen: Charcoal Treatment

| | Vol of Solvent | Appearance | Purity (%)* | Compound 6-1 (% w/w) | Recovery (%) |
|---|---|---|---|---|---|
| Input | — | Orangish-White | 97.3 | 100 | — |
| DMF & Charcoal | 5 | Off White to White | 99.3 | 107.3 | 63.4 |
| DMSO & Charcoal | 5 | Off White to White | 98.9 | 104.8 | 70.4 |

*Note:
Purity (%) = AUC (%) by HPLC

Another approach for color remediation was to reslurry the tan Compound 6-1 in different solvents in which it exhibited low solubility. Various solvents were screened for the reslurry (Table 13). The reslurry procedure involved stirring the Compound 6-1 in the desired solvent at the noted temperature for 15 hr. The final Compound 6-1 was isolated via filtration. The isolated solid from the reslurry in MeOH, EtOAc, and acetone showed a visual improvement in color. However, the reslurry in these solvents resulted in such a low recovery that the purity and potency were not analyzed. Reslurry in MTBE at 45° C. produced a white to off-white solid with 97.2% purity, 101.8% potency and 81.2% recovery. Different solvent volumes and temperatures were screened for the reslurry in EtOH. The isolated solid from the reslurry in EtOH (10 vol) in 10 volumes of Compound 6-1 at 45° C. showed a visual improvement in color. However, the reslurry resulted in such a low recovery that the purity and potency were not analyzed. The final Compound 6-1 obtained from the reslurry in EtOH (10 vol) at 20° C. yielded a 98.7% purity, 101.7% potency and 75.7% recovery. The final Compound 6-1 obtained from the reslurry in EtOH (5 vol) in 5 volumes of Compound 6-1 at 75° C. yielded a 99.8% purity, 105.6% potency and 66.0% recovery.

The recrystallization and charcoal treatment in DMSO and DMF were not chosen as the color remediation procedures. They did yield favorable improvements to the Compound 6-1. However, both solvents would be difficult to purge due to the high boiling point of each. The reslurry in EtOH (5 vol) in volumes of Compound 6-1 at 75° C. showed the most promising results and was chosen as the color remediation method for tan Compound 6-1.

TABLE 13

Color Remediation Screen: Reslurry

| | Vol of Solvent | Temp (° C.) | Appearance | Purity (%)* | Compound 6-1 (% w/w) | Recovery (%) |
|---|---|---|---|---|---|---|
| Input | — | — | Orangish-White | 97.3 | 100 | — |
| MeOH | 10 | 20 | Off White to White | — | — | 11.0 |
| EtOAc | 10 | 45 | Off White to White | — | — | 53.3 |
| Acetone | 10 | 20 | Off White to White | — | — | 33.0 |
| MTBE | 10 | 45 | Off White to White | 97.2 | 101.8 | 81.2 |
| EtOH | 10 | 20 | Off White to White | 98.7 | 101.7 | 75.7 |
| EtOH | 10 | 45 | Off White to White | — | — | 45.3 |
| EtOH | 5 | 75 | Off White to White | 99.8 | 105.6 | 66.0 |

*Note:
Purity (%) = AUC (%) by HPLC

Experimental of Synthesis of Compound 6-1:6-(3-(1H-pyrazol-4-yl)-1,2,4-oxadiazol-5-yl)-2,2-diethylchroman-4-one To a stirred solution of 2,2-diethyl-4-oxo-3,4-dihydro-2H-1-benzopyran-6-carboxylic acid (Compound 4-2, 70 g) in N,N-dimethylformamide (DMF, 350 mL) was added EDCI (64.9 g) and ethyl cyanohydroxyiminoacetate (Oxyma, 40.1 g). The reaction was stirred at ambient temperature for 1 hr. N-Hydroxy-1H-pyrazole-4-carboximidamide (Compound 2-2, 42.7 g) was added and the reaction was stirred at ambient temperature for 1 hr. The reaction was heated to 95° C. and stirred for 5 hr. The reaction was cooled to 15-20° C. and $H_2O$ (700 mL) was added to form a slurry. The slurry was stirred at 15-20° C. for approximately 1 hr. The slurry was filtered to obtain a solid and the solid was washed with water (175 mL×2) and methyl-t-butyl ether ("MTBE") (175 mL×2). The collected solid was dried at 55° C. under vacuum to yield the tan Compound 6-1 as a tan solid (75.2 g).

The tan Compound 6-1 was stirred with EtOH (375 mL) to form a slurry and the slurry was heated to 75° C. The slurry was held at 75° C. for 16 hr. The slurry was cooled to 15-20° C. and stirred for approximately 1 hr. The slurry was filtered and the solid was washed with EtOH (100 mL×3). The collected solid was dried at 55° C. under vacuum to yield 6-(3-(1H-pyrazol-4-yl)-1,2,4-oxadiazol-5-yl)-2,2-diethylchroman-4-one (Compound 6-1) as a white to off-white solid (63.2 g, 66.2% yield).

UPLC-qDa ($C_{18}H_{18}N_4O_3$) calcd 339.15 $[M+H]^+$, found 339.14.

$^1H$ NMR (500 MHz, DMSO-$d_6$) δ ppm 0.88-0.91 (t, J=7.44 Hz, 6H), 1.70-1.81 (m, 4H), 2.92 (s, 2H), 7.26-7.28

(d, J=8.78 Hz, 1H), 8.06 (s, 1H), 8.25-8.28 (dd, J=8.66, 2.32 Hz, 1H), 8.43-8.44 (d, J=2.20 Hz, 1H), 8.48 (s, 1H), 13.48 (bs, 1H).

Ester Intermediates of Synthesis of Compound 6-1: 6-(3-(1H-pyrazol-4-yl)-1,2,4-oxadiazol-5-yl)-2,2-diethylchroman-4-one The one-pot process in Scheme 7 consisted of two distinct chemical bond-forming transformations. First, an esterification occurred by activation of 2,2-diethyl-4-oxo-3,4-dihydro-2H-1-benzopyran-6-carboxylic acid (Compound 4-2) with 1-ethyl-3-(3-dimethylaminopropyl) carbodiimide (EDCI) and ethyl cyanohydroxyiminoacetate (Oxyma) to yield Intermediate 7-1. Next, esterification occurred by activation of Intermediate 7-1 in the presence of N-hydroxy-1H-pyrazole-4-carboximidamide (Compound 2-2) to yield Intermediate 7-2. The esterification between Compound 4-2 and Compound 2-2 was then followed by thermal cyclodehydration to yield Compound 6-1. The two transient intermediates were isolated and characterized in the traditional methods that one of skill in the art would know and use for in-process analysis purposes.

Scheme 7

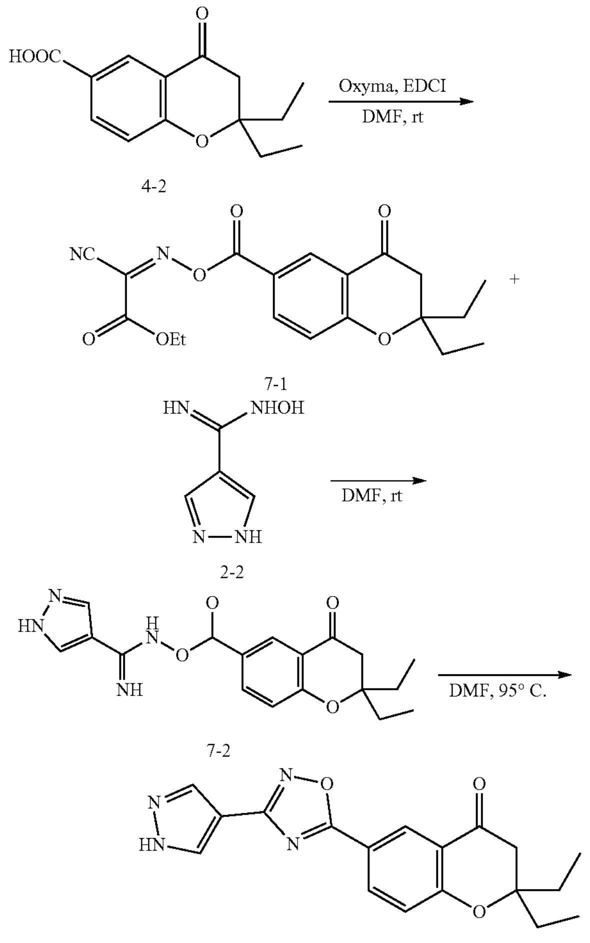

4-2

7-1

2-2

7-2

6-1

Intermediate 7-1: ethyl (Z)-2-cyano-2-(((2,2-diethyl-4-oxochromane-6-carbonyl)oxy)imino)acetate $^1$H-NMR of Oxyma Ester Intermediate 7-1: $^1$H NMR (500 MHz, $CDCl_3$) δ ppm 0.95-0.98 (t, J=7.44 Hz, 6H), 1.44-1.47 (t, J=7.08 Hz, 3H), 1.74-1.88

(m, 4H), 2.80 (s, 2H), 4.50-4.54 (q, J=7.16 Hz, 2H), 7.09-7.10 (d, J=8.78 Hz, 1H), 8.22-8.25 (dd, J=8.78, 2.22 Hz, 1H), 8.69-8.70 (d, J=2.20 Hz, 1H).

Intermediate 7-2: N-((2,2-diethyl-4-oxochromane-6-carbonyl)oxy)-1H-pyrazole-4-carboximidamide $^1$H-NMR of Oxyma Ester Intermediate 7-2: $^1$H NMR (400 MHZ, $CDCl_3$) δ ppm 0.85-0.88 (t, J=7.22 Hz, 6H), 1.61-1.78 (m, 4H), 2.67 (s, 2H), 5.93 (bs, 2H), 6.86-6.88 (d, J=8.59 Hz, 1H), 7.85 (s, 2H), 8.05-8.08 (dd, J=8.78, 1.95 Hz, 1H), 8.39-8.40 (d, J=1.95 Hz, 1H).

What is claimed is:

1. A crystalline form of a compound having the formula of

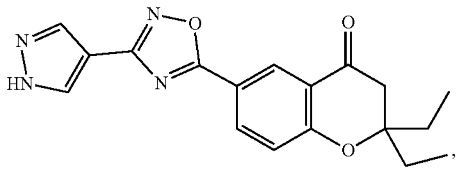 [SMILES: CCC1(CC)CC(=O)c2cc(-c3nc(-c4cn[nH]c4)no3)ccc2O1]

or a pharmaceutically acceptable salt thereof, wherein the crystalline form is characterized by an X-ray powder diffraction pattern comprising one or more peaks at about 8.9±0.5 degrees 2θ, at about 9.4±0.5 degrees 2θ, 15.7±0.5 degrees 2θ, at about 17.7±0.5 degrees 2θ, at about 18.9±0.5 degrees 2θ, 24.3±0.5 degrees 2θ, at about 26.0±0.5 degrees 2θ, and at about 26.7±0.5 degrees 2θ.

2. The crystalline Form I of claim 1, or a pharmaceutically acceptable salt thereof, characterized by an X-ray powder diffraction pattern comprising one or more d-spacing values at about 10.0±0.5 degrees angstroms, at about 9.4±0.5 degrees angstroms, at about 5.6±0.5 degrees angstroms, at about 5.0±0.5 degrees angstroms, at about 4.7±0.5 degrees angstroms, at about 3.7±0.5 degrees angstroms, at about 3.4±0.5 degrees angstroms, and at about 3.3±0.5 degrees angstroms.

3. A pharmaceutical composition comprising the crystalline form of claim 1.

4. A pharmaceutical composition comprising the crystalline form of claim 2.

* * * * *